US011273167B2

(12) United States Patent
Lishko et al.

(10) Patent No.: US 11,273,167 B2
(45) Date of Patent: Mar. 15, 2022

(54) COMPOSITIONS AND METHODS FOR MODULATING ABHD2 ACTIVITY

(71) Applicant: The Regents of the University of California, Oakland, CA (US)

(72) Inventors: Polina V. Lishko, Berkeley, CA (US); Yuriy Kirichok, San Francisco, CA (US); Melissa R. Miller, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 487 days.

(21) Appl. No.: 15/747,104

(22) PCT Filed: Aug. 1, 2016

(86) PCT No.: PCT/US2016/045029
§ 371 (c)(1),
(2) Date: Jan. 23, 2018

(87) PCT Pub. No.: WO2017/023861
PCT Pub. Date: Feb. 9, 2017

(65) Prior Publication Data
US 2018/0216156 A1 Aug. 2, 2018

Related U.S. Application Data

(60) Provisional application No. 62/200,292, filed on Aug. 3, 2015.

(51) Int. Cl.
| | |
|---|---|
| *C12Q 1/44* | (2006.01) |
| *C07K 16/40* | (2006.01) |
| *C12N 15/113* | (2010.01) |
| *C12N 5/076* | (2010.01) |
| *C12N 5/0793* | (2010.01) |
| *C12N 5/071* | (2010.01) |
| *G01N 33/50* | (2006.01) |
| *A61K 31/66* | (2006.01) |
| *G01N 33/68* | (2006.01) |
| *A61K 31/713* | (2006.01) |
| *A61K 38/46* | (2006.01) |
| *A61K 39/395* | (2006.01) |
| *A61K 31/58* | (2006.01) |

(52) U.S. Cl.
CPC .............. *A61K 31/66* (2013.01); *A61K 31/58* (2013.01); *A61K 31/713* (2013.01); *A61K 38/465* (2013.01); *A61K 39/395* (2013.01); *C07K 16/40* (2013.01); *C12N 5/061* (2013.01); *C12N 5/0619* (2013.01); *C12N 5/0688* (2013.01); *C12N 15/1137* (2013.01); *C12Q 1/44* (2013.01); *C12Y 301/01* (2013.01); *C12Y 301/01023* (2013.01); *G01N 33/5023* (2013.01); *G01N 33/6872* (2013.01); *C12N 2310/11* (2013.01); *C12N 2310/14* (2013.01)

(58) Field of Classification Search
CPC ...... A61K 31/66; A61K 31/58; A61K 31/713; A61K 38/465; A61K 39/395; C07K 16/40; C12N 5/061; C12N 5/0619; C12N 5/0688; C12N 15/1137; C12N 2310/11; C12N 2310/14; C12Q 1/44; C12Y 301/01; C12Y 301/01023; G01N 33/5023; G01N 33/6872
USPC ........................................................ 514/139
See application file for complete search history.

(56) References Cited

U.S. PATENT DOCUMENTS

2014/0255431 A1   9/2014   Majeti et al.

FOREIGN PATENT DOCUMENTS

| CN | 101063129 B | 12/2010 |
|---|---|---|
| JP | 2006006151 A | 1/2006 |
| WO | WO 2005/007150 | 1/2005 |
| WO | WO 2010/056309 | 5/2010 |
| WO | WO 2010/124121 | 10/2010 |

OTHER PUBLICATIONS

Farkas, et al.; "Insulinoma-Associated 1 Has a Panneurogenic Role and Promotes the Generation and Expansion of Basal Progenitors in the Developing Mouse Neocortex"; Neuron; vol. 60, pp. 40-55 (Oct. 9, 2008).
Jin, et al.; "Age-related pulmonary emphysema in mice lacking α/β hydrolase domain containing 2 gene"; Biochemical and Biophysical Research Communications; vol. 380, Issue 2, pp. 419-424 (Mar. 6, 2009). [Abstract only].
Zhu, et al.; "Differential proteomic profiling in human spermatozoa that did or did not result in pregnancy via IVF and AID"; Proteomics Clin. Appl.; vol. 7, pp. 850-858 (2013).
Ding, et al.; "Antisense Oligonucleotides Targeting Abhydrolase Domain Containing 2 Block Human Hepatitis B Virus Propagation"; Oligonucleotides; vol. 21, No. 2, 10 pages (2011).
Long, et al.; "The Metabolic Serine Hydrolases and Their Functions in Mammalian Physiology and Disease"; Chemical Reviews; vol. 111, pp. 6022-6063 (2011).
Miller, et al.; "Unconventional endocannabinoid signaling governs sperm activation via the sex hormone progesterone"; Science; vol. 352, No. 6285, 6 pages (Apr. 29, 2016).

*Primary Examiner* — Kristin A Vajda
(74) *Attorney, Agent, or Firm* — Bozicevic Field & Francis, LLP; Paula A. Borden

(57) ABSTRACT

The present disclosure provides compositions and methods of modulating abhydrolase domain-containing protein-2 (ABHD2). The present disclosure provides methods of identifying agents that modulate ABHD2 activity.

4 Claims, 18 Drawing Sheets
Specification includes a Sequence Listing.

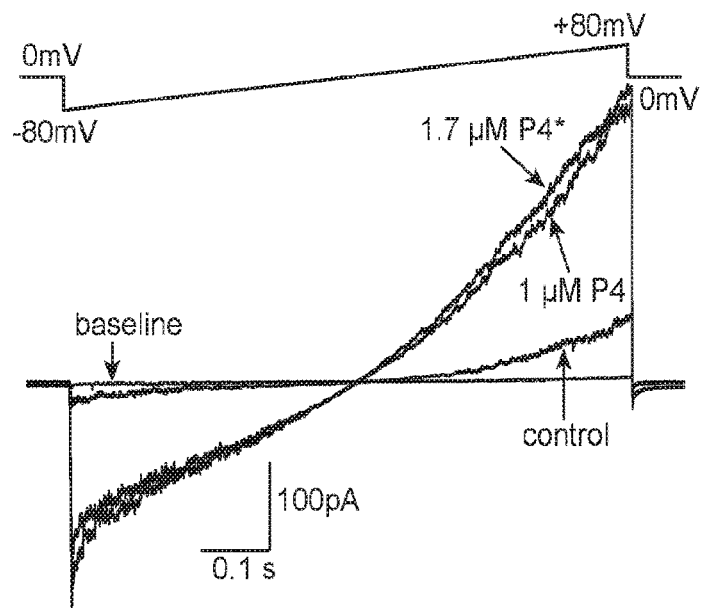
FIG. 1A
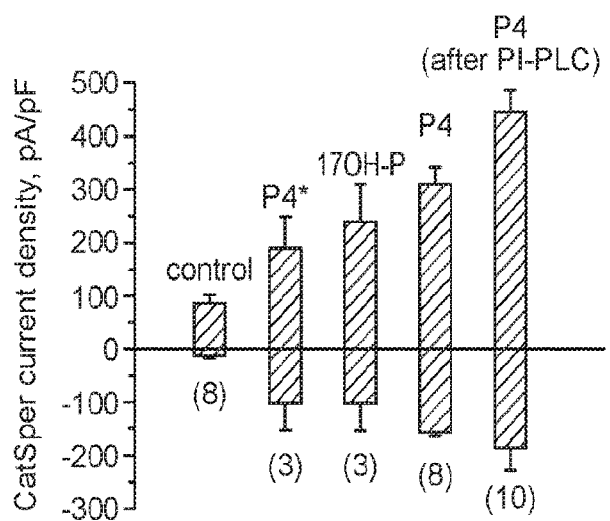
FIG. 1B
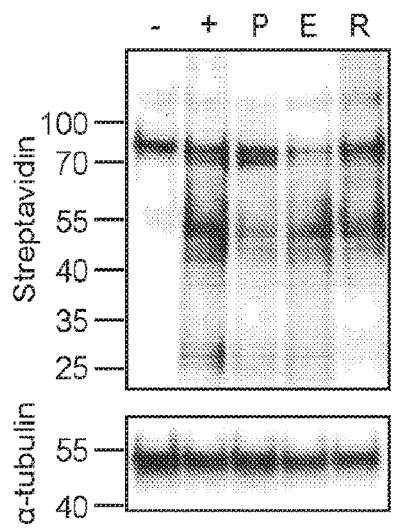
FIG. 1C
FIG. 1D
| top candidates | # of differing peptides | % coverage | sequence | # |
|---|---|---|---|---|
| alpha/beta hydrolase domain containing protein 2 | 1 | 4.0% | K.SPTAPPDLYFQDSGLSR.F | 3 |
| fatty-acid amide hydrolase 1 | 3 | 5.9% | R.RTARGAVVR.A<br>R.ELAPEAVLFTYVGK.A<br>R.LDPTVPPLPFR.E | 1<br>2<br>2 |
| prostatic acid phosphatase | 1 | 3.0% | R.SPIDTFPTDPIK.E | 1 |

FIG. 2C
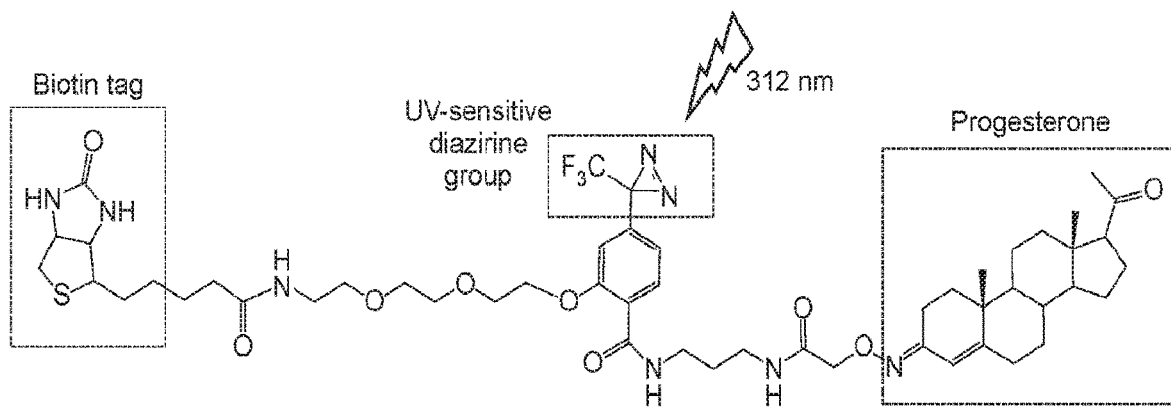
Progesterone-3-CMO-(2-biotinyl-PEG2-aminopropylamido-4-trifluoromethyl diazirinyl) benzamide (P4*)
FIG. 2D
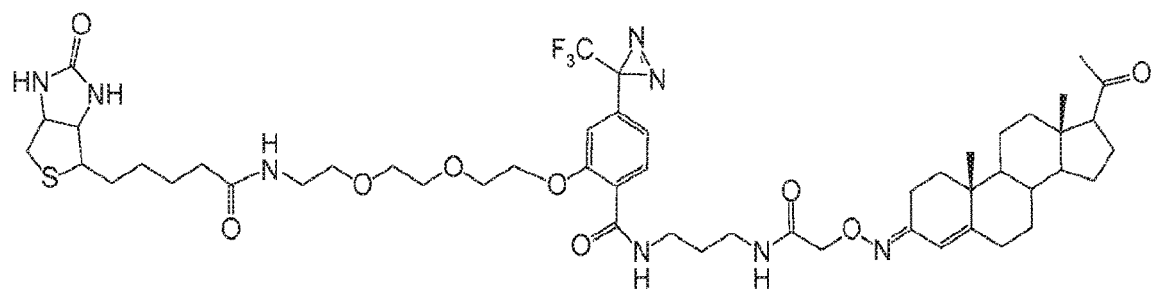
Chemical Formula: $C_5{}_1H_{71}F_3N_8O_9S$
Molecular Weight: 1029.22
Elemental Analysis: C, 59.52; H, 6.95; F, 5.54; N, 10.89; O, 13.99; S, 3.12
$-N_2$ ↓ 1) UV
2) Protein
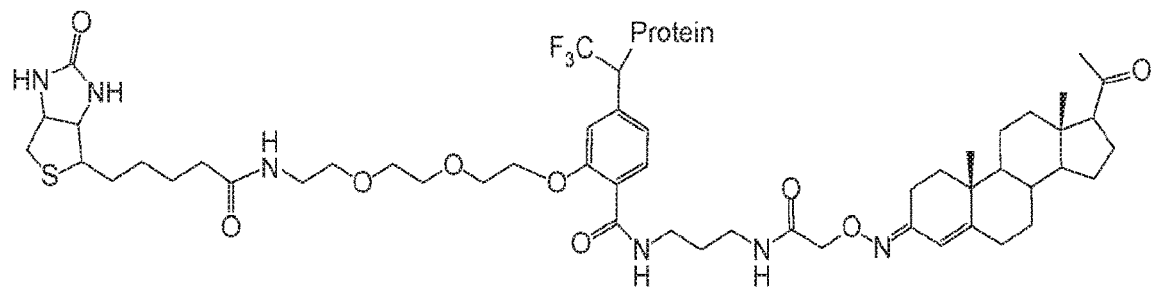
Chemical Formula: $C_5{}_1H_{72}F_3N_6O_9S$
Molecular Weight: 1002.21
Elemental Analysis: C, 61.12; H, 7.24; F, 5.69; N, 8.39; O, 14.37; S, 3.20

FIG. 5C
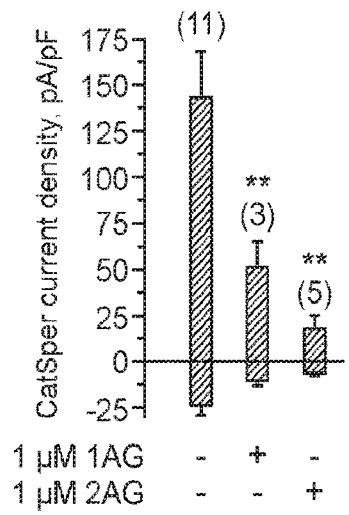
FIG. 5D
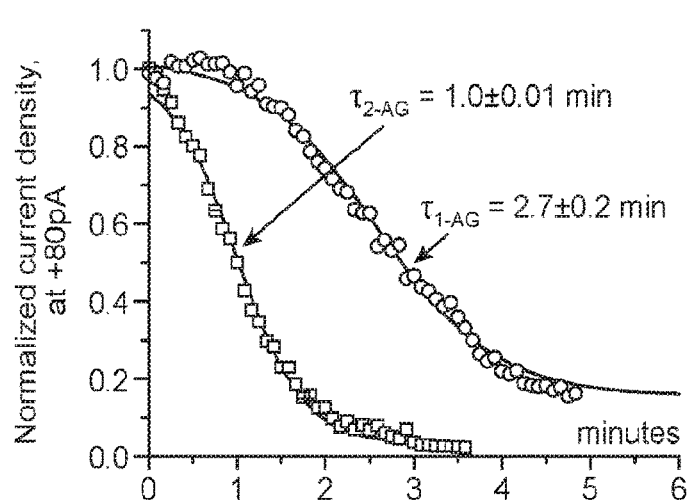
FIG. 5E
| | 1-AG/2-AG | |
|---|---|---|
| | Normalized sample AUC | fmols / sample |
| Blank | 9232 | 20 |
| sperm + vehicle | 123209 | 240 |
| sperm + P4 | 10679 | |
FIG. 6A
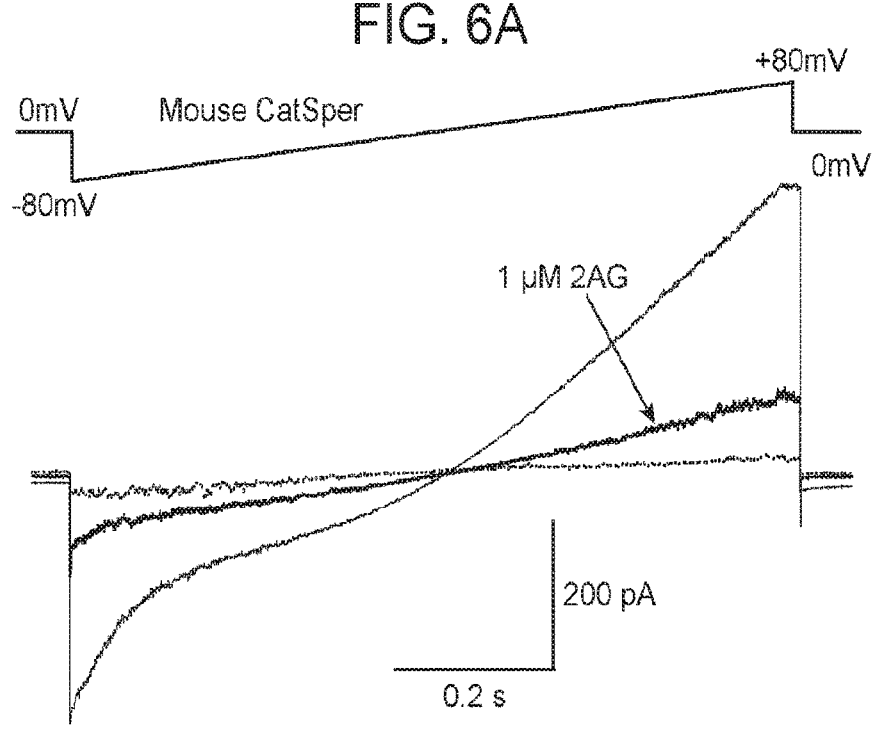

FIG. 13A

*Homo sapiens*
ABHD2 (LABH2)
SEQ ID NO:1

```
  1 mnamletpel pavfdgvkla avaavlyviv rclnlkspta ppdlyfqdsg lsrfllkscp
 61 lltkeyippl iwgksghiqt alygkmgrvr sphpyghrkf itmsdgatst fdlfeplaeh
121 cvgdditmvi cpgianhsek qvirtfvdya qkngyrcavl nhlgalpnie ltsprmftyg
181 ctwefgamvn yikktypltq lvvvgfslgg nivckylget qanqekvlcc vsvcqgysal
241 raqetfmqwd qcrrfynflm adnmkkiils hrqalfgdhv kkpqsledtd lsrlytatsl
301 mqiddnvmrk fhgynslkey yeeescmryl hriyvplmlv naaddplvhe slltipksls
361 ekrenvmfvl plhgghlgff egsvlfpepl twmdklvvey anaicqwern klqcsdteqv
421 eadle
```

Bold and underlined = transmembrane region

FIG. 13B

*Homo sapiens*; GenBank NM_007011
ABHD2 mRNA; Nucleotides 919-2196

```
 919                  at gaatgccatg ctggagactc ccgaactccc agccgtgttt
 961 gatggagtga agctggctgc agtggctgct gtgctgtacg tgatcgtccg tgtgtttgaac
1021 ctgaagagcc ccacagcccc acctgacctc tacttccagg actcggggct ctcacgcttt
1081 ctgctcaagt cctgtcctct tctgaccaaa gaatacattc caccgttgat ctggggggaaa
1141 agtggacaca tccagacagc cttgtatggg aagatgggaa gggtgaggtc gccacatcct
1201 tatgggcacc ggaagttcat cactatgtct gatggagcca ctactactt cgacctcttc
1261 gagcccttgg ctgagcactg tgttggagat gatatcacca tggtcatctg ccctggaatt
1321 gccaatcaca gcgagaagca atacatccgc actttcgttg actacgccca gaaaaatggc
1381 tatcggtgcg ccgtgctgaa ccacctgggt gccctgccca acattgaatt gacctcgcca
1441 cgcatgttca cctatggctg cacgtgggaa tttggagcca tggtgaacta catcaagaag
1501 acatatcccc tgacccagct ggtcgtcgtg gccttcagcc tgggtggtaa cattgtgtgc
1561 aaatacttgg gggagactca ggcaaaccaa gagaaggtcc tgtgctgcgt cagcgtgtgc
1621 caggggtaca gtgcactgag ggcccaggaa accttcatgc aatgggatca gtgccggcgg
1681 ttctacaact tcctcatggc tgacaacatg aagaagatca tcctctcgca caggcaagct
1741 ctttttggag accatgttaa gaaacccag agcctggaag acacggactt gagccggctc
1801 tacacagcaa catccctgat gcagattgat gacaatgtga tgaggaagtt tcacggctat
1861 aactccctga aggaatacta tgaggaagaa agttgcatgc ggtacctgca caggatttat
1921 gttcctctca tgctggttaa tgcagctgac gatccgttgg tgcatgaaag tcttctaacc
1981 attccaaaat ctctttcaga gaaacgagag aacgtcatgt ttgtgctgcc tctgcatggg
2041 ggccacttgg gcttctttga gggctctgtg ctgttccccg agcccctgac atggatggat
2101 aagctggtgg tggagtacgc caacgccatt tgccaatggg agcgtaacaa gttgcagtgc
2161 tctgacacgg agcaggtgga ggccgacctg gagtga
```

SEQ ID NO:2

SEQUENCE LISTING

```
<160> NUMBER OF SEQ ID NOS: 9

<210> SEQ ID NO 1
<211> LENGTH: 425
<212> TYPE: PRT
<213> ORGANISM: homo sapiens

<400> SEQUENCE: 1

Met Asn Ala Met Leu Glu Thr Pro Glu Leu Pro Ala Val Phe Asp Gly
1               5                   10                  15

Val Lys Leu Ala Ala Val Ala Ala Val Leu Tyr Val Ile Val Arg Cys
            20                  25                  30

Leu Asn Leu Lys Ser Pro Thr Ala Pro Pro Asp Leu Tyr Phe Gln Asp
        35                  40                  45

Ser Gly Leu Ser Arg Phe Leu Leu Lys Ser Cys Pro Leu Leu Thr Lys
    50                  55                  60
```

| | | | | | | | | | | | |
|---|---|---|---|---|---|---|---|---|---|---|---|
| Glu | Tyr | Ile | Pro | Pro | Leu | Ile | Trp | Gly | Lys | Ser | Gly | His | Ile | Gln | Thr |

Glu Tyr Ile Pro Pro Leu Ile Trp Gly Lys Ser Gly His Ile Gln Thr
65                  70                  75                  80

Ala Leu Tyr Gly Lys Met Gly Arg Val Arg Ser Pro His Pro Tyr Gly
                85                  90                  95

His Arg Lys Phe Ile Thr Met Ser Asp Gly Ala Thr Ser Thr Phe Asp
                100                 105                 110

Leu Phe Glu Pro Leu Ala Glu His Cys Val Gly Asp Ile Thr Met
            115                 120                 125

Val Ile Cys Pro Gly Ile Ala Asn His Ser Glu Lys Gln Tyr Ile Arg
130                 135                 140

Thr Phe Val Asp Tyr Ala Gln Lys Asn Gly Tyr Arg Cys Ala Val Leu
145                 150                 155                 160

Asn His Leu Gly Ala Leu Pro Asn Ile Glu Leu Thr Ser Pro Arg Met
                165                 170                 175

Phe Thr Tyr Gly Cys Thr Trp Glu Phe Gly Ala Met Val Asn Tyr Ile
                180                 185                 190

Lys Lys Thr Tyr Pro Leu Thr Gln Leu Val Val Gly Phe Ser Leu
                195                 200                 205

Gly Gly Asn Ile Val Cys Lys Tyr Leu Gly Glu Thr Gln Ala Asn Gln
210                 215                 220

Glu Lys Val Leu Cys Cys Val Ser Val Cys Gln Gly Tyr Ser Ala Leu
225                 230                 235                 240

Arg Ala Gln Glu Thr Phe Met Gln Trp Asp Gln Cys Arg Arg Phe Tyr
                245                 250                 255

Asn Phe Leu Met Ala Asp Asn Met Lys Lys Ile Ile Leu Ser His Arg
                260                 265                 270

Gln Ala Leu Phe Gly Asp His Val Lys Lys Pro Gln Ser Leu Glu Asp
                275                 280                 285

Thr Asp Leu Ser Arg Leu Tyr Thr Ala Thr Ser Leu Met Gln Ile Asp
                290                 295                 300

Asp Asn Val Met Arg Lys Phe His Gly Tyr Asn Ser Leu Lys Glu Tyr
305                 310                 315                 320

Tyr Glu Glu Glu Ser Cys Met Arg Tyr Leu His Arg Ile Tyr Val Pro
                325                 330                 335

Leu Met Leu Val Asn Ala Ala Asp Asp Pro Leu Val His Glu Ser Leu
                340                 345                 350

Leu Thr Ile Pro Lys Ser Leu Ser Glu Lys Arg Glu Asn Val Met Phe
                355                 360                 365

Val Leu Pro Leu His Gly Gly His Leu Gly Phe Phe Glu Gly Ser Val
                370                 375                 380

Leu Phe Pro Glu Pro Leu Thr Trp Met Asp Lys Leu Val Val Glu Tyr
385                 390                 395                 400

Ala Asn Ala Ile Cys Gln Trp Glu Arg Asn Lys Leu Gln Cys Ser Asp
                405                 410                 415

Thr Glu Gln Val Glu Ala Asp Leu Glu
                420                 425

<210> SEQ ID NO 2
<211> LENGTH: 979
<212> TYPE: RNA
<213> ORGANISM: homo sapiens

<400> SEQUENCE: 2
agaagccagc ggagaccccg aaccccagcc gggaggagga agcggcgcag ggcgcggcga         60

-continued

```
cggacgccgg ggaaccgaag agccccacag ccccaccgac ccacccagga ccggggccca      120
cgccgccaag ccgccccgac caaagaaaca ccaccggacg ggggaaaagg gacacaccag      180
acagccgagg gaagagggaa ggggaggcgc cacaccaggg caccggaagc acacagcgag      240
gagccaccac acgaccccga gcccggcgag cacggggaga gaacaccagg cacgcccgga      300
agccaacaca gcgagaagca aacaccgcac cggacacgcc cagaaaagg cacgggcgcc       360 ggcgaaccac cggggcccgc ccaacagaag acccgccacg cagcaccagg cgcacgggga      420
aggagccagg gaacacacaa gaagacaacc ccgacccagc ggcgcggggc cagccggggg      480
aacagggcaa aacggggag accaggcaaa ccaagagaag gccggcgcgc agcgggccag       540
gggacaggca cgagggccca ggaaacccag caagggacag gccggcggca caaccccagg      600
cgacaacaga agaagacacc ccgcacaggc aagccggaga ccagaagaaa ccccagagcc      660
ggaagacacg gacgagccgg ccacacagca acacccgagc agagagacaa ggagaggaag      720
cacggcaaac cccgaaggaa acagaggaag aaaggcagcg gaccgcacag gaagccccag      780
cggaagcagc gacgaccggg gcagaaagcc aaccaccaaa acccagagaa acgagagaac      840
gcagggcgcc cgcaggggc cacgggccga gggccggcgc cccgagcccc gacaggagga       900
aagcgggggg agacgccaac gccagccaag ggagcgaaca aggcaggccg cacggagca       960 ggggaggccg accggagga                                                   979
```

<210> SEQ ID NO 3
<211> LENGTH: 16
<212> TYPE: RNA
<213> ORGANISM: artificial sequence
<220> FEATURE:
<223> OTHER INFORMATION: synthetic RNA

<400> SEQUENCE: 3

```
cggacacgcc cagaaa                                                       16
```

<210> SEQ ID NO 4
<211> LENGTH: 16
<212> TYPE: RNA
<213> ORGANISM: artificial sequence
<220> FEATURE:
<223> OTHER INFORMATION: synthetic RNA

<400> SEQUENCE: 4

```
acgaccgggg cagaaa                                                       16
```

<210> SEQ ID NO 5
<211> LENGTH: 18
<212> TYPE: DNA
<213> ORGANISM: artificial sequence
<220> FEATURE:
<223> OTHER INFORMATION: Synthetic Primer

<400> SEQUENCE: 5

```
atgaatgcca tgctggag                                                     18
```

<210> SEQ ID NO 6
<211> LENGTH: 17
<212> TYPE: DNA
<213> ORGANISM: artificial sequence
<220> FEATURE:
<223> OTHER INFORMATION: Synthetic Primer

<400> SEQUENCE: 6

```
agagtccgga ggcctca                                                      17
```

```
<210> SEQ ID NO 7
<211> LENGTH: 19
<212> TYPE: PRT
<213> ORGANISM: artificial sequence
<220> FEATURE:
<223> OTHER INFORMATION: Synthetic peptide

<400> SEQUENCE: 7

Lys Ser Pro Thr Ala Pro Pro Asp Leu Tyr Phe Gln Asp Ser Gly Leu
1               5                   10                  15

Ser Arg Phe

<210> SEQ ID NO 8
<211> LENGTH: 40
<212> TYPE: PRT
<213> ORGANISM: artificial sequence
<220> FEATURE:
<223> OTHER INFORMATION: Synthetic peptide

<400> SEQUENCE: 8

Arg Arg Thr Ala Arg Gly Ala Val Val Arg Ala Arg Glu Leu Ala Pro
1               5                   10                  15

Glu Ala Val Leu Phe Thr Tyr Val Gly Lys Ala Arg Leu Asp Pro Thr
            20                  25                  30

Val Pro Pro Leu Pro Phe Arg Glu
        35                  40

<210> SEQ ID NO 9
<211> LENGTH: 14
<212> TYPE: PRT
<213> ORGANISM: artificial sequence
<220> FEATURE:
<223> OTHER INFORMATION: Synthetic peptide

<400> SEQUENCE: 9

Arg Ser Pro Ile Asp Thr Phe Pro Thr Asp Pro Ile Lys Glu
1               5                   10
```

COMPOSITIONS AND METHODS FOR MODULATING ABHD2 ACTIVITY

CROSS-REFERENCE

This application claims the benefit of U.S. Provisional Patent Application No. 62/200,292, filed Aug. 3, 2015, which application is incorporated herein by reference in its entirety.

STATEMENT REGARDING FEDERALLY SPONSORED RESEARCH

This invention was made with government support under Grant Numbers GM111802, HD068914, HD081403, and RR025622 awarded by The National Institutes of Health. The government has certain rights in the invention.

INTRODUCTION

Steroid hormones control vital organism functions such as development, metabolism, inflammation, ion homeostasis, and reproduction. According to the conventional model of steroid signaling, these functions are regulated through the interaction of steroid hormones to their corresponding genomic receptor to alter gene expression. The timescale of such events ranges from several hours to days. However, there is another, much faster response that is also triggered by steroid hormones in a separate "non-genomic" manner that is poorly understood. This unconventional non-genomic signaling happens on a timescale of seconds and plays an important role in modulation of pain perception by dorsal root ganglion neurons, and in oocyte maturation, and is vital for human sperm cell activation.

The steroid hormone progesterone (P4) is a major component of follicular fluid and is released by ovaries and cumulus cells surrounding the oocyte. At nanomolar concentrations, P4 is known to cause rapid and robust elevation of sperm cytoplasmic calcium levels through binding to a non-genomic receptor. This rise in intracellular $[Ca^{2+}]$ leads to changes in sperm motility known as hyperactivation and primes the cell for acrosomal exocytosis. It is also proposed that through this rapid signaling mechanism, P4 can serve as a sperm chemoattractant. A critical step in sperm cell activation is a massive P4-mediated calcium influx through a calcium channel CatSper.

SUMMARY

The present disclosure provides compositions and methods of modulating abhydrolase domain-containing protein-2 (ABHD2). The present disclosure provides methods of identifying agents that modulate ABHD2 activity.

BRIEF DESCRIPTION OF THE DRAWINGS

FIG. 1A-1D depict activation of human CatSper channel by Progesterone (P4) and its synthetic analog P4*. FIG. 1D provides the following sequences: KSPTAPPD-LYFQDSGLSRF (SEQ ID NO:7); RRTARGAVVRARE-LAPEAVLFTYVGKARLDPTVPPLPFRE (SEQ ID NO:8); RSPIDTFPTDPIKE (SEQ ID NO:9).

FIG. 2A-2D depict use of P4* in identifying sperm progesterone binding proteins.

FIG. 5A-5E depict the effect of endogenous cannabinoids on CatSper current.

FIG. 6A-6E depict the effect of endogenous cannabinoids on mammalian CatSper.

FIG. 13A-13B provide an amino acid sequence (FIG. 13A) of a human ABHD2 (SEQ ID NO:1), and a nucleotide sequence (FIG. 13B) encoding the human ABHD2 (SEQ ID NO:2).

DEFINITIONS

Figure 2A:
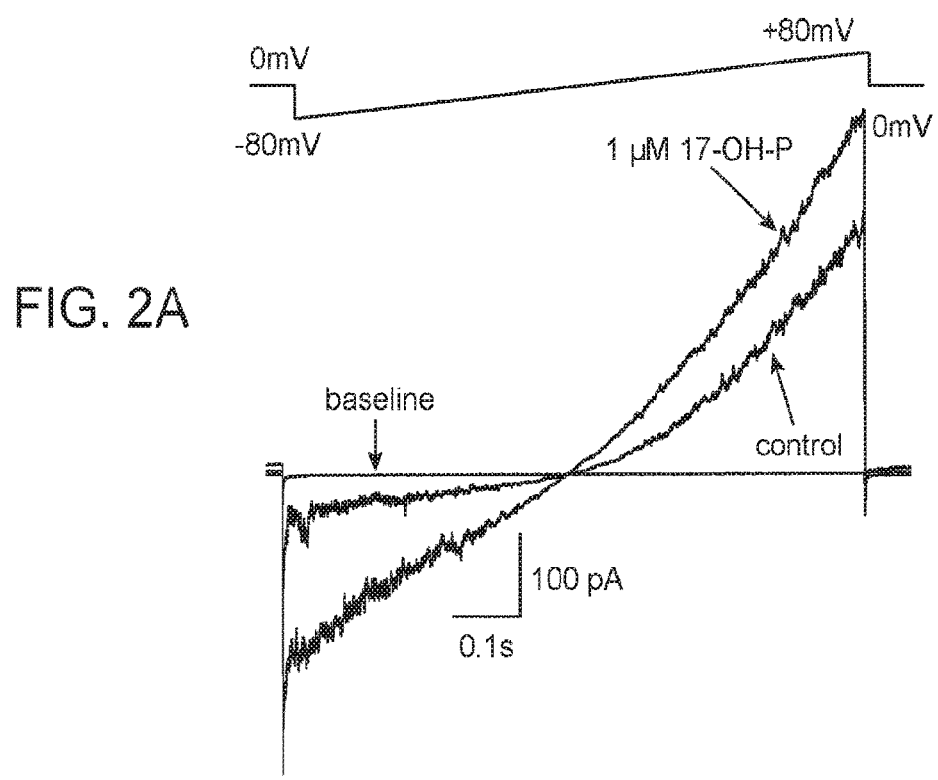

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, bi-specific antibodies, multi-specific antibodies, and fusion proteins comprising an antigen-binding (also referred to herein as antigen binding) portion of an antibody and a non-antibody protein. The antibodies can be detectably labeled, e.g., with a radioisotope, an enzyme that generates a detectable product, a fluorescent protein, and the like. The antibodies can be further conjugated to other moieties, such as members of specific binding pairs, e.g., biotin (member of biotin-avidin specific binding pair), and the like. The antibodies can also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

The term "humanized immunoglobulin" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

For example, humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); domain antibodies (dAb; Holt et al. (2003) Trends Biotechnol. 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab)$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$—$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) Proc. Natl. Acad. Sci. USA 90:6444-6448.

As used herein, the term "affinity" refers to the equilibrium constant for the reversible binding of two agents (e.g., an antibody and an antigen) and is expressed as a dissociation constant ($K_D$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution.

The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. For example, as described below, an agent suitable for use in inhibiting an activity of an ABHD2 antibody can be an antibody that specifically binds an ABHD2 polypeptide. "Specific binding" refers to binding with an affinity of at least about $10^{-7}$ M or greater, e.g., $5 \times 10^{-7}$ M, $10^{-8}$M, $5 \times 10^{-8}$M, and greater. "Non-specific binding" refers to binding with an affinity of less than about $10^{-7}$ M, e.g., binding with an affinity of $10^{-6}$ M, $10^{-5}$ M, $10^{-4}$ M, etc.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease. In some cases, "treating" refers to inhibiting conception.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of an agent that, when administered to a mammal, is sufficient to effect a treatment (e.g., treatment of a disease; contraception; etc.). The "therapeutically effective amount" will vary depending on the agent, the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an ABHD2 polypeptide" includes a plurality of such polypeptides and reference to "the acylglycerol" includes reference to one or more acylglycerols and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions and methods of modulating abhydrolase domain-containing protein-2 (ABHD2). The present disclosure provides methods of identifying agents that modulate ABHD2 activity. The inventors have identified ABHD2 as a P4 non-genomic receptor. Modulating levels and/or activity of ABHD2 provides for regulation of non-genomic steroid signaling in various tissues. A "non-genomic" receptor refers to a receptor that does not directly and initially influence gene expression. See, e.g., Losel and Wehling (2003) *Nat. Rev. Mol. Cell Biol.* 4:46.

Methods of Modulating ABHD2 Activity and/or Levels in a Cell

The present disclosure provides a method of modulating the level and/or activity of an ABHD2 polypeptide in a cell, the method comprising contacting the cell with an agent that modulates the level and/or activity of the ABHD2 polypeptide. The present disclosure provides a method of reducing the level and/or activity of an ABHD2 polypeptide in a cell, the method comprising contacting the cell with an agent that reduces the level and/or activity of the ABHD2 polypeptide. The present disclosure provides a method of increasing the level and/or activity of an ABHD2 polypeptide in a cell, the method comprising contacting the cell with an agent that increases the level and/or activity of the ABHD2 polypeptide.

Agents that can reduce the level and/or activity of an ABHD2 polypeptide in a cell include, e.g., an antibody that specifically binds an ABHD2 polypeptide; a serine hydrolase inhibitor that specifically inhibits ABHD2; a nucleic acid that specifically reduces the level of ABHD2 in the cell (e.g., an antisense nucleic acid; an Shh nucleic acid; and the like); and a fragment of the extracellular domain of the ABHD2 polypeptide. ABHD2 levels can also be reduced via targeted genome editing, using, e.g., a targeted genome editing system such as CRISPR/Cas9.

Agents that increase the level and/or activity of an ABHD2 polypeptide in a cell include, e.g., an ABHD2 polypeptide (including active fragments of an ABHD2 polypeptide); a nucleic acid comprising a nucleotide sequence encoding an ABHD2 polypeptide; progesterone; P4* (as shown in FIG. 2C); P4* (as shown in FIG. 2C) without the biotin tag; P4* (as shown in FIG. 2C) without the biotin tag and without the poly(ethylene glycol); and the like. A nucleic acid comprising a nucleotide sequence encoding an ABHD2 polypeptide can be a recombinant expression vector comprising a nucleotide sequence encoding an ABHD2 polypeptide. In some cases, the nucleotide sequence encoding the ABHD2 polypeptide is operably linked to a promoter that is active in, e.g., a dorsal root ganglion (DRG) cell; for example, in some cases, the promoter selectively drives expression in a DRG cell (e.g., a beta-galactoside alpha1, 2-fucosyltransferase gene promoter (see, e.g., Hitoshi et al. (1999) *J. Biol. Chem.* 274:389)). In some cases, the nucleotide sequence encoding the ABHD2 polypeptide is operably linked to a promoter that is active in a lung cell; for example, in some cases, the promoter selectively drives expression in a lung cell (e.g., a lung-specific surfactant protein B gene promoter (see, e.g., Bohinski et al. (1994) *Mol. Cell Biol.* 14:5671); a surfactant protein C promoter (see, e.g., Gou et al. (2004) *Nucl. Acids Res.* 32:e134). In some cases, the nucleic acid is introduced into the genome of the cell via homology-directed DNA repair; for example, a CRISPR/Cas9 system can be used, together with a nucleic acid comprising a nucleotide sequence encoding an ABHD2 polypeptide, to introduce the nucleic acid into the genome of a cell.

In some cases, the cell is a sperm cell. Thus, the present disclosure provides a method of reducing the level and/or activity of an ABHD2 polypeptide in a sperm cell, the method comprising contacting the sperm cell with an agent that reduces the level and/or activity of the ABHD2 polypeptide.

In some cases, an agent that reduces the level and/or activity of an ABHD2 polypeptide reduces sperm motility by at least 15%, at least 20%, at least 25%, at least 30%, at least 40%, at least 50%, at least 75%, or more than 75%, compared to the motility of the sperm in the absence of the agent.

In some cases, the cell is a dorsal root ganglion (DRG). Thus, the present disclosure provides a method of increasing the level and/or activity of an ABHD2 polypeptide in a DRG cell, the method comprising contacting the DRG cell with an agent that increases the level and/or activity of the ABHD2 polypeptide.

In some cases, the cell is a lung cell. Thus, the present disclosure provides a method of increases the level and/or activity of an ABHD2 polypeptide in a lung cell, the method comprising contacting the lung cell with an agent that increases the level and/or activity of the ABHD2 polypeptide.

Antibodies

In some cases, the agent is an antibody that specifically binds an ABHD2 polypeptide. Thus, the present disclosure provides a method of reducing the level and/or activity of an ABHD2 polypeptide in a cell, the method comprising contacting the cell with an antibody that specifically binds an ABHD2 polypeptide and that reduces the activity of the ABHD2 polypeptide.

In some cases, an antibody that specifically binds an ABHD2 polypeptide reduces binding of P4 to the ABHD2 polypeptide. For example, in some cases, an antibody that specifically binds an ABHD2 polypeptide reduces binding of P4 to the ABHD2 polypeptide by at least 15%, at least 20%, at least 25%, at least 30%, at least 40%, at least 50%, at least 75%, or more than 75%, compared to the level of binding of P4 to the ABHD2 polypeptide in the absence of the anti-ABHD2 antibody.

In some cases, an antibody that specifically binds an ABHD2 polypeptide reduces hydrolysis of acylglycerols by the ABHD2 polypeptide. For example, in some cases, an antibody that specifically binds an ABHD2 polypeptide reduces hydrolysis of an acylglycerol by the ABHD2 polypeptide by at least 15%, at least 20%, at least 25%, at least 30%, at least 40%, at least 50%, at least 75%, or more than 75%, compared to the level of hydrolysis of the acylglycerol by the ABHD2 polypeptide in the absence of the anti-ABHD2 antibody.

In some cases, the anti-ABHD2 antibody is a monoclonal antibody. In some cases, the anti-ABHD2 antibody is a humanized monoclonal antibody. In some cases, the anti-ABHD2 antibody is an antibody fragment, e.g., an scFv, a Fab fragment, and the like.

Fragments of the Extracellular Domain of an ABHD2 Polypeptide

In some cases, an agent that reduces the activity of an ABHD2 polypeptide is a fragment of the extracellular domain (ECD) of an ABHD2 polypeptide. In some cases, the agent comprises an amino acid sequence having at least 80%, at least 85%, at least 90%, at least 95%, at least 98%, at least 99%, or 100%, amino acid sequence identity to a contiguous stretch of from about 25 amino acids (aa) to 395 aa (e.g., from about 25 aa to about 50 aa, from about 50 aa to about 75 aa, from about 75 aa to about 100 aa, from about 100 aa to about 150 aa, from about 150 aa to about 200 aa, from about 200 aa to about 250 aa, from about 250 aa to about 300 aa, from about 300 aa to about 350 aa, or from 350 aa to 395 aa) of amino acids 31-425 of the amino acid sequence set forth in SEQ ID NO:1 and depicted in FIG. 13A. In some cases, the agent comprises an amino acid sequence having at least 80%, at least 85%, at least 90%, at least 95%, at least 98%, at least 99%, or 100%, amino acid sequence identity to a contiguous stretch of from about 25 amino acids (aa) to 395 aa (e.g., from about 25 aa to about 50 aa, from about 50 aa to about 75 aa, from about 75 aa to about 100 aa, from about 100 aa to about 150 aa, from about 150 aa to about 200 aa, from about 200 aa to about 250 aa, from about 250 aa to about 300 aa, from about 300 aa to about 350 aa, or from 350 aa to 395 aa) of amino acids 31-425 of the amino acid sequence set forth in SEQ ID NO:1 and depicted in FIG. 13A; and has a length of from about 25 aa to about 50 aa, from about 50 aa to about 75 aa, from about 75 aa to about 100 aa, from about 100 aa to about 150 aa, from about 150 aa to about 200 aa, from about 200 aa to about 250 aa, from about 250 aa to about 300 aa, from about 300 aa to about 350 aa, or from 350 aa to 395 aa.

Serine Hydrolase Inhibitors

In some cases, the agent is a serine hydrolase (SH) inhibitor that specifically inhibits enzymatic activity of an ABHD2 polypeptide. For example, in some cases, the SH inhibitor is methyl arachidonyl fluorophosphates (MAFP). Inhibition of enzymatic activity of an ABHD2 polypeptide refers to inhibition of hydrolysis of acylglycerol, e.g., hydrolysis of 2-arachidonoylglycerol (2-AG) and/or 1-arachidonoylglycerol (1-AG).

Interfering Nucleic Acids

Suitable agents that reduce the level of an ABHD2 gene product (e.g., an ABHD2 polypeptide; an ABHD2 mRNA) in a cell include interfering nucleic acids, e.g., interfering RNA molecules. In one embodiment, reduction of an ABHD2 gene product level is accomplished through RNA interference (RNAi) by contacting a cell with a small nucleic acid molecule, such as a short interfering nucleic acid (siNA), an antisense RNA, a short interfering RNA (siRNA), a double-stranded RNA (dsRNA), a micro-RNA (miRNA), or a short hairpin RNA (shRNA) molecule, or modulation of expression of a small interfering RNA (siRNA) so as to provide for decreased levels of an ABHD2 gene product.

Non-limiting examples of siRNAs that reduce the level of ABHD2 include, e.g.: 1) TTCGTTGAC-TACGCCCAGAAA (SEQ ID NO:3); and 2) ACGATCCGTTGGTGCATGAAA (SEQ ID NO:4).

Interfering nucleic acids can be designed based on the nucleotide sequence of an ABHD2-encoding nucleotide sequence. For example, in some embodiments, an ABHD2-encoding nucleotide sequence as set forth in FIG. 13B, or a nucleotide sequence having at least 90%, at least 95%, at least 98%, or at least 99%, nucleotide sequence identity to the ABHD2 nucleotide sequence depicted in FIG. 13B, is used to design an interfering nucleic acid.

The terms "double stranded RNA," "dsRNA," "partial-length dsRNA," "full-length dsRNA," "synthetic dsRNA," "in vitro produced dsRNA," "in vivo produced dsRNA," "bacterially produced dsRNA," "isolated dsRNA," and "purified dsRNA" as used herein refer to nucleic acid molecules capable of being processed to produce a smaller nucleic acid, e.g., a short interfering RNA (siRNA), capable of inhibiting or down regulating gene expression, for example by mediating RNA interference "RNAi" or gene silencing in a sequence-specific manner. Design of a dsRNA or a construct comprising a dsRNA targeted to a gene of interest is routine in the art, see e.g., Timmons et al. (2001) Gene, 263:103-112; Newmark et al. (2003) Proc Natl Acad Sci USA, 100 Supp 1:11861-5; Reddien et al. (2005) Developmental Cell, 8:635-649; Chuang & Meyerowitz (2000) Proc Natl Acad Sci USA, 97:4985-90; Piccin et al. (2001) Nucleic Acid Res, 29:E55-5; Kondo et al. (2006) Genes Genet Syst, 81:129-34; and Lu et al. (2009) FEBS J, 276:3110-23; the disclosures of which are incorporated herein by reference.

dsRNA may be produced de novo or may be produced from "dsRNA templates", i.e., nucleic acid templates for generating a dsRNA targeted to a particular gene. A dsRNA template or a construct for generating a dsRNA targeted to a particular gene are obtained by any convenient method and need not necessarily be comprised of RNA, e.g., a dsRNA template may be DNA, e.g., single stranded DNA or double stranded DNA. dsRNA templates may be obtained by generating a copy of a naturally occurring spliced mRNA, e.g., a cDNA, using molecular techniques, e.g., reverse transcription or first strand synthesis. dsRNA templates may also be obtained by producing a copy of the coding region, e.g. the CDS, of a gene sequence obtained from sequencing data, e.g., publicly available databases of transcriptome and genomic sequences (see e.g., genomic information from the National Center for Biotechnology Information (NCBI) available on the internet at www(dot)ncbi(dot)nlm(dot)nih (dot)gov/genome/browse/; transcriptome information at the Exon Bioinformatics for Discovery available at http://exon (dot)niaid(dot)nih(dot)gov/transcriptome(dot)html; Zeng & Extavour (2012) Database, bas048; and Wurm et al. (2009) BMC Genomics, 10:5, the disclosures of which are incorporated herein by reference), de novo sequencing of isolated nucleic acid, predicted gene sequences generated by gene prediction software (e.g., ATGpr, AUGUSTUS, BGF, DIO-GENES, Dragon Promoter Finder, EUGENE, FGENESH, FRAMED, GENIUS, geneid, GENEPARSER, GeneMark, GeneTrack, GENOMESCAN, GENSCAN, GLIMMER, GLIMMERHMM, GrainEXP, MORGAN, NIX, NNPP, NNSPLICE, ORF FINDER, Regulatory Sequence Analysis Tool, SPLICEPREDICTOR, VEIL, and the like), and the like. Such first and iterative copies of dsRNA templates may represent the same sequence, e.g., the same sequence in the same 5' to 3' orientation as the sequence from which the copy was generated, or may represent the complement, the reverse, or the reverse complement of the sequence from which the copy was generated as methods for producing subsequent copies or modifying sequence orientation are well known in the art. In certain instances, a mRNA or a coding region of a gene is constructed from the genomic locus of a gene by assembly of all or some, e.g., about 1 or more, about 2 or more, about 3 or more, about 4 or more, about half, more than half, about 75% or more, about 80% or more, about 90% or more, of the exons of the genetic locus into a synthetic mRNA sequence or synthetic cDNA sequence and the resulting sequence is used to generate synthetic mRNA or synthetic cDNA. Assembly of exons of a genetic locus is routine in the art and can performed by identifying exon-intron junctions either manually or with the help of software that identifies exon-intron junctions either automatically or through user input.

In certain instances, the dsRNA template is a full-length dsRNA template and therefore the dsRNA generated from the template is a full-length dsRNA. By "full-length dsRNA" is meant a dsRNA that comprises the full length sequence of a gene, e.g., all of the coding exons of a gene, all of the coding exons of a gene including 5' or 3' untranslated regions of a gene, all of a gene sequence contained between the start codon of a gene and the stop codon of the same gene, etc. In other cases, the dsRNA template is a full-length dsRNA template but is used only to generate a partial-length dsRNA. By partial dsRNA is meant any dsRNA of a gene that contains fewer than all of the coding exons of a gene, e.g., all of a gene except for a portion of an exon, all of a gene except one exon of the gene, all of a gene except more than one exon of a gene, all of a gene except more than two exons of a gene, all of a gene except more than three exons of a gene, all of a gene except more than four exons of a gene, or all of a gene except more than five exons of a gene. Partial-length dsRNA may also represent a dsRNA that includes only a percent portion of the full-length dsRNA of a particular gene but retains the function of activating gene specific silencing by RNAi, e.g., about 95%, about 90%, about 80%, about 70%, about 60%, about 50%, about 40%, about 30%, about 20%, about 10%, about 5%, about 3%, about 2%, about 1%, about, or less than 1% of a full-length dsRNA of a particular gene. In still other instances a partial-length dsRNA template is used to generate a partial-length dsRNA, i.e., partial-length dsRNA is generated from a partial gene sequence or clone and need not be generated from a full-length sequence or clone.

In certain instances, a dsRNA template is cloned, with or without alteration of the dsRNA template sequence, and cloned or inserted into a vector, e.g., a plasmid or phage DNA, to generate a dsRNA construct. By "alteration of the dsRNA templates sequence" is meant that the dsRNA template sequence is modified either directly by introducing mutations, e.g., point mutations, insertions, deletions, silent mutations, and the like, to the original dsRNA template sequence obtained. Alteration of the dsRNA template sequence may result in a mutated dsRNA template sequence that shares about 95%, about 90%, about 80%, about 70%, about 60%, about 50%, or less than about 50% homology with the original dsRNA template sequence. In other instances, the original dsRNA template sequence obtained may be left unmutated or not mutated and one or more nucleotides may be attached to the ends of the original dsRNA template sequence, or some combination therein. In certain instances, an unmutated dsRNA template is amended with additional nucleotides that contain functional sequences, i.e., sequences that may be used for downstream applications of the dsRNA template, e.g., enzyme recognition sites including polymerase recognition sites or endonuclease recognition sites or recombination sites. Methods of nucleic acid cloning and transform which find use in cloning and transforming dsRNA templates are known in the art; see, e,g., Fire et al. (1990) *Gene*, 93:189-198; Timmons et al. (2001) *Gene*, 263:103-112; Newmark et al. (2003) *Proc Natl Acad Sci USA*, 100 Supp 1:11861-5; Reddien et al. (2005) *Developmental Cell*, 8:635-649; Chuang & Meyerowitz (2000) *Proc Natl Acad Sci USA*, 97:4985-90; Piccin et al. (2001) *Nucleic Acid Res*, 29:E55-5; and Kondo et al. (2006) *Genes Genet Syst*, 81:129-34; the disclosures of which are incorporated herein by reference.

In some embodiments, the dsRNA template, e.g., dsRNA template inserted into a vector, is transformed into a host cell specifically designed for the production of dsRNA. In certain instances, a dsRNA construct, e.g., a cloned dsRNA or a cloned dsRNA template that has been introduced into a vector, e.g., a plasmid or phage DNA, is used to generate dsRNA. dsRNA constructs, e.g., dsRNA plasmid constructs, may be used to generate in vitro transcribed dsRNA through the use of an in vitro transcription reaction, e.g., through the use of an in vitro transcription kit or a dsRNA synthesis kit, non-limiting examples of commercially available in vitro transcription kits and dsRNA synthesis kit include MEGAscript® RNAi Kits (Life Technologies, Grand Island, N.Y.), Replicator RNAi Kits (Thermo Scientific®, a division of Fisher Scientific®, Pittsburgh, Pa.), T7 RiboMAX™ (Promega Corporation, Madison, Wis.), MAXIscript® (Life Technologies, Grand Island, N.Y.), T7 High Yield RNA Synthesis Kit (New England Biolabs, Ipswich, Mass.), SP6/T7 Transcription Kit (Roche Applied Science, Indianapolis, Ind.), and the like.

In some instances, nucleic acids of the instant disclosure, e.g., nucleic acid templates, interfering nucleic acids (e.g., dsRNA), etc., and nucleic acid reagents including those synthetically or recombinantly produced, may be obtained from one or more commercial suppliers or commercial custom synthesis companies, including but not limited to e.g., IBA GmbH (Goettingen, Germany), Eurofins Genomics (Ebersberg, Germany), tebu-bio (Le Perray-en-Yvelines, France), Sigma-Aldrich (St Louis, Mo.), Ambion (Austin, Tex.), Applied Biosystems (Foster City, Calif.), Avecia OligoMedicines (Milford, Mass.), BioCat (Heidelberg, Germany), BioSpring (Frankfurt, Germany), Exiqon (Vedbaek, Denmark), GenScript (Piscataway, N.J.), Gene Tools (Philomath, Oreg.), Imgenex (San Diego, Calif.), Integrated DNA Technologies (Coralville, Iowa), Life Technologies (Grand Island, N.Y.), MWG-Biotech (Ebersberg, Germany), Oligoengine (Seattle, Wash.), QIAGEN (Germantown, Md.), SABiosciences (Frederick, Md.), Sigma-Genosys (The Woodlands, Tex.), and the like.

The term "short interfering nucleic acid," "siNA," "short interfering RNA," "siRNA," "short interfering nucleic acid molecule," "short interfering oligonucleotide molecule," or "chemically-modified short interfering nucleic acid molecule," as used herein refers to any nucleic acid molecule capable of inhibiting or down regulating gene expression, for example by mediating RNA interference "RNAi" or gene silencing in a sequence-specific manner Design of RNAi molecules when given a target gene is routine in the art. See also US 2005/0282188 (which is incorporated herein by reference) as well as references cited therein. See, e.g., Pushparaj et al. Clin Exp Pharmacol Physiol. 2006 May-June; 33(5-6):504-10; Lutzelberger et al. Handb Exp Pharmacol. 2006; (173):243-59; Aronin et al. Gene Ther. 2006 March; 13(6):509-16; Xie et al. Drug Discov Today. 2006 January; 11(1-2):67-73; Grunweller et al. Curr Med Chem. 2005; 12(26):3143-61; and Pekaraik et al. Brain Res Bull. 2005 Dec. 15; 68(1-2):115-20. Epub 2005 Sep. 9. RNAi molecules include antisense nucleic acids and siNA. The discussion, below, that relates to siNA can apply, where appropriate, to antisense nucleic acids.

Methods for design and production of siNAs to a desired target are known in the art, and their application to ABHD2 genes for the purposes disclosed herein will be readily apparent to the ordinarily skilled artisan, as are methods of production of siRNAs having modifications (e.g., chemical modifications) to provide for, e.g., enhanced stability, bioavailability, and other properties to enhance use as therapeutics. In addition, methods for formulation and delivery of siNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US2002/0120129, each of which are incorporated herein by reference.

Publicly available tools to facilitate design of siRNAs are available in the art. See, e.g., DEQOR: Design and Quality Control of RNAi (available on the internet at cluster-1.mpi-cbg.de/Deqor/deqor.html). See also, Henschel et al. Nucleic Acids Res. 2004 Jul. 1; 32(Web Server issue):W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand generally comprises nucleotide sequence that is complementary to nucleotide sequence in the other strand; such as where the antisense strand and sense strand form a duplex or double stranded structure, for example wherein the double stranded region is about 15 base pairs to about 30 base pairs, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 nucleotides to about 25 or more nucleotides of the siNA molecule are complementary to the target nucleic acid or a portion thereof).

Alternatively, the RNAi can be assembled from a single oligonucleotide, where the self-complementary sense and antisense regions of the siNA are linked by a nucleic acid-based or non-nucleic acid-based linker(s). The RNAi can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The RNAi can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563-574 and Schwarz et al., 2002, Molecular Cell, 10, 537-568), or 5',3'-diphosphate.

In certain embodiments, the RNAi molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the RNAi molecule interacts with nucleotide sequence of a target gene in a manner that causes inhibition of expression of the target gene.

As used herein, RNAi molecules need not be limited to those molecules containing only RNA, but further encompasses chemically-modified nucleotides and non-nucleotides. In certain embodiments, the short interfering nucleic acid molecules lack 2'-hydroxy (2'-OH) containing nucleotides. RNAi molecules (e.g., siNA) do not necessarily require the presence of nucleotides having a 2'-hydroxy group for mediating RNAi and as such, RNAi molecules optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules can be used to epigenetically silence a target gene at the post-transcriptional level and/or the pre-transcriptional level. In a non-limiting example, epigenetic regulation of gene expression by siNA molecules can result from siNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

siNA molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178). The multifunctional siNA can comprise sequence targeting, for example, two regions of a target nucleic acid.

siNA molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334, 711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Eamshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; each of which are hereby incorporated in their totality by reference herein). In view of such teachings, similar modifications can be used as described herein to modify the siNA nucleic acid molecules of disclosed herein so long as the ability of siNA to promote RNAi is cells is not significantly inhibited.

Short interfering nucleic acid (siNA) molecules having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, Nucleic Acids Res. 23, 2677; Caruthers et al., 1992, Methods in Enzymology 211, 3-19, incorporated by reference herein. In one embodiment, nucleic acid molecules include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al. 1998, J. Am. Chem. Soc., 120, 8531-8532). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., WO 00/66604 and WO 99/14226).

siNA molecules can be provided as conjugates and/or complexes, e.g., to facilitate delivery of siNA molecules into a cell. Exemplary conjugates and/or complexes includes those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine) In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

The present disclosure further provides a nucleic acid (including an expression vector) that comprises a nucleotide sequence that encodes a subject nucleic acid agent (e.g., an antisense; an siNA; etc.). Suitable expression vectors include, e.g., a viral vector. In some embodiments, the nucleic acid agent-encoding nucleotide sequence is operably linked to a keratinocyte-specific promoter. In some embodiments, the nucleic acid agent-encoding nucleotide sequence is operably linked to an inducible promoter. In the discussion herein relating to compositions comprising, and methods involving use of, a nucleic acid agent, it should be understood that the present disclosure contemplates compositions comprising a nucleic acid comprising a nucleotide sequence that encodes a subject nucleic acid agent, and methods involving use of a nucleic acid comprising a nucleotide sequence that encodes a subject nucleic acid agent.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Modifications

In some embodiments, a subject nucleic acid (e.g., an siRNA; an antisense nucleic acid) comprises one or more modifications, e.g., a base modification, a backbone modification, etc. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Backbones and Modified Internucleoside Linkages

Examples of suitable modifications include modified backbones or non-natural internucleoside linkages. Nucleic acids (e.g., a subject siRNA; a subject antisense nucleic acid) having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid (e.g., a subject siRNA; a subject antisense nucleic acid) comprises one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids (e.g., a subject siRNA; a subject antisense nucleic acid) having morpholino backbone structures as described in, e.g., U.S. Pat. No. 5,034,506. For example, in some embodiments, a subject nucleic acid (e.g., a subject antisense nucleic acid; a subject synthetic target protector nucleic acid) comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A subject nucleic acid (e.g., a subject siRNA; a subject antisense nucleic acid) can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A subject nucleic acid (e.g., a subject siNA; a subject antisense nucleic acid) can also include one or more substituted sugar moieties. Suitable polynucleotides comprise a sugar substituent group selected from: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy $CH_2$ $CH_2$ $CH_2NH_2$), allyl (—$CH_2$—CH=$CH_2$), —O-allyl $CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid (e.g., a subject siRNA; a subject antisense nucleic acid) may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound (e.g., an antisense nucleic acid; a target protector nucleic acid). These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Conjugates

Another possible modification of a subject nucleic acid (e.g., a subject siRNA; a subject antisense nucleic acid) involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject antisense nucleic acid or target protector nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937.

Treatment Methods

The present disclosure provides compositions and treatment methods. Treatment methods include methods of inhibiting conception (e.g., by reducing the activity and/or level of an ABHD2 polypeptide in a sperm cell). Treatment methods include methods of reducing pain (e.g., by increasing the activity and/or level of an ABHD2 polypeptide in a DRG cell).

The present disclosure provides a method of inhibiting conception in an individual, the method comprising administering to the individual an effective amount an agent that reduces the level and/or activity of an ABHD2 polypeptide in the individual.

In some cases, an effective amount of an agent that specifically reduces the level and/or activity of an ABHD2 polypeptide in an individual (e.g., in a sperm cell in the individual) is an amount that, when administered in one or more doses to an individual in need thereof, as monotherapy or in combination therapy, is effective to inhibit sperm activity (e.g., motility) by at least about 10%, at least about 20%, at least about 30%, at least about 40%, at least about 50%, or more than 50%, compared to the sperm activity (e.g., motility) in the individual in the absence of treatment with the agent. Suitable agents are described above. In some cases, the agent is a nucleic acid agent. In some cases, the nucleic acid agent is an antisense nucleic acid. In some cases, the nucleic acid agent is an siRNA, e.g., a short interfering RNA. In some cases, the nucleic acid agent is an antisense nucleic acid agent. In some cases, the agent is an antibody, as described above. In some cases, the agent is a fragment of the ECD of an ABHD2 polypeptide, as described above. In some cases, the agent is an SH inhibitor, as described above.

In some cases, an effective amount of an agent that specifically increases the level and/or activity of an ABHD2 polypeptide in an individual (e.g., in a DRG cell in the individual) is an amount that, when administered in one or more doses to an individual in need thereof, as monotherapy or in combination therapy, is effective to reduce pain in the individual by at least about 10%, at least about 20%, at least about 30%, at least about 40%, at least about 50%, or more than 50%, compared to the level of pain in the individual in the absence of treatment with the agent. Suitable agents are described above. In some cases, the agent is a nucleic acid agent, e.g., a nucleic acid (e.g., an expression vector) comprising a nucleotide sequence encoding an ABHD2 polypeptide. In some cases, the agent is an ABHD2 polypeptide.

Compositions and Formulations

The present disclosure provides compositions, e.g., pharmaceutical compositions, comprising an agent that reduces the level and/or activity of an ABHD2 polypeptide in a cell.

The present disclosure provides compositions, e.g., pharmaceutical compositions, comprising an agent that increases the level and/or activity of an ABHD2 polypeptide in a cell. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A subject composition can include: a) an agent that reduces the level and/or activity of an ABHD2 polypeptide in a cell, or an agent that increases the level and/or activity of an ABHD2 polypeptide in a cell; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl) amino-tris(hydroxymethyl)methane (BIS-Tris), N-(2-hydroxyethyl)piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris(hydroxymethyl)-aminomethane (Tris), etc.). Suitable salts include, e.g., NaCl, $MgCl_2$, KCl, $MgSO_4$, etc.

A subject pharmaceutical formulation can include an agent that reduces the level and/or activity of an ABHD2 polypeptide in a cell, or an agent that increases the level and/or activity of an ABHD2 polypeptide in a cell, where the agent is present in an amount of from about 0.001% to about 90% (w/w). In the description of formulations, below, "agent" will be understood to include an agent that reduces the level and/or activity of an ABHD2 polypeptide in a cell, and an agent that increases the level and/or activity of an ABHD2 polypeptide in a cell.

An agent (e.g., an agent that reduces the level and/or activity of an ABHD2 polypeptide in a cell; an agent that increases the level and/or activity of an ABHD2 polypeptide in a cell) can be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption.

An agent (e.g., an agent that reduces the level and/or activity of an ABHD2 polypeptide in a cell; an agent that increases the level and/or activity of an ABHD2 polypeptide in a cell) can encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of an active agent, pharmaceutically acceptable salts of such prodrugs, and other bioequivalents.

The term "pharmaceutically acceptable salts" refers to physiologically and pharmaceutically acceptable salts of a subject nucleic acid: i.e., salts that retain the desired biological activity of the parent compound and do not impart undesired toxicological effects thereto. For polynucleotides, suitable examples of pharmaceutically acceptable salts and their uses are further described in U.S. Pat. No. 6,287,860, which is incorporated herein by reference in its entirety.

The present disclosure also includes compositions and formulations, including pharmaceutical compositions and formulations, which include an agent described herein (e.g., an agent that reduces the level and/or activity of an ABHD2 polypeptide in a cell; an agent that increases the level and/or activity of an ABHD2 polypeptide in a cell). A subject composition can be administered in a number of ways depending upon whether local or systemic treatment is desired and upon the area to be treated. Administration can be systemic or local, e.g., where local administration includes topical (e.g., topically to the skin), intradermal, and subcutaneous. Parenteral administration includes, but is not limited to, intravenous, intraarterial, subcutaneous, intraperitoneal, or intramuscular injection or infusion; or intracranial, e.g., intrathecal or intraventricular, administration. Compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be necessary or desirable.

A subject formulation, which may conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

A subject composition can be formulated into any of many possible dosage forms such as, but not limited to, tablets, capsules, gel capsules, liquid syrups, soft gels, suppositories, and enemas. A subject composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A subject composition may include solutions, emulsions, foams and liposome-containing formulations. A subject composition or formulation can comprise one or more penetration enhancers, carriers, excipients, or other active or inactive ingredients.

Emulsions are typically heterogeneous systems of one liquid dispersed in another in the form of droplets, which can exceed 0.1 μm in diameter. Emulsions may contain additional components in addition to the dispersed phases, and the active agent (e.g., antisense polynucleotides) which can be present as a solution in the aqueous phase, the oily phase, or as a separate phase. Microemulsions are also suitable. Emulsions and their uses are well known in the art and are further described in U.S. Pat. No. 6,287,860.

A subject formulation can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and non-cationic liposomes can be used to deliver a nucleic acid agent.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions of the present disclosure may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of an agent (e.g., an agent that reduces the level and/or activity of an ABHD2 polypeptide in a cell; an agent that increases the level and/or activity of an ABHD2 polypeptide in a cell). In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

A nucleic acid agent can be conjugated to poly(L-lysine) to increase cell penetration. Such conjugates are described by Lemaitre et al., Proc. Natl. Acad. Sci. USA, 84, 648-652 (1987). The procedure requires that the 3'-terminal nucleotide be a ribonucleotide. The resulting aldehyde groups are then randomly coupled to the epsilon-amino groups of lysine residues of poly(L-lysine) by Schiff base formation, and then reduced with sodium cyanoborohydride.

One of skill in the art will recognize that formulations are routinely designed according to their intended use and/or route of administration.

Suitable formulations for topical administration include those in which a subject agent is in admixture with a topical delivery agent such as lipids, liposomes, fatty acids, fatty acid esters, steroids, chelating agents and surfactants. Suitable lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, a subject agent can be encapsulated within liposomes or may form complexes thereto, in particular to cationic liposomes. Alternatively, a subject agent (e.g., a nucleic acid agent) can be complexed to lipids, in particular to cationic lipids. Suitable fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which an agent is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanoiamine, N,N-dimethylacetamide, N,N-dimethylformamide, 2-pyrrolidone and derivatives thereof, tetrahydrofurfuryl alcohol, and AZONE™.

An agent can be delivered orally, in granular form including sprayed dried particles, or complexed to form micro or nanoparticles.

Compositions and formulations for enteral or parenteral administration may include sterile aqueous solutions which may also contain buffers, diluents and other suitable additives such as, but not limited to, penetration enhancers, carrier compounds and other pharmaceutically acceptable carriers or excipients. In some cases, the formulation is one that is suitable for topical application to the skin.

Delivery and Routes of Administration

An agent (e.g., an agent that reduces the level and/or activity of an ABHD2 polypeptide in a cell; an agent that increases the level and/or activity of an ABHD2 polypeptide in a cell) can be administered by any suitable means. One skilled in the art will appreciate that many suitable methods of administering an agent to a host in the context of the present disclosure, e.g., a human, are available, and, although more than one route may be used to administer a particular nucleic acid agent, a particular route of administration may provide a more immediate and more effective reaction than another route.

Suitable routes of administration include enteral and parenteral routes. Administration can be via a local or a systemic route of administration. An agent (e.g., an agent that reduces the level and/or activity of an ABHD2 polypeptide in a cell; an agent that increases the level and/or activity of an ABHD2 polypeptide in a cell) can be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes, but is not limited to, intravenous, intraarterial, subcutaneous, intraperitoneal, or intramuscular injection or infusion.

In some embodiments, an agent is administered topically to the skin. In other embodiments, an agent is administered intradermally. In other embodiments, an agent is administered subcutaneously. In some embodiments, an agent is administered intramuscularly. In some embodiments, an agent is administered orally. In some embodiments, an agent is administered intravenously.

Dosing

The formulation of therapeutic compositions and their subsequent administration (dosing) is within the skill of those in the art. Dosing is dependent on several criteria, including severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual agents, and can generally be estimated based on EC50s found to be effective in vitro and in vivo animal models.

For example, a suitable dose of an agent can be from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight. Persons of ordinary skill in the art can easily estimate repetition rates for dosing based on measured residence times and concentrations of the drug in bodily fluids or tissues. Following successful treatment, it may be desirable to have the patient undergo maintenance therapy, wherein an agent is administered in maintenance doses, ranging from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight.

In some embodiments, multiple doses of an agent are administered. The frequency of administration of an agent can vary depending on any of a variety of factors. For example, in some embodiments, an agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of an agent, e.g., the period of time over which an active agent is administered, can vary, depending on any of a variety of factors, e.g., patient response, etc. For example, an agent can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Subjects suitable for treatment with a method of the present disclosure include, e.g., males, e.g., human males, e.g., sexually active human males; e.g., where the treatment method involves reducing the level and/or activity of an ABHD2 polypeptide. Subjects suitable for treatment with a method of the present disclosure include individuals who are suffering from pain; e.g., where the treatment method involves reducing the level and/or activity of an ABHD2 polypeptide in a DRG.

Screening Methods

The present disclosure provides methods for identifying an agent that inhibits/reduces the level and/or activity of an ABHD2 polypeptide. The present disclosure provides methods for identifying an agent that increases the level and/or activity of an ABHD2 polypeptide.

An "ABHD2 polypeptide" encompasses a polypeptide comprising an amino acid sequence having at least about 70%, at least about 75%, at least about 80%, at least about 85%, at least about 90%, at least about 95%, at least about 98%, or at least about 99% amino acid sequence identity to the ABHD2 amino acid sequence depicted in FIG. 13A. An "ABHD2 polypeptide" encompasses a polypeptide comprising an amino acid sequence having at least about 70%, at least about 75%, at least about 80%, at least about 85%, at least about 90%, at least about 95%, at least about 98%, or at least about 99% amino acid sequence identity to amino acids 31-425 of the ABHD2 amino acid sequence depicted in FIG. 13A. Also encompassed are ABHD2 fusion proteins.

An "ABHD2 nucleic acid gene product" encompasses a nucleic acid comprising a nucleotide sequence encoding polypeptide comprising any known ABHD2 amino acid sequence, a fragment thereof (e.g., an active fragment thereof), or an ortholog thereof. The term "ABHD2 nucleic acid gene product" further encompasses a nucleic acid comprising a nucleotide sequence having at least about 70%, at least about 75%, at least about 80%, at least about 85%, at least about 90%, at least about 95%, at least about 98%, or at least about 99% nucleotide sequence identity to the ABHD2 nucleotide sequence depicted in FIG. 13B. Also encompassed are nucleic acids comprising nucleotide sequences encoding ABHD2 fusion proteins.

An ABHD2 fusion protein comprises an ABHD2 polypeptide and a fusion partner. Suitable fusion partners include, but are not limited to, fluorescent proteins and enzymes (e.g., β-galactosidase, luciferase, horse radish peroxidase, alkaline phosphatase, etc.). Suitable fluorescent proteins include, but are not limited to, a green fluorescent protein (GFP), including, but not limited to, a GFP derived from *Aequoria victoria* or a derivative thereof, a number of which are commercially available; a GFP from a species such as *Renilla reniformis, Renilla mulleri,* or *Ptilosarcus guernyi*, as described in, e.g., WO 99/49019 and Peelle et al. (2001) *J. Protein Chem.* 20:507-519; a yellow fluorescent protein; a blue fluorescent protein; a red fluorescent protein; any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; and the like.

In some cases, the screening method is an in vitro cell-free method. In other cases, the screening method is an in vitro cell-based method.

In some cases, the screening method is an in vitro cell-based method. In some cases, a mammalian cell is used. Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some cases, the mammalian cell expresses, or is genetically modified to express, the sperm calcium channel CatSper. In some cases, the mammalian cell expresses, or is genetically modified to express, an ABHD2 polypeptide.

In some cases, a test agent that reduces the level and/or activity of an ABHD2 polypeptide by at least 10%, at least 15%, at least 20%, at least 25%, at least 30%, at least 40%, at least 50%, at least 60%, at least 70%, at least 80%, or more than 80%, is a candidate agent for contraception. For example, in some cases, a test agent that reduces the level and/or activity of an ABHD2 polypeptide by at least 10%, at least 15%, at least 20%, at least 25%, at least 30%, at least 40%, at least 50%, at least 60%, at least 70%, at least 80%, or more than 80%, is a candidate agent for reducing sperm motility.

In some cases, a test agent that increases the level and/or activity of an ABHD2 polypeptide by at least 10%, at least 15%, at least 20%, at least 25%, at least 30%, at least 40%, at least 50%, at least 60%, at least 70%, at least 80%, at least 2-fold, at least 5-fold, at least 10-fold, at least 20 fold, or more than 20-fold, is a candidate agent for treating pain.

Test Agents

By "test agent," "candidate agent," and grammatical equivalents herein, which terms are used interchangeably herein, is meant any molecule (e.g. proteins (which herein includes proteins, polypeptides, and peptides), small (i.e., 5-1000 Da, 100-750 Da, 200-500 Da, or less than 500 Da in size), or organic or inorganic molecules, polysaccharides, polynucleotides, etc.) which are to be tested for activity in a subject assay.

A variety of different candidate agents may be screened by the above methods. Candidate agents encompass numerous chemical classes, e.g., small organic compounds having a molecular weight of more than 50 daltons (e.g., at least about 50 Da, at least about 100 Da, at least about 150 Da, at least about 200 Da, at least about 250 Da, or at least about 500 Da) and less than about 20,000 daltons, less than about 10,000 daltons, less than about 5,000 daltons, or less than about 2,500 daltons. For example, in some embodiments, a suitable candidate agent is an organic compound having a molecular weight in a range of from about 500 Da to about 20,000 Da, e.g., from about 500 Da to about 1000 Da, from about 1000 Da to about 2000 Da, from about 2000 Da to about 2500 Da, from about 2500 Da to about 5000 Da, from about 5000 Da to about 10,000 Da, or from about 10,000 Da to about 20,000 Da.

Candidate agents can comprise functional groups necessary for structural interaction with proteins, e.g., hydrogen bonding, and can include at least an amine, carbonyl, hydroxyl or carboxyl group, or at least two of the functional chemical groups. The candidate agents can comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Moreover, screening may be directed to known pharmacologically active compounds and chemical analogs thereof, or to new agents with unknown properties such as those created through rational drug design.

In one embodiment, candidate modulators are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods.

In another embodiment, the candidate agents are provided as libraries of natural compounds in the form of bacterial, fungal, plant and animal extracts that are available or readily produced. Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In one embodiment, candidate agents include proteins (including antibodies, antibody fragments (i.e., a fragment containing an antigen-binding region, single chain antibodies, and the like), nucleic acids, and chemical moieties. In one embodiment, the candidate agents are naturally occurring proteins or fragments of naturally occurring proteins. Thus, for example, cellular extracts containing proteins, or random or directed digests of proteinaceous cellular extracts, may be tested. In this way libraries of prokaryotic and eukaryotic proteins may be made for screening. Other embodiments include libraries of bacterial, fungal, viral, and mammalian proteins (e.g., human proteins).

In one embodiment, the candidate agents are organic moieties. In this embodiment, as is generally described in WO 94/243 14, candidate agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested.

As used herein, the term "determining" refers to both quantitative and qualitative determinations and as such, the term "determining" is used interchangeably herein with "assaying," "measuring," and the like.

The assay can include one or more additional reagents. These include reagents like salts, neutral proteins, e.g. albumin, detergents, etc., including agents that are used to facilitate optimal enzyme activity and/or reduce non-specific or background activity. Reagents that improve the efficiency of the assay, such as protease inhibitors, anti-microbial agents, etc. may be used. The components of the assay mixture are added in any order that provides for the requisite activity. Incubations are performed at any suitable temperature, e.g., between 4°C and 40°C. Incubation periods are selected for optimum activity, but may also be optimized to facilitate rapid high-throughput screening. Typically between 0.1 hour and 1 hour will be sufficient.

Assays of the present disclosure include controls, where suitable controls include a cell not contacted with the test agent. Generally a plurality of assay mixtures is run in parallel with different agent concentrations to obtain a differential response to the various concentrations. Typically, one of these concentrations serves as a negative control, i.e. at zero concentration or below the level of detection.

A candidate agent is assessed for any cytotoxic activity it may exhibit toward a living eukaryotic cell, using well-known assays, such as trypan blue dye exclusion, an MTT (344,5-dimethylthiazol-2-yl)-2,5-diphenyl-2 H-tetrazolium bromide) assay, and the like. Agents that do not exhibit cytotoxic activity are considered candidate agents.

Assaying ABHD2 Enzymatic Activity

In some embodiments, a subject method involves determining the effect of a test agent on ABHD2 enzymatic activity. For example, in some cases, a subject screening method involves determining the effect of a test agent on hydrolysis of acylglycerol, e.g., a monoacylglycerol (e.g., hydrolysis of 2-arachidonoylglycerol (2-AG) and/or 1-arachidonoylglycerol (1-AG)), by an ABHD2 polypeptide. In some cases, a method of identifying an agent that inhibits ABHD2 enzymatic activity comprises contacting an ABHD2 polypeptide with a test agent, in the presence of P4 and an acylglycerol substrate for ABHD2; and determining the effect of the test agent on production of a glycerol product of the acylglycerol, i.e., determining the amount of free glycerol. In some cases, a method of identifying an agent that increases ABHD2 enzymatic activity comprises contacting an ABHD2 polypeptide with a test agent, in the presence of P4 and an acylglycerol substrate for ABHD2; and determining the effect of the test agent on production of a glycerol product of the acylglycerol, i.e., determining the amount of free glycerol.

Free glycerol quantitation can be performed as described Navia-Paldanius, D., Savinainen, J. R., and Laitinen, J. T. (2012). Biochemical and pharmacological characterization of human alpha/beta-hydrolase domain containing 6 (ABHD6) and 12 (ABHD12). Journal of lipid research 53, 2413-2424. For example, cells transfected to express ABHD2 can be washed with phosphate buffered saline (PBS), collected by scraping, resuspended in 50 µl PBS and lysed by freeze fracture and sonication. Total protein can be quantified using Pierce 660 reagent, and lysates aliquoted for storage in −80° C. until use. For assay, 0.3 µg of protein is added per well to 100 µl of assay buffer (50 mM Tris-HCl, 1 mM EDTA, 5 mM $MgCl_2$, 100 mM NaCl, 0.5% BSA plus progesterone [100 µM in ethanol] or vehicle) in a 96-well plate. To lysate solution, 100 µl of quantitation buffer is added (per well: 0.4 U Glycerol kinase, 0.4 U glycerol-3-phosphate oxidase, 0.4 U horseradish peroxidase, 0.25 mM ATP, and 20 µM Ampliflu Red in assay buffer with substrate or vehicle. 1-AG can be used as substrate at a final concentration of 25 µM). Fluorescence (emission 532 nm and excitation 580 nm) is monitored every 10 min for a total of 90 minutes. Background fluorescence is subtracted by including cell and substrate free wells. A glycerol titration (63-500 pmol/well) is also included for each assay run to generate standard curves by which free glycerol production could be determined.

Assaying Binding of ABHD2 to P4

In some cases, a subject screening method involves determining the effect of a test agent on binding of P4 to an ABHD2 polypeptide. In some cases, a P4 analog is used, e.g., Progesterone-3-CMO-(2-biotinyl-PEG2-aminopropylamido-4-trifluoromethyl diazirinyl benzamide). In some cases, the ABHD2 polypeptide is a fusion polypeptide. In some cases, the effect of a test agent on binding of P4 to an ABHD2 polypeptide is determined using an immunological assay, e.g., an enzyme-linked immunosorbent assay, a radio-immunoassay, and the like.

Assaying Intracellular Calcium Ion Concentration

In some embodiments, a subject method involves determining the intracellular calcium ion concentration ($[Ca^{2+}]_i$) in a cell in response to a test agent. The intracellular calcium ion concentration in a cell can be determined using a calcium-sensing dye.

Suitable intracellular $Ca^{2+}$ ion-detecting dyes include, but are not limited to, fura-2, bis-fura 2, indo-1, Quin-2, Quin-2 AM, Benzothiaza-1, Benzothiaza-2, indo-5F, Fura-FF, BTC, Mag-Fura-2, Mag-Fura-5, Mag-Indo-1, fluo-3, rhod-2, fura-4F, fura-5F, fura-6F, fluo-4, fluo-5F, fluo-5N, Oregon Green 488 BAPTA, Calcium Green, Calcein, Fura-C18, Calcium Green-C18, Calcium Orange, Calcium Crimson, Calcium Green-5N, Magnesium Green, Oregon Green 488 BAPTA-1, Oregon Green 488 BAPTA-2, X-rhod-1, Fura Red, Rhod-5F, Rhod-5N, X-Rhod-5N, Mag-Rhod-2, Mag-X-Rhod-1, Fluo-5N, Fluo-5F, Fluo-4FF, Mag-Fluo-4, Aequorin, dextran conjugates or any other derivatives of any of these dyes, and others (see, e.g., the catalog or Internet site for Molecular Probes, Eugene, see, also, Nuccitelli, ed., Methods in Cell Biology, Volume 40: A Practical Guide to the Study of Calcium in Living Cells, Academic Press (1994); Lambert, ed., Calcium Signaling Protocols (Methods in Molecular Biology Volume 114), Humana Press (1999); W. T. Mason, ed., Fluorescent and Luminescent Probes for Biological Activity. A Practical Guide to Technology for Quantitative Real-Time Analysis, Second Ed, Academic Press (1999); Calcium Signaling Protocols (Methods in Molecular Biology), 2005, D. G. Lamber, ed., Humana Press).

Assaying Voltage Changes

In some embodiments, a subject method involves determining the effect of a test agent on membrane voltage. Changes in membrane voltage can be determined using voltage-sensitive dyes.

Suitable voltage-sensitive dyes include, but are not limited to, merocyanine-oxazolone dyes (e.g., NK2367); merocyanine-rhodanine dyes (e.g., NK2495, NK2761, NK2776, NK3224, and NK3225); oxonol dyes (e.g., RH155, RH479, RH482, RH1691, RH1692, and RH1838); styryl dyes (e.g., RH237, RH414, RH421, RH437, RH461, RH795, JPW 1063, JPW3028, di-4-ANEPPS, di-9-ANEPPS, di-2-ANEPEQ, di-12-ANEPEQ, di-8-ANEPPQ, and di-12-ANEPPQ); and the like.

Determining Electrophysiological Changes

In some embodiments, a subject method involves determining the effect of a test agent on electrophysiology of a cell. Electrophysiological changes can be determined using any known method including, e.g., a standard patch clamp method.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Characterization of ABHD2

The serine hydrolase ABHD2 has been characterized. It was found that ABHD2 metabolizes endocannabinoids 1-AG/2-AG only in the presence of progesterone. Moreover, it was shown that AGs act as endogenous inhibitors of the sperm calcium channel CatSper. According to the model presented herein, P4 stimulates ABHD2 hydrolysis of 2-AG and releases CatSper from inhibition. Calcium influx via CatSper triggers sperm hyperactivation and makes spermatozoa fertile.

Experimental Procedures
Animals and Animal Tissues

Male C57BL/6 mice and Wistar rats were purchased from Harlan Laboratories (Livermore, Calif.) and were kept in the Animal Facility of the University of California, Berkeley. All experiments were performed in strict accordance with NIH Guidelines for Animal Research and approved by UC Berkeley Animal Care and Use Committee under the approved protocol MAUP #R352-012 Animals were humanely euthanized according to ACUC guidelines, and sperm were collected as described previously(Wennemuth et al., 2003). Sperm cells from adult male rhesus macaques [*Macaca mulatta*, Mmu] were obtained via collaboration with Dr. Stuart Meyers at UC Davis and California National Primate Research Center in compliance with standards of the Association for Assessment and Accreditation of Laboratory Animal Care International (AAALAC). Sperm cells were purified as described in (Sumigama S., 2015). Bovine and boar ejaculated semen were obtained from UC Davis.

Healthy Donors and Isolation of Human Ejaculated Spermatozoa

A total of 25 healthy volunteers aged 21-38 were recruited to this study. Freshly ejaculated semen samples were obtained by masturbation. Spermatozoa were purified by the swim-up technique as described (Lishko et al., 2011). Protocols for the human sperm studies were approved by the Committee on Human Research at the University of California, Berkeley, protocol number 2013-06-5395. Freshly ejaculated sperm samples were obtained from 25 healthy young donors by masturbation and allowed to liquefy for 30-60 min at room temperature before processing. Human spermatozoa were purified by the swim up method in the artificial human tubal fluid solution (HTF, in mM): 98 NaCl, 4.7 KCl, 0.3 $KH_2PO_4$, 2 $CaCl_2$, 0.2 $MgSO_4$, 21 HEPES, 3 glucose, 21 lactic acid, 0.3 sodium pyruvate, pH 7.4 (adjusted with NaOH).

Electrophysiology

All CatSper recordings was performed as described in (Lishko et al., 2013; Lishko et al., 2011). Briefly, gigaohm seal between the patch pipette and human spermatozoon was formed at the cytoplasmic droplet. Spermatozoa were patched either at the cytoplasmic droplet or, if the cytoplasmic droplet was inconspicuous, at the neck region. Seals were formed in high saline (HS) solution containing: 130 mM NaCl, 5 mM KCl, 1 mM $MgSO_4$, 2 mM $CaCl_2$, 5 mM glucose, 1 mM sodium pyruvate, 10 mM lactic acid, 20 mM HEPES, pH 7.4 adjusted with NaOH, 320 mOsm/L. Transition into the whole-cell mode was performed by applying short voltage pulses. Access resistance was 25-40 M. Cells were stimulated every 5 s. Data were sampled at 2-5 kHz and filtered at 1 kHz. Pipettes (11-17 MΩ) for whole-cell patch-clamp recordings of monovalent CatSper currents were filled with (in mM): 130 Cs-methanesulfonate, 70 HEPES, 3 EGTA, 2 EDTA, 0.5 TrisHCl, pH 7.4 adjusted with CsOH. Bath divalent free (DVF) solution for recording of monovalent CatSper currents contained (in mM): 140 Cs-methanesulfonate, 40 HEPES, 1 EDTA, pH 7.4 adjusted with CsOH. HEPES was substituted for MES in the event when acidic extracellular pH was used. HS solution was used to record baseline current while measuring monovalent CatSper currents ($Ca^{2+}$ in HS solution inhibits monovalent CatSper currents and causes $Ca^{2+}$-dependent inactivation of CatSper channels). Osmolarities of above mentioned solutions were approximately 321 mOsm/L and 335 mOsm/L for bath and pipette solutions, respectively. All electrophysiology experiments were performed at ambient temperature. $I_{catSper}$ were elicited by voltage ramps from a holding potential of 0 mV. Ramps were applied from −80 mV to +80 mV. Data were analysed with Origin 7.0 and Clampfit 9.2. Statistical data were calculated as the mean±S.E.M., and (n) indicates number of experiments. To determine $I_{catSper}$ inactivation rate current densities extracted from voltage ramps and acquired at +80 pA were plotted against time. The data were fitted with Boltzmann equation $y=1/(1+\exp((x-t)/dx))$ and mean ti numbers were determined from (n) independent experiments. Statistical significance (t-test) is indicated by (**, $p \leq 0.01$ and *, $p \leq 0.05$).

ABHD Cloning and Expression

The complete open reading frame of ABHD2 was amplified used gene specific primers (FWD 5'-atgaatgccatgctg-gag-3' (SEQ ID NO:5); REV 5'-agagtccggaggcctca-3' (SEQ ID NO:6)) from cDNA libraries generated from purified human sperm samples. The gateway cloning system (Life Technologies, Carlsbad, Calif.) was used to insert the sequence confirmed full length gene to in mammalian expression vector pEZYflag (Addgene plasmid #18700), (Guo et al., 2008). This expression vector allows for expression of an N-terminal FLAG-tagged protein of interest. For recombinant expression, HEK-293 or CHO cells were transfected using lipofectamine 2000 reagent (Life Technologies, Carlsbad, Calif.) according to manufacturer's recommendation and overexpression was verified by the presence of FLAG-tagged proteins using M2 anti-FLAG antibody F1804 (Sigma, St. Louis, Mo.) in western blot analysis. Human ABHD12 ORF was obtained from PlasmID (Harvard Medical School, MA) and subcloned into the previously mentioned mammalian expression vector, pEZYflag. All of the PCR products obtained from cloning experiments were DNA sequence verified against canonical refseq sequences.

PI-PLC Treatment and Progesterone Binding Protein Pull-Down

After collection, sperm cells were treated with 0.5 units (U) of PI-PLC (P6466; Life Technologies, Carlsbad, Calif.) and incubated at 37° C. for an hour. Cells were then washed twice with DVF solution and treated for 10 minutes in the presence of 250 nM P4*, kept at ambient temperature in the dark for 10 minutes under gentle agitation and UV irradiated (312 nm) for an additional 3 minutes. Samples were then washed three times with HS solution and lysed on ice for 30 minutes. Lysates were added to streptavidin coated magnetic beads (65001; Life Technologies, Carlsbad, Calif.) on ice for another thirty minutes with gentle agitation. Bound proteins were eluted by boiling in Laemmli Sample Buffer in the presence of beta-mercaptoethanol and subjected to SDS-polyacrylamide gel electrophoresis. The proteins were transferred onto a polyvinylidene difluoride (PVDF) membrane, blocked in PBS with 0.05% Tween 20 (PBS-T) containing 3% IgG-free bovine serum albumin and then incubated with peroxidase (POD)-conjugated streptavidin to detect proteins with P4* bound. For proteomic identification of bands of interest, proteins pulled down by streptavidin and P4* were visualized in SDS-polyacrylamide gels using imperial protein stain (24615, Thermo Scientific). Bands were excised and subjected to in-gel trypsinization after which peptides were extracted and dried for use in proteomic analysis.

CHO cells: cells were transfected with ABHD2 plasmid for 24-48 hours prior to P4* treatment and P4* binding was proceeded in the same manner as for sperm cells. Briefly, P4* binding to recombinant ABHD2 was performed by applying 250 nM P4* in the absence or presence of unlabeled steroid to live cells for ten minutes prior to 3 minutes UV irradiation. Cells were then washed, lysed and loaded into a polyacrylamide gel for western blot analysis.

Protein Mass Spectrometry

Mass spectrometry was performed by the Vincent J. Coates Proteomics/Mass Spectrometry Laboratory at UC Berkeley. A nano LC column was packed in a 100 μm inner diameter glass capillary with an emitter tip. The column consisted of 10 cm of Polaris c18 5 μm packing material (Varian). The column was loaded by use of a pressure bomb and washed extensively with buffer A (see below). The column was then directly coupled to an electrospray ionization source mounted on a Thermo-Fisher LTQ XL linear ion trap mass spectrometer. An Agilent 1200 HPLC equipped with a split line to deliver a flow rate of 300 nl/min was used for chromatography. Peptides were eluted with a linear gradient from 100% buffer A to 60% buffer B in 2.5 hours. Buffer A was 5% acetonitrile/0.02% heptaflurobutyric acid (HBFA); buffer B was 80% acetonitrile/0.02% HBFA. Protein identification was done with Integrated Proteomics Pipeline software (IP2, Integrated Proteomics Applications, Inc. San Diego, Calif.) using ProLuCID/Sequest and DTASelect2(Cociorva et al., 2007; Park et al., 2008; Tabb et al., 2002). Tandem mass spectra were extracted into ms1 and ms2 files from raw files using RawExtract 1.9.9(McDonald et al., 2004) and were searched against the human protein database plus sequences of common contaminants, concatenated to a decoy database in which the sequence for each entry in the original database was reversed(Peng et al., 2003). LTQ data was searched with 3000.0 milli-amu precursor tolerance and the fragment ions were restricted to a 600.0 ppm tolerance. All searches were parallelized and searched on the VJC proteomics cluster. Search space included all tryptic peptide candidates with no missed cleavage restrictions. Carbamidomethylation (+57.02146) of cysteine was considered a static modification and oxidation of methionine (+15.9949) was a variable modification. One peptide per protein and two tryptic termini were required for each peptide identification. The ProLuCID search results were assembled and filtered using the DTASelect program (version 2.0)(Cociorva et al., 2007; Tabb et al., 2002) with a general peptide FDR of 0.005 and a peptide FDR of 0.001 for inclusion at the protein level. Under such filtering conditions, the global peptide false discovery rate was 0.37 or less for all samples.

Lipid Extraction

In order to selectively extract lipids from the plasma membrane a novel cyclodextrin-based lipid extraction protocol was developed to allow removal of steroids and single-tailed lipids, such as AGs, while leaving multi-tailed lipids in the membrane. Once extracted, the lipids were separated from the cyclodextrin via a hexane:isopropanol technique, and purified extracellular lipids were analyzed using an LTQ-Orbitrap-XL mass spectrometer equipped with an ESI source and operated in the negative ion mode. Briefly, between 33 and 37 million sperm cells from 5 different human donors were assessed. Sperm cells were washed with DVF and treated with 500 nM P4* or vehicle for 10 minutes and then 5 mM beta-cyclodextrin C4805 (Sigma, St. Louis, Mo., USA) for another 10 min. Cells were pelleted down and supernatant added to streptavidin magnetic beads (Dynabeads MyOne Streptavidin Cl, #65001; Life Technologies, Carlsbad, Calif.) to remove P4* from extract. Flow through was treated for 10 minutes at 55° C. with maltogenic amylase (A2986, Sigma, St. Louis, Mo.) to hydrolyze beta-cyclodextrin. Lipids were extracted from live cells using hexane:isopropanol method (Hara and Radin, 1978), dried under gentle nitrogen flow and samples reconstituted in 7:1 methanol/water prior to analysis. A cell free control was also run to account for lipid contamination present within any of the treatment, pull-down or extraction steps. This condition was used to determine the baseline for the lipid detection (below 100 fmol).

Liquid Chromatography-Mass Spectrometry

Methanol (Fisher Optima grade, 99.9%), ammonium formate (Alfa Aesar, 99%), and water purified to a resistivity of 18.2 MΩ·cm (at 25° C.) using a Milli-Q Gradient ultrapure water purification system (Millipore, Billerica, Mass.), were used to prepare mobile phase solvents. Lipid extracts were analyzed using an Agilent 1200 liquid chromatograph (LC; Santa Clara, Calif.) that was connected in-line with an LTQ-Orbitrap-XL mass spectrometer equipped with an electrospray ionization source (ESI; Thermo Fisher Scientific, Waltham, Mass.). The LC was equipped with a C4 analytical column (Viva C4, 150 mm length×1.0 mm inner diameter, 5 μm particles, 300 Å pores, Restek, Bellefonte, Pa.). Solvent A was water with 20 mM ammonium formate and solvent B was methanol. The sample injection volume was 50 μL. The elution program consisted of isocratic flow at 1% B for 3 min, a linear gradient to 99% B over 32 min, isocratic flow at 99% B for 5 min, and isocratic flow at 1% B for 19.9 min, at a flow rate of 150 μL/min. The column and sample compartments were maintained at 40° C. and 4° C., respectively. The injection needle was rinsed with a 1:1 methanol:water (v/v) solution after each injection to avoid cross-contamination between samples. The column exit was connected to the ESI probe of the mass spectrometer using PEEK tubing (0.005" inner diameter×1/16" outer diameter, Agilent). Mass spectra were acquired in the negative ion mode over the range m/z=100 to 1000 using the Orbitrap mass analyzer, in profile format, with a mass resolution setting of 100,000 (at m/z=400, measured at full width at half-maximum peak height. Mass spectra were processed and analyzed using Xcalibur software (version 2.0.7, Thermo) and LIPID MAPS Online Tools (Fahy et al., 2007). To confirm the identity of the 2AG ion, the synthetic compound was analyzed under identical conditions as the isolated lipid mixtures. It was determined from the lipid standard that 2-AG occurs as a formate adduct ion, [M+45

Da], in negative ion ESI, with a chromatographic retention time in the range of 30-40 minutes.

Reagents

Progesterone was purchased from CalBiochem (EMD Millipore, Darmstadt, Germany), 2-AG was from Enzo Life Sciences Inc. (Farmingdale, N.Y.), 1-AG, methyl arachidonyl fluorophosphanate (MAFP) was from Cayman Chemical Company (Ann Arbor, Mich.). Progesterone-3-CMO-(2-biotinyl-PEG2-aminopropylamido-4-trifluoromethyl diazirinyl benzamide), a modified P4 analog (P4*) was synthesized by Cayman Chemical Company. All other compounds were from Avanti Polar Lipids (Alabaster, Ala.) or Sigma Aldrich (St. Louis, Mo.) unless otherwise specified. ABHD2 antibodies (labelled in the text as "ABHD2 ABa") were obtained from One World Lab: C14214 (San Diego, Calif.; affinity-purified anti-ABHD2 polyclonal rabbit IgG). ABHD2 antibodies (labelled in the text as "ABHD2 ABb") were purchased from Proteintech 14039-1-AP (Rosemont, Ill.). ACPP antibodies (PAP) were obtained from Ayes lab (Tigard, Oreg.). Nonspecific Rabbit IgG was purchased from Jackson ImmunoResearch lab (111-005-003; West Grove, Pa.). Monoclonal acetylated alpha-tubulin antibody (clone 6-11B-1) was purchased from Sigma.

Immunocytochemistry

Purified spermatozoa (concentration ~$10^7$ cells/ml) were plated onto 20 mm coverslips in HS and allowed to attach for 20 min. The cells were fixed with 4% paraformaldehyde (PFA) in 1×PBS for 10 min and washed twice with PBS. Additional fixation was performed with 100% ice-cold methanol for 1 min with two washes in 1×PBS. Cells were permeabilized for 5 min with 0.5 μg/ml saponin in PBS followed by two PBS washes and blocked by hour incubation in PBS supplemented with 10% gamma-globulin free BSA Immunostaining was performed in blocking solution. Detergent-treated cells were incubated with primary antibodies overnight at 4° C. After extensive washing in PBS, secondary antibodies were added for 30 min. After vigorous washing, cells were mounted with ProLong Gold antifade with DAPI reagent (Life Technologies, Carlsbad, Calif.). Images were acquired on an Olympus IX71 microscope equipped with differential interference contrast (DIC) and coupled to an XCite fluorescence source. Alexa488-conjugated anti-rabbit antibodies were obtained from Thermo Scientific.

Electrophoresis and Immunoblotting

Protease inhibitors were used throughout the following procedure. Highly motile sperm swim-up fraction was subjected to osmotic shock by a 5 min incubation in 0.5×HS solution, addition of 10 mM EDTA and 10 mM DTT for 10 min, and sonication in a water bath at 25° C. for 5 min. Osmolarity was adjusted by addition of 10×PBS. 5× Laemmli sample buffer was added to a final 1× concentration and the DTT concentration adjusted to 20 mM. An additional 5 min sonication and boiling at 100° C. for 5 min were performed. Total crude cell lysate was loaded onto a 4-20% gradient Tris-HCl Criterion™ SDS-PAGE gel (BioRad). ABHD2, ABHD12 and empty vector-transfected CHO cells were lysed in 2× Laemmli sample buffer and $10^4$ cell per well subjected to SDS-PAGE. Following transfer to PVDF membranes, blots were blocked in 0.1% PBS-Tween20 with 3% IgG free BSA for 15 min and incubated in primary antibodies overnight at 4° C. Blots were probed with either: anti-ABHD2 (C14214, One World Lab, San Diego, Calif.), anti-FLAG or mouse monoclonal anti-actin C4 antibodies (Abcam, Cambridge, Mass.). After subsequent washing and incubation with secondary HRP-conjugated antibodies (Abcam, Cambridge, Mass.), membranes were developed with an ECL SuperSignal West Pico kit (Pierce, Life Technologies, Carlsbad, Calif.).

Glycerol Assay

Free glycerol quantitation was performed as described in (Navia-Paldanius et al., 2012). Navia-Paldanius, D., Savinainen, J. R., and Laitinen, J. T. (2012). Biochemical and pharmacological characterization of human alpha/beta-hydrolase domain containing 6 (ABHD6) and 12 (ABHD12). Journal of lipid research 53, 2413-2424. Briefly, transfected cells were washed with phosphate buffered saline (PBS), collected by scraping, resuspended in 50 μl PBS and lysed by freeze fracture and sonication. Total protein was quantified using Pierce 660 reagent, and lysates aliquoted for storage in −80° C. until use. For assay, 0.3 μg of protein was added per well to 100 μl of assay buffer (50 mM Tris-HCl, 1 mM EDTA, 5 mM $MgCl_2$, 100 mM NaCl, 0.5% BSA plus progesterone [100 μM in ethanol] or vehicle) in a 96-well plate. To lysate solution, 100 μl of quantitation buffer was added (per well: 0.4 U Glycerol kinase, 0.4 U glycerol-3-phosphate oxidase, 0.4 U horseradish peroxidase, 0.25 mM ATP, and 20 μM Ampliflu Red in assay buffer with substrate or vehicle. For these experiments, 1-AG was used as substrate at a final concentration of 25 μM). Fluorescence (emission 532 nm and excitation 580 nm) was monitored every 10 min for a total of 90 minutes. Background fluorescence was subtracted by including cell and substrate free wells. A glycerol titration (63-500 pmol/well) was also included for each assay run to generate standard curves by which free glycerol production could be determined. Presented data is the average of two individual cell transfections assayed in duplicate plus or minus S.E.M.

Mouse Sperm Capacitation and Acrosome Exocytosis Assessment in Live Sperm

Acrosome status was assessed using transgenic mice B6D2-Tg(CAG/Su9-DsRed2,Acr3-EGFP)RBGS002Osb). These mice express EGFP that is targeted to acrosome, and is lost at the time of acrosomal exocytosis. Spermatozoa from the cauda epididymides were capacitated by isolating and perforating the cauda epididymis and suspending it in 500 μL of HTF media (Irvine scientific) for 30 min at 37° C. under 5% $CO_2$. After this treatment the cauda was removed and free swimming sperm were allowed to incubate for another 30 min in the same culture conditions. To assess induced acrosome exocytosis, capacitated sperm cells were allowed to adhere to poly-d-lysine coated coverslips and then incubated for 15 minutes with drug or vehicle after which time coverslips were imaged for the presence of fluorescently labelled acrosome. For MAFP effect, cells were pre-incubated for ten minutes with 2 μM MAFP or vehicle. At least 100 cells were scored for each condition by two independent researchers. Data were presented as the mean of three individual experiments±S. E. M.

RNA Deep Sequencing Analysis of the Human Sperm and Human Monocytes

Total RNA was extracted from human spermatozoa purified from 32 human semen samples of 7 different donors. Sperm purification was carried out by gradient centrifugation using ISolate™ (Irvine Scientific, CA) density gradient medium. Two ISolate concentrations were made: 80% and 40%, both were prepared with HS solution. Spermatozoa were initially purified from semen samples by spin down method described in Lishko et al, 2010 and then overlayed on top gradient (40% ISolate) and centrifuged for another 30 minutes at 300 g. Pure spermatozoa were collected at the bottom and visually examined for purity and contamination under phase-contrast microscope. Only 100% pure sperm samples were used for RNA extraction. Since monocytes are often found in human ejaculates, comparison of both transcriptomes should be used to determine sperm specific transcripts. Peripheral blood mononuclear cells (PBMC) were purchased from AllCells (Emeryville, Calif.), product number PB004F. PBMC were from the age-matched male donor. Total RNA was extracted from cells using Qiagen RNeasy kit and sequencing libraries were prepared poly A+-enriched RNA using Illumina mRNA-Seq Sample Prep Kit according to the manufacturer's instructions. Libraries were sequenced on the Illumina Genome Analyzer II using 36-cycle sequencing kit v3 by standard protocols. Single read FC flow cell was used for sequencing. Sequences were aligned to human genome GRCh37.

Sperm Motility Analysis

Viable human spermatozoa were selected by swim-up and a subset of cells allowed to capacitate at 37° C. in normal capacitation media for 3.5 hours. Cells were divided into equal aliquots and pre-incubated for 15 minutes in the presence of vehicle or MAFP (2 μM) prior to exposure to progesterone (3 μM). Human CASA was done with 3 μM of P4, which is due to mimic physiological concentrations of progesterone which could be found up to 10 μM. Sperm motility was analyzed by a computer-assisted semen analysis (CASA, HTM-IVOS sperm analysis system, version 12.3, Hamilton Thorne Biosciences, Beverly, Mass.) system that measured average path velocity (VAP, μm/s), straight line velocity (VSL, μm/s) and curvilinear velocity (VCL, μm/s). The linearity of progression [LIN=(VSL/VCL)×100], and straightness [STR=(VSL/VAP)×100] was determined from these measurements. Data analysis focused on VCL as no significant progesterone induced effect was observed for LIN or STR. Data were normalized to vehicle matched controls and presented as the average of (n) individual experiments+/−S.E.M. For all experimental conditions, a minimum of 10 fields of view were analyzed and all experiments performed at 37° C.

Calcium Imaging

Human spermatozoa purified by swim-up method as described above were loaded with 10 ug/ml of fluo-4 in HS solution and 0.05% pluronic for 30 minutes at room temperature. Cells were then allowed to adhere to poly-d-lysine coated imaging chambers for 10 mins and then washed with imaging medium (HS supplemented with 15 mM NaHCO3). Washed sperm were left in 200 μl of imaging buffer for 20 minutes prior to fluorescence recording. Imaging was performed using Olympus IX-71 microscope equipped with Lambda XL (Sutter, Calif.) and fluorescence was recorded at 2 Hz over a 25 second time frame and fluorescence change over time performed determined as ΔF/F0 were ΔF was the change in fluorescence intensity (F−F0) and F0 was the baseline as calculated by averaging the fluorescence signal five seconds prior to stimulus application. Calcium imaging results (FIG. 14A-14D) were presented as the average+/−the standard deviation of greater than 50 individual sperm flagella and the regions of interest (ROI) were selected manually using MetaFluor Imaging software (Molecular Devices).

Data Analysis

Data were analyzed with Origin 7.0 and Clampfit 9.2. Statistical data were calculated and represented everywhere in text as the mean±S.E.M., and (n) indicates number of experiments. To determine $I_{CatSper}$ inactivation rate current densities extracted from voltage ramps and acquired at +80 pA were plotted against time. The data were fitted with Boltzmann equation $y=1/[1+\exp((x-\tau)/dx)]$ and mean τ numbers were determined from (n) independent experiments. Hill equation was used to build dose-response curve: $y=V_{max}*x^n/(k^n+x^n)$. where n defines Hill slope factor, k defines $IC_{50}$, and $V_{max}$ is close to 100% inhibition. Statistical significance (t test) is indicated by (**$P<0.0001$, *$P<0.001$, **$P<0.005$ and *$P<0.05$).

Results

An Unbiased Strategy for Progesterone Receptor Identification

Figure 2B:
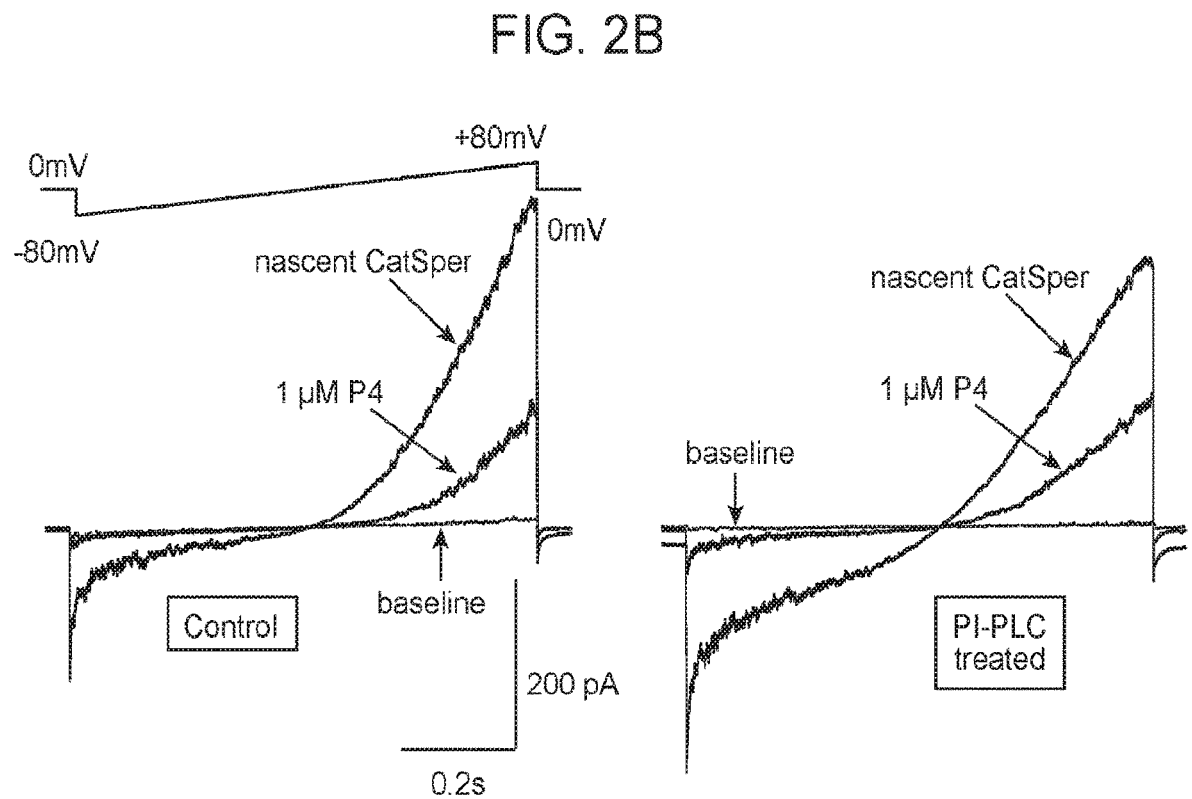

The CatSper channel is comprised of seven subunits that together form the sperm specific cation channel expressed exclusively within the flagellum (Carlson et al., 2003; Chung et al., 2011; Kirichok et al., 2006; Lishko et al., 2012; Liu et al., 2007; Navarro et al., 2008; Qi et al., 2007; Quill et al., 2001; Wang et al., 2009; Xia et al., 2007). Functional expression of CatSper in heterologous systems has not been achieved despite attempts by many different groups. Therefore, functional characterization of this channel complex is limited to its native system, spermatozoa. Sperm cells are transcriptionally silent and therefore lack conventional P4 genomic signaling. By applying the sperm patch clamp technique in whole-cell mode (Lishko et al., 2013; Lishko et al., 2010) and depleting sperm from all hydrophilic intracellular and extracellular second messengers such as calcium or ATP, it has been shown herein that CatSper is reversibly activated by P4 and its precursor 17-OH—P exclusively in a non-genomic manner (Lishko et al., 2011) (FIG. 1A-1B and FIG. 2A). This activation could take place under two foreseeable scenarios: either P4 binds to its non-genomic receptor which is a part of the CatSper complex, or P4 binds to a separate target initiating bioactive lipid signaling within the sperm plasma membrane ultimately leading to CatSper activation. Based on previous work using cell impermeable P4 to activate the CatSper channel (Lishko et al., 2011), the P4 target is localized to the outer leaflet of the plasma membrane. This suggests that the P4 receptor is either a peripheral membrane protein or a transmembrane protein with an extracellular P4 binding domain To test the possibility of P4 receptor being a glycosylphosphatidylinositol anchored protein (GPI-linked), sperm cells were treated with phosphoinositide phospholipase C (PI-PLC), resulting in depletion of the sperm membrane from GPI-anchored proteins. As shown in FIG. 1B and FIG. 2B, this treatment does not ablate the P4 sensitivity of CatSper, and in fact, slightly enhances it. This supports the idea that the P4 receptor is not a peripheral GPI-linked protein.

In order to determine to what P4 binds in human spermatozoa, a modified P4 analog (P4*) was designed that upon activation with UV light (312 nm) covalently attaches to its neighboring molecules (FIG. 1, FIG. 2C and FIG. 2D). This same compound also contains a biotin tag that allows for pull-down purification. P4* was tested in electrophysiological experiments; the data confirmed that it activates CatSper, and thus retains the ability to bind the sperm P4 receptor (FIG. 1A and FIG. 1B). Next, human spermatozoa were treated with P4*, followed by UV exposure to purify P4 binding proteins. After cell lysis, P4* bound molecules were enriched with streptavidin beads and subjected to polyacrylamide gel electrophoresis prior to one-dimensional LC-MS/MS identification (FIG. 1C). To determine the specificity of P4* binding, mock irradiated cells (no UV treatment, lane [−]) as well as cells treated in the presence of excess unlabelled P4 (specific P4 competition, lane [P]) were included as negative controls. To triage P4* positive bands, two similar steroids were used: estrogen (lane [E]), and synthetic progestin Ru486 (lane [R]) which it was shown previously (Lishko et al., 2011) do not interfere with P4 activation of CatSper. Competition with excess estrogen was used to determine whether P4* binding was the result of non-specific steroid interaction, and Ru486 competition removed genomic P4 receptor-like binding. Pull-down experiments revealed four distinct biotin-positive bands (lane [+], FIG. 1C); though, only the ~50 kDa band was present in both positive controls and absent or reduced from all negative controls.

Mass spectrometry analysis of protein bands ranging from ~40 kDa to 120 kDa resulted in hundreds of peptides. Unexpectedly, no CatSper channel subunits were identified from the six independent pull-down experiments. This suggests that the sperm P4 receptor is not likely a tightly associated component of the CatSper channel complex, but rather a separate, yet identified, molecule. With this information in hand, a search was performed for the candidate molecules that specifically bind to P4* and have a known function which may mediate the P4-dependent CatSper activation. This search was based on the following four criteria applicable to proteins identified by the mass spectrometry analysis: 1) the candidate should be present in all pull-down experiments except for negative controls; 2) it should be either a transmembrane protein with an extracellular domain, or a protein tightly associated with the outer leaflet of the sperm membrane; 3) the P4 receptor should not be GPI-linked, as CatSper retains its P4 sensitivity in sperm treated with PI-PLC (FIG. 1B and FIG. 2B); and 4) based on the absence of CatSper proteins in the pull-down samples, the P4 target is not a part of the CatSper complex and should function in bioactive lipid signalling or modifications that do not require second messengers such as ATP or calcium. The P4 target should function independently from CatSper with mSH activity, as the P4 effect on CatSper is fully reversible in the absence of exogenous energy sources (Lishko et. al, 2011, Smith et. al, 2013). The enzymatic changes imposed on mSH substrates can be removed in an energy-independent manner, unlike the effect of other serine protease or amidases. In addition, there were two more requirements: the P4 target should be expressed in sperm on the level of mRNA and protein to exclude epididymal-derived proteins, as testicular CatSper retains P4 sensitivity. Additionally, this molecule should be confined to the same cellular compartment as the CatSper channel. Finally, the P4 receptor should localize to the flagellum, because flagellar CatSper is P4 sensitive.

Selection of Candidate Proteins that Bind Progesterone

Based on the four initial criteria, examination of the identified proteins yielded three top candidates: fatty-acid amide hydrolase 1 (FAAH), alpha/beta hydrolase domain-containing protein 2 (ABHD2), and prostatic acid phosphatase which has a splice isoform that can exist as a membrane bound protein (TM-PAP) (FIG. 1D). The first two candidates are members of a large family of serine hydrolases, while the last candidate is an acid phosphatase. To test TM-PAP involvement, nascent CatSper current was recorded at extracellular pH=6.6 to induce TM-PAP activity and therefore mimic the potential effect of P4 on this protein. These recordings were compared to nascent CatSper current recorded at pH=7.4, and no apparent differences were observed (FIG. 4A-4B), suggesting that activation of TM-PAP is not sufficient for CatSper activation. In addition, activity of recombinantly expressed Tm-PAP is not altered by P4 or by addition of TmPAP-specific antibodies.

Figure 3A:
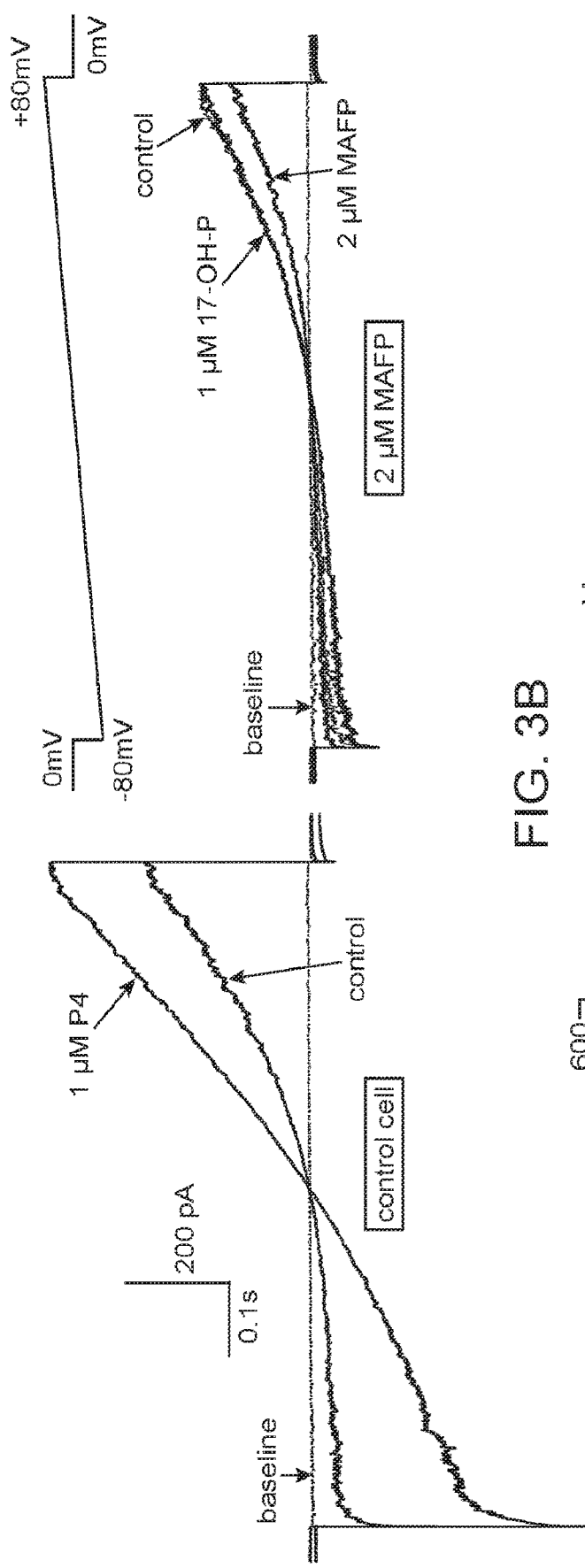
FIG. 3A-3C depict the effect of irreversible inhibition of sperm serine hydrolases on CatSper P4 sensitivity.
Figure 3B:
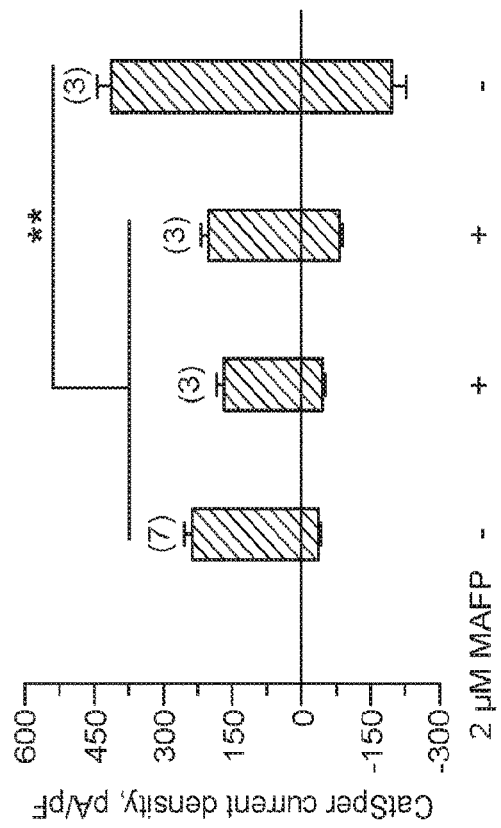
Figure 3C:
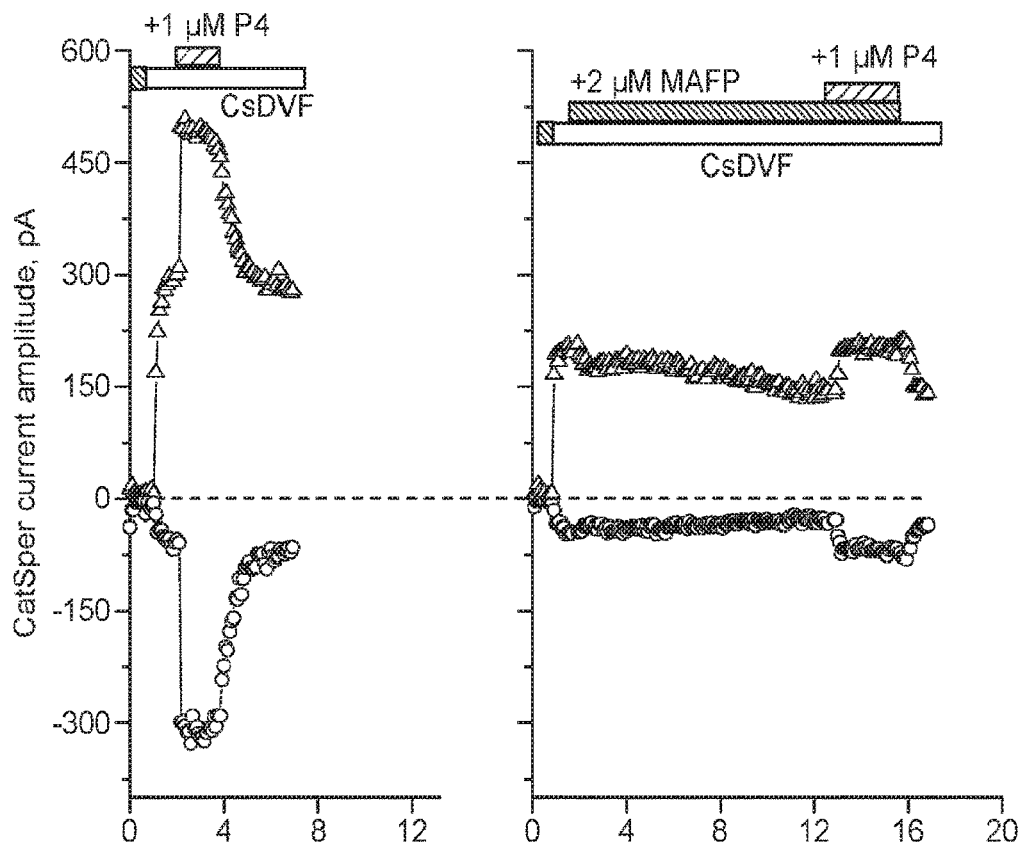
Figure 4A:
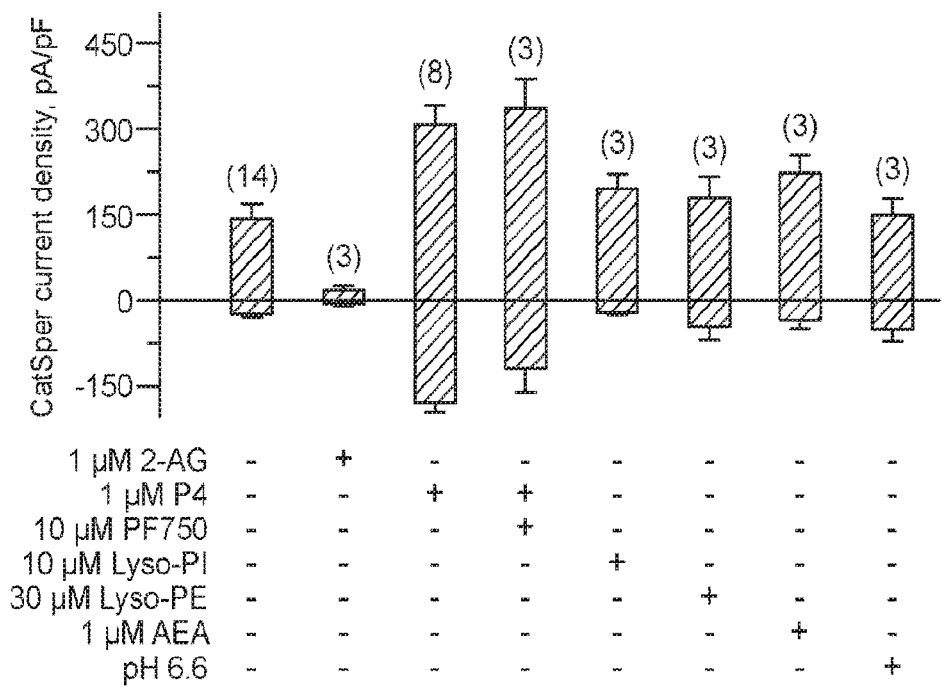
FIG. 4A-4B depict a pharmacological profile of human CatSper.
Figure 4B:
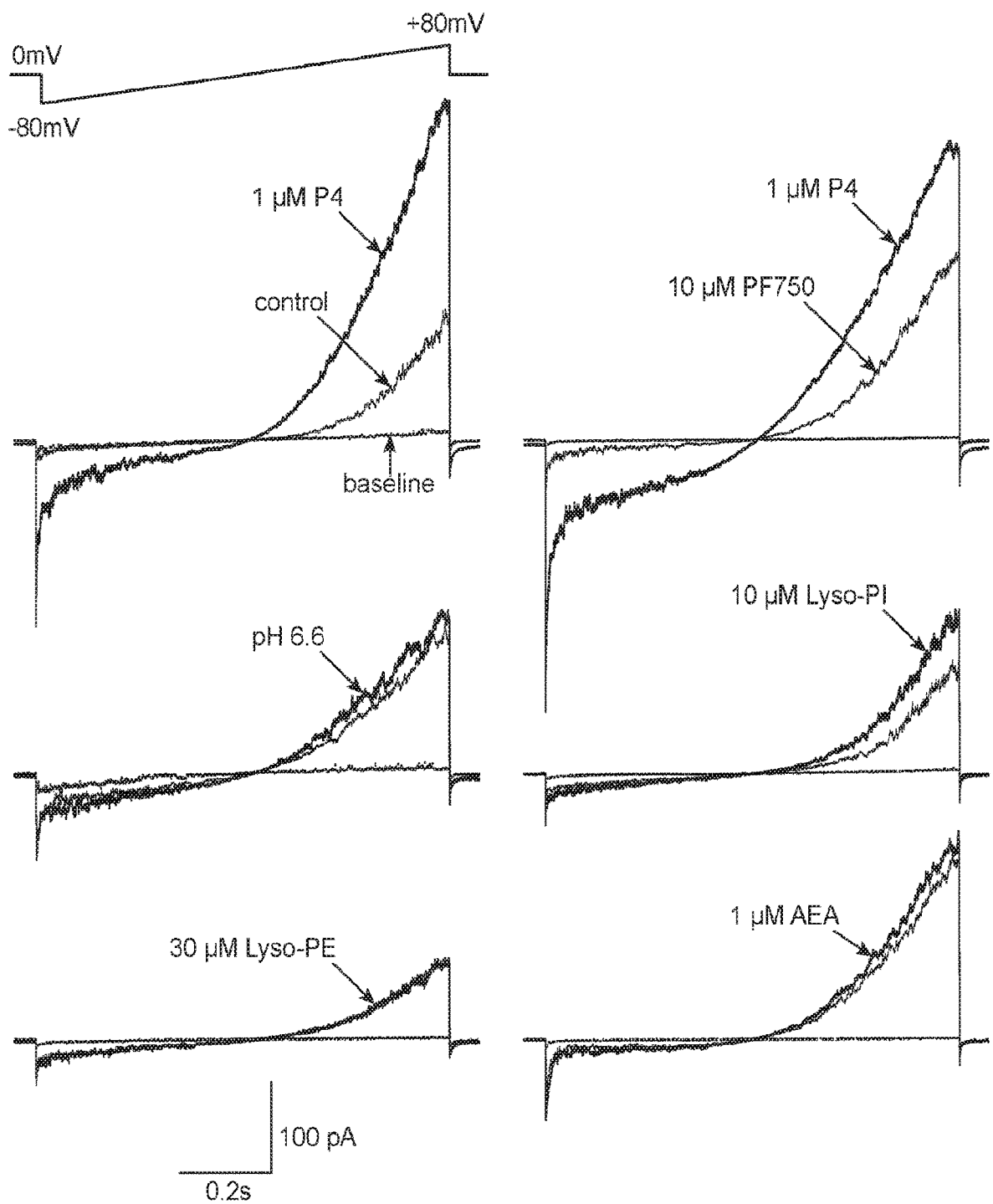
Figure 5A:
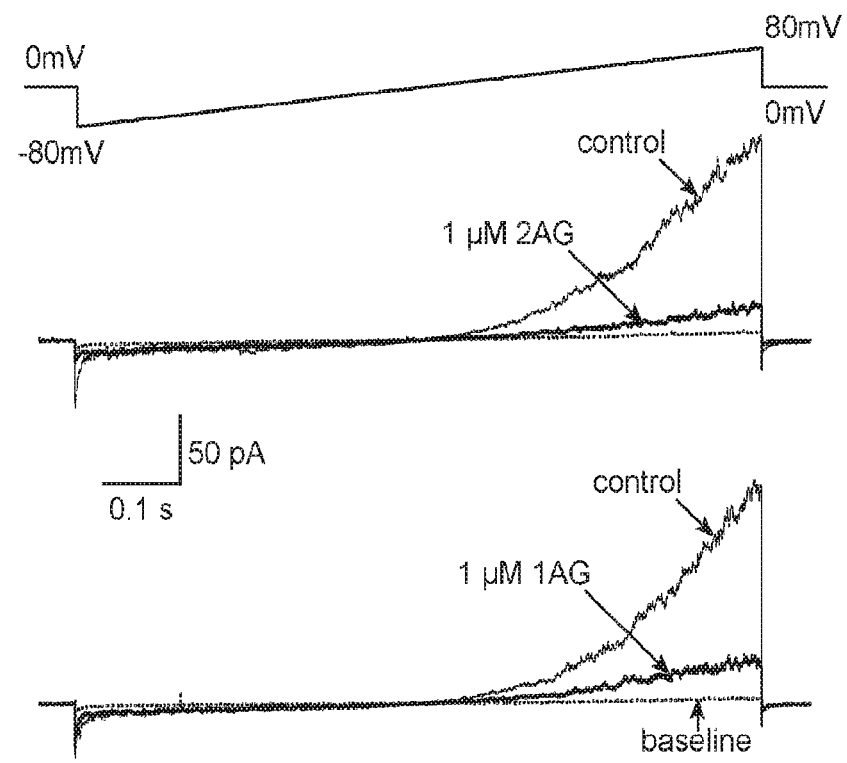
Figure 5B:
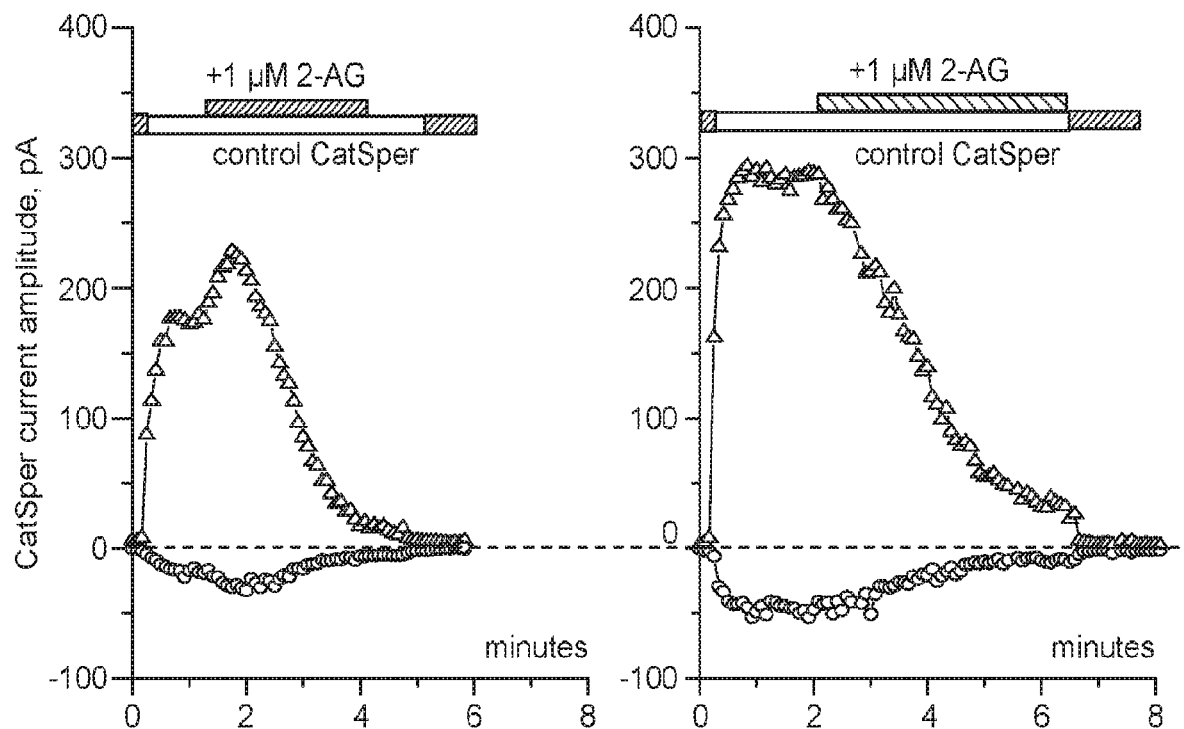

To test FAAH participation, CatSper activity was recorded from human spermatozoa before and after treatment with irreversible FAAH specific inhibitor PF750. This treatment did not change CatSper sensitivity to P4 (FIG. 4A-4B). Additionally, FAAH substrate anandamide (AEA), which should mimic P4 action if, in fact, FAAH is the P4 target, does not change nascent CatSper behaviour (FIG. 4A-4B). This suggests that neither activation, nor inhibition of FAAH activity affects CatSper, indicating the unlikely involvement of FAAH in P4-dependent CatSper activation. This is also consistent with the assumption that FAAH is located within intracellular membranes (Di Marzo et al., 2004), while the candidate, according to the aforementioned criteria, must have an extracellular P4 binding domain Serine Hydrolases are Involved in CatSper Activation by Progesterone ABHD2 is an obscure member of a superfamily of serine hydrolases (SH) that is comprised of more than 200 individual proteins (Bachovchin and Cravatt, 2012). Members of one subfamily of SH, a so-called metabolic SH, lack trypsin-like serine protease activity and instead chemically modify various small molecules, peptides or proteins (Bachovchin and Cravatt, 2012). They are widely expressed in multiple tissues, including the nervous system where they participate in degradation of phospholipids and endocannabinoids (Blankman et al., 2013; Blankman et al., 2007; Long and Cravatt, 2011; Savinainen et al., 2014). To examine the possible involvement of SH in P4-dependent activation of CatSper P4-induced channel activation was recorded in the absence or presence of irreversible SH inhibitor, methyl arachidonyl fluorophosphanate (MAFP). This treatment resulted in complete removal of P4-dependent activation of CatSper (FIG. 3A-3B), but showed no effect on basal CatSper activity (FIG. 3B), further supporting the idea that P4 acts through an independent signalling mechanism to stimulate CatSper activity and indicating the involvement of SH in this process. MAFP treatment ablated P4-induced motility changes, which further supports the idea that physiological P4 effects are a result of indirect activation of CatSper, however MAFP had no appreciable influence on prostaglandin E1 ($PGE_1$)-stimulated CatSper activation, which indicates a potential direct effect of $PGE_1$ on CatSper (FIG. 3B).

Figure 6B:
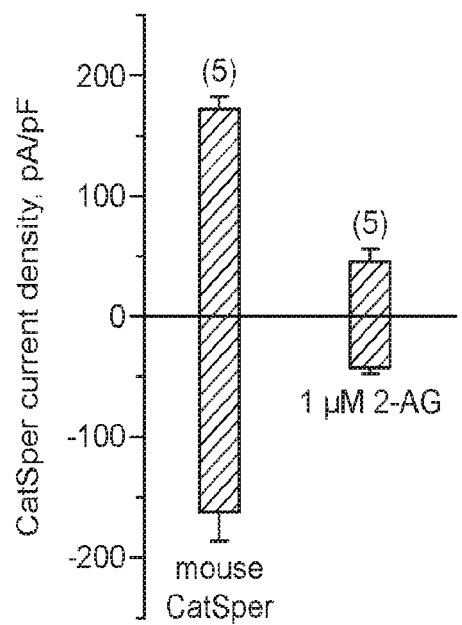

A substrate for ABHD2 enzyme activity has yet to be described, though this is not uncommon as substrates for almost half of metabolic SH remain elusive, with very few substrates being linked to lipid signaling pathways (Long and Cravatt, 2011). Two of the previously described SH substrates through which P4 signaling could act are the lysophospholipids or monoacylglycerols. These lipids were assessed for their potential involvement in CatSper regulation. Neither lysophosphatidylinositol (lyso-PI) nor lysophosphatidylethanolamine (lyso-PE) affected nascent CatSper current (FIGS. 4A and 4B), indicating that these lysophospholipids are unlikely involved in CatSper activation. The most studied among all monoacylglycerols are endocannabinoids 2-arachidonoylglycerol (2-AG) and 1-arachidonoylglycerol (1-AG) which were also shown to be substrates for many metabolic SH (Blankman et al., 2007). The family of endocannabinoids includes anandamide (AEA), oleamide (OEA), and monoacyl-glycerols: 2-arachidonoylglycerol (2-AG) and 1-arachidonoylglycerol (1AG). Application of either AEA or OEA had no effect, whereas 1AG and 2AG (AGs) inhibited ICatSper. Therefore, it was explored whether CatSper function is sensitive to these compounds. Application of either 1-AG or 2-AG revealed potent inhibitory action toward human CatSper channel (FIG. 5A-5D), with a percent inhibition of CatSper outward current of 92.4±3.5 and 85.0±0.5 for 2-AG and 1-AG, respectively; n=3. The efficacy of 2-AG towards mouse CatSper was slightly less with a percent inhibition of 73.9±4.4 against the outward current; n=5 (FIG. 6A-6B).

Figure 6C:
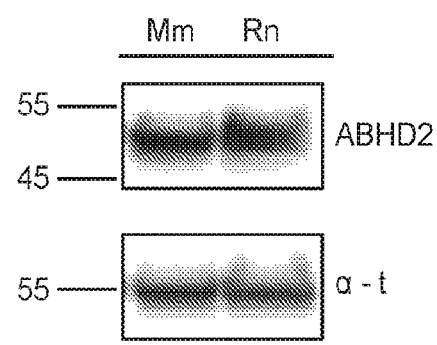
Figure 6D:
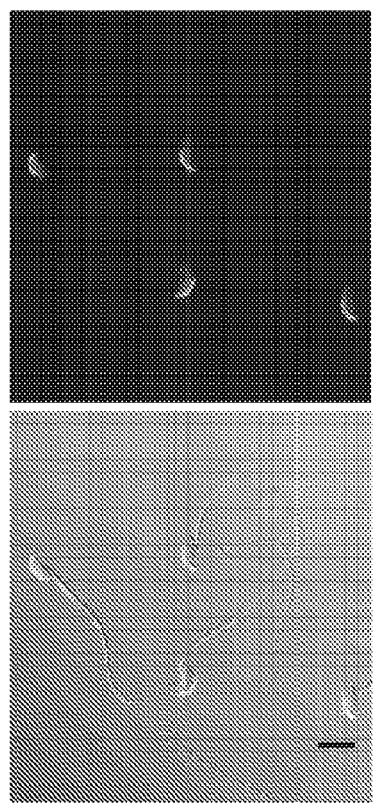
Figure 6E:
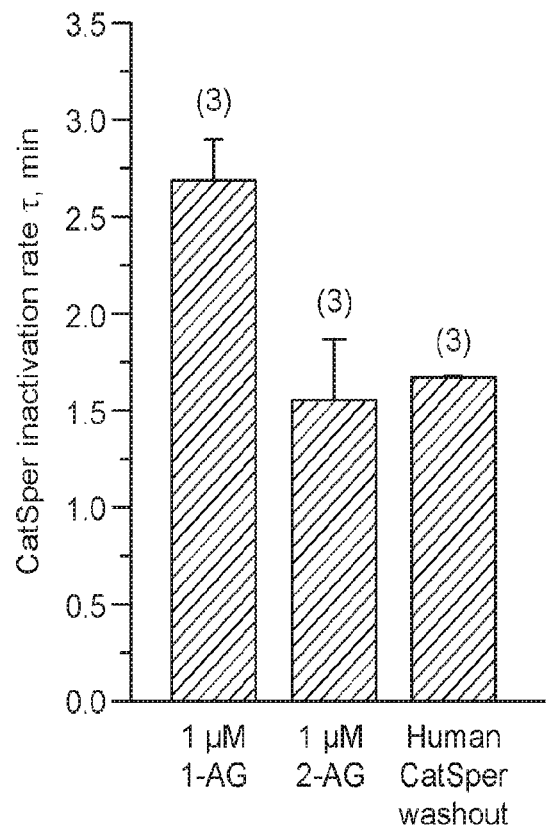

The compounds differ, however, in their rate of CatSper inactivation. 2-AG acts almost twice as fast as 1-AG when applied at the same concentration, with a decline in current amplitude of $\tau_{(2-AG)}$=1.6±0.3 min versus $\tau_{(1-AG)}$=2.7±0.2 min when 1 µM of lipid is applied under perfusion (FIG. 5D and FIG. 6E). When applied extracellularly, 2AG inhibits ICatSper with a median inhibitory concentration (IC50) of 350 nM for outward currents and 670 nM for inward currents. Intracellular application of 2AG could not mimic this effect, which highlights the importance of an extracellular pool of this lipid in the mechanism of action. Extracellular glycerol did not ablate ICatSper or its regulation by P4, which indicated that hydrophobic tails of AGs are likely responsible for their effect on ICatSper.

Regulation of CatSper Channel by Endocannabinoids

Figure 7A:
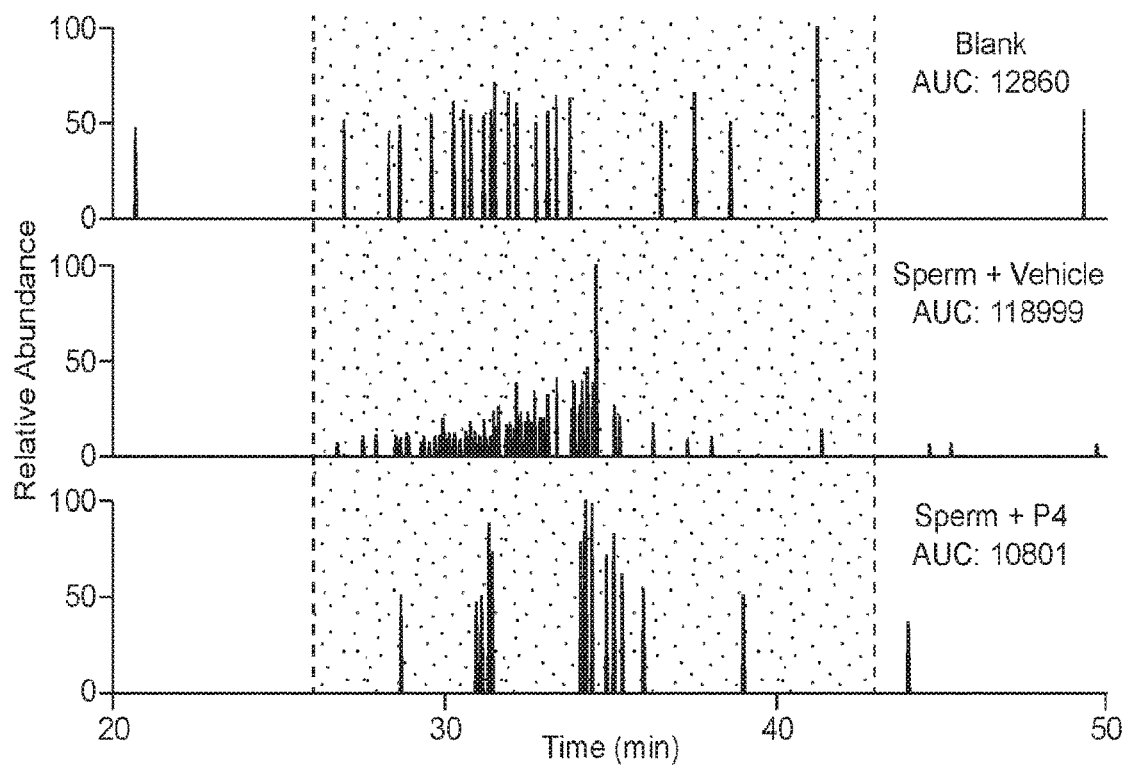
FIG. 7A-7C depict mass Spectrometry analysis of the lipids of sperm plasma membrane outer leaflet.
Figure 7B:
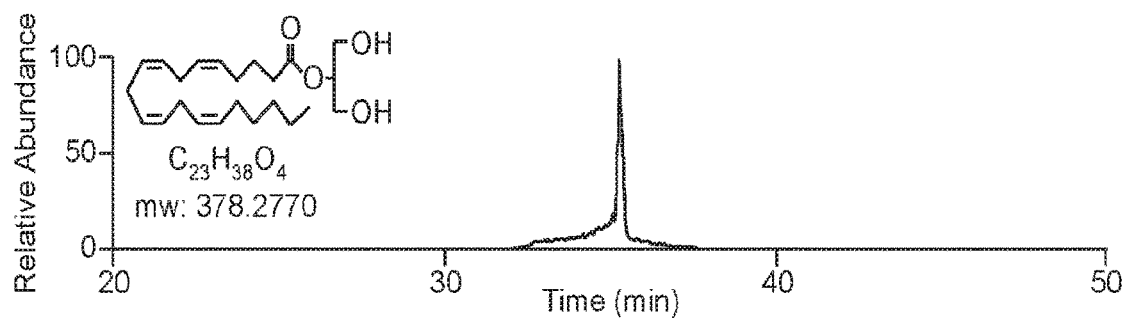
Figure 7C:
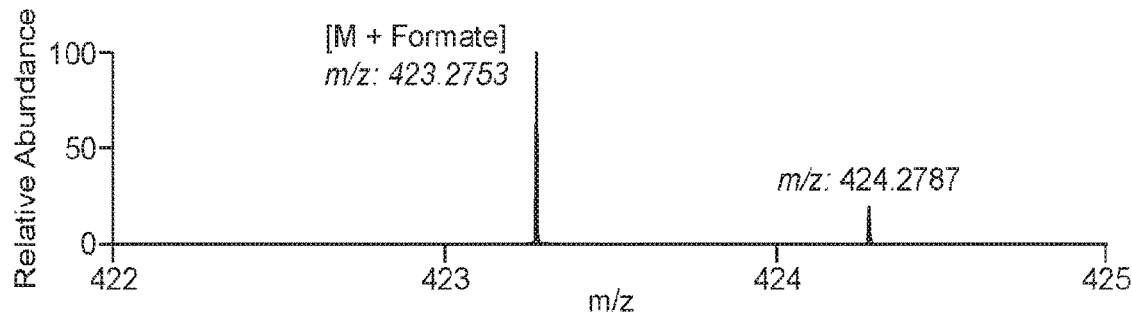

In order to identify whether 2-AG and 1-AG (AGs) are endogenous lipid regulator(s) of CatSper, selective lipid extraction from sperm plasma membrane was performed, followed by unbiased identification of lipids by liquid chromatography mass spectrometry (LC-MS). In order to selectively extract lipids from the outer leaflet of the plasma membrane a novel cyclodextrin-based lipid extraction protocol was developed that allows removal of steroids and single-tailed lipids, such as AGs, while leaving multi-tailed lipids in the membrane. Once extracted, the lipids are separated from the cyclodextrin via a hexane:isopropanol technique, and purified extracellular lipids are analysed using an LTQ-Orbitrap-XL mass spectrometer equipped with an ESI source and operated in the negative ion mode. To confirm the identity of the 2-AG ion, the synthetic compound was analysed under identical conditions as the isolated lipid mixtures. It was determined from the lipid standard that 2-AG occurs as a formate adduct ion, $[M+45\ Da]^-$, in negative ion ESI, with a chromatographic retention time in the range of 30-40 minutes (FIG. 7A-7C) Using these parameters, it was determined that spermatozoa initially possess relatively large amounts of extracellular AGs, after normalization to internal standards this corresponds to 240 fmol/sample (of roughly 30 million cells) which decreases ~6-fold upon P4 treatment (FIG. 5E and FIG. 7C). Taking into account the dimensions of human sperm flagellum, 45 µm×0.5 µm, the concentration of AGs in the extracellular leaflet of an individual spermatozoon could easily reach at least 0.7 µM. Upon P4 treatment, AG content decreases to that observed in cell-free controls (FIG. 7A-C). The results show that these endocannabinoids are detected in the outer leaflet of the sperm plasma membrane and their content is drastically reduced upon P4 stimulation. Thus, P4 appears to act through mSHs to deplete AGs in plasma membrane, which leads to CatSper activation.

ABHD2 is a Progesterone-Activated Lipid Hydrolase

Figure 8A:
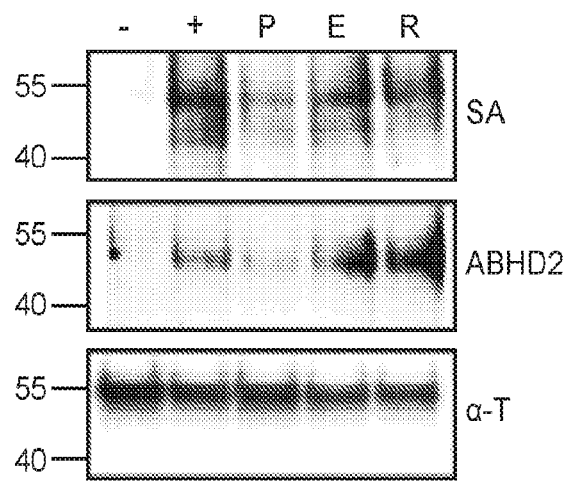
FIG. 8A-8D depict ABHD2 expression in primate spermatozoa.

Finally whether ABHD2, the SH-like enzyme identified as a candidate for the sperm P4 non-genomic receptor in the pull-down experiment, has the ability to hydrolyze AGs was assessed. In the pull-down experiments, ABHD2 was specifically detected in all lanes, except for negative controls, where ABHD2 signal was absent or reduced (FIG. 8A). It was also tested whether ABHD2 meets the last two requirements: is functionally expressed in sperm on the level of mRNA and protein, and is confined to the same cellular compartment as the CatSper channel. Antibodies (Abs) against ABHD2 (AbAs) detected the protein in spermatozoa of various mammalian species: humans, boar, bovine, mouse, and rat. ABHD2 transcripts are abundant in sperm, as evidenced by unbiased RNA deep sequencing of human spermatozoa and reverse transcription polymerase chain reaction experiments. To confirm that ABHD2 binds P4, a P4* binding assay was carried out using recombinantly expressed ABHD2. Positive streptavidin staining revealed that ABHD2 binds P4* specifically and in a UV-dependent manner, and this binding is competed off by excess unlabelled P4. Additionally, when human spermatozoa were incubated with AbAs, the result was a significant decrease of the CatSper activation by P4, whereas sperm treated with nonspecific antibodies retained their P4 sensitivity. These results indicate that human ABHD2 is expressed in the sperm flagellum and is actively involved in P4-dependent signalling.

Figure 14A:
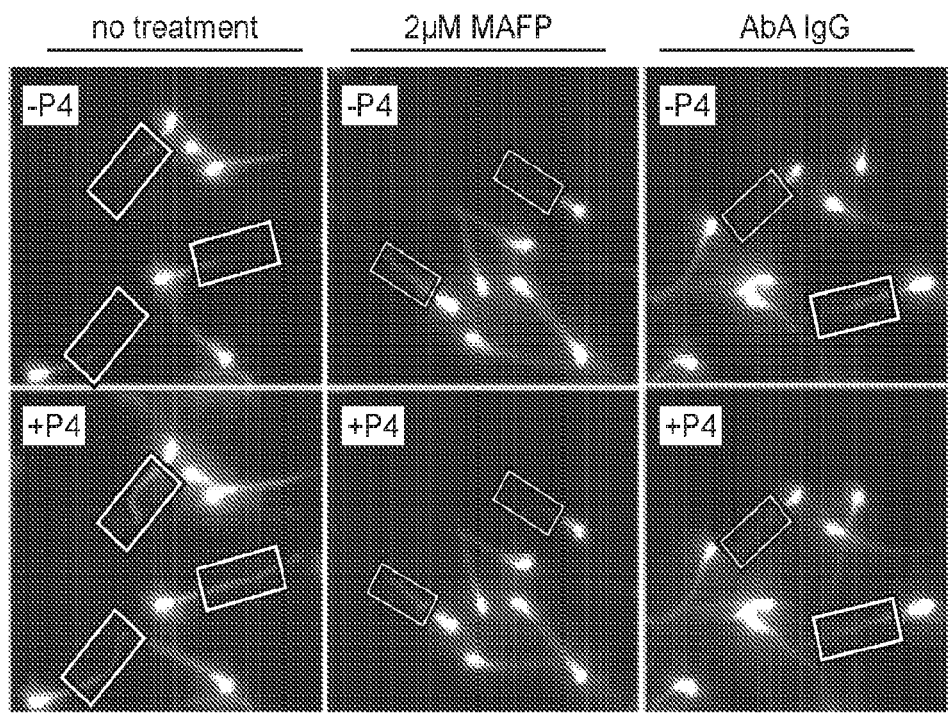
FIG. 14A-14D depict data showing ABHD2 regulates $Ca^{2+}$ influx in human flagellum and is involved in mouse acrosome reaction.
Figure 14B:
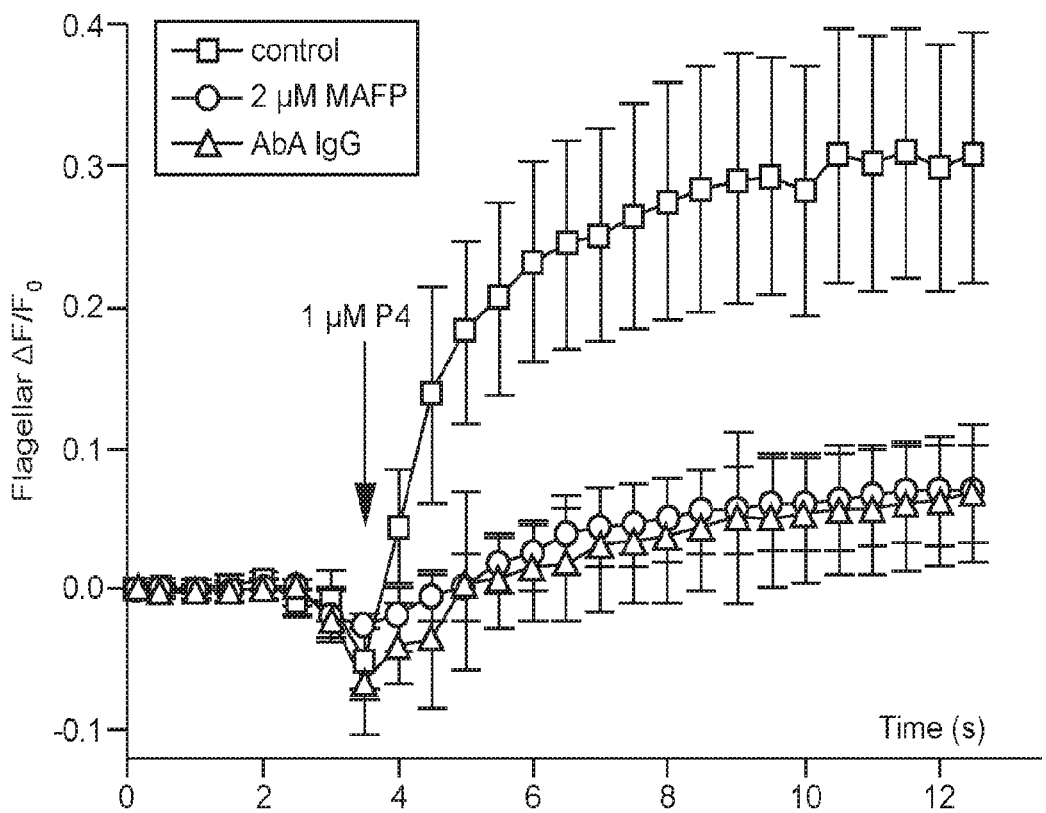

Next, human ABHD2's enzymatic activity was explored. Because the lipid MS data showed a P4-dependent decrease in sperm AGs, recombinant ABHD2 was examined to determine if it could hydrolyze AGs. Such hydrolysis results in the formation of glycerol and arachidonic acid (AA), free glycerol production was monitored as an indicator of ABHD2 activity and mock-transfected cells or recombinant ABHD12 were used as controls, which was another mSH with known activity toward AGs. ABHD2 revealed modest hydrolase activity unless supplemented with 0.5 mM P4. P4 significantly enhanced ABHD2 activity, whereas it had no significant effect on ABHD12. Additionally, ABHD2 was tested to see if it is responsible for P4-induced calcium influx in sperm flagella. Inactivation of ABHD2 with protein-specific antibodies or sperm exposure to MAFP both abolished P4-activated calcium influx into sperm flagella. FIGS. 14A and 14B.

Figure 8B:
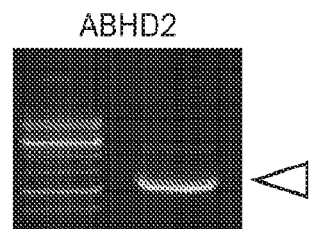
Figure 8C:
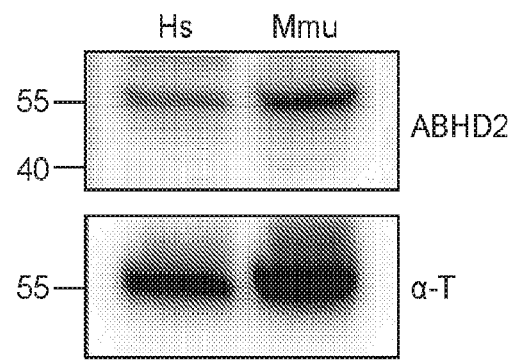
Figure 8D:
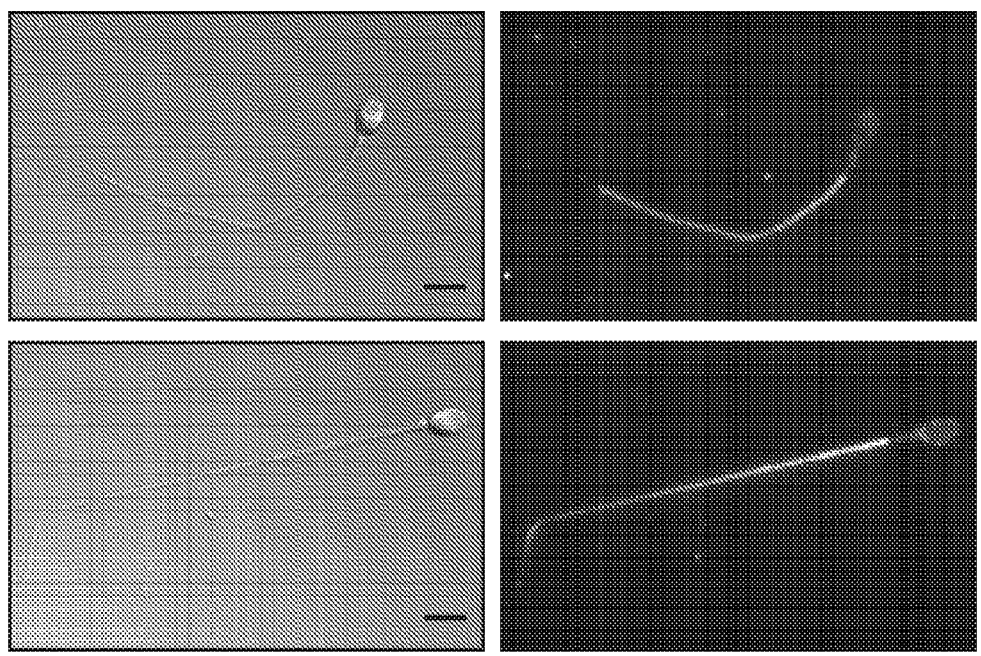
Figure 9A:
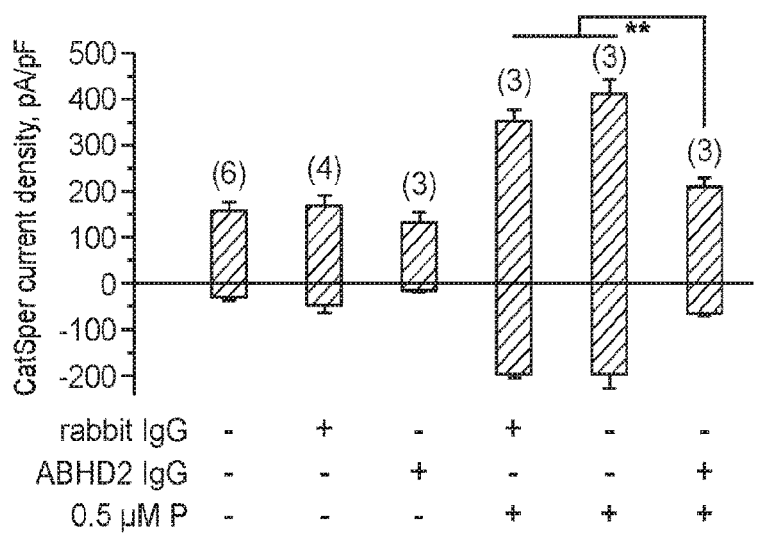
FIG. 9A-9D depict data showing that ABHD2 is a progesterone dependent lipid hydrolase.
Figure 9B:
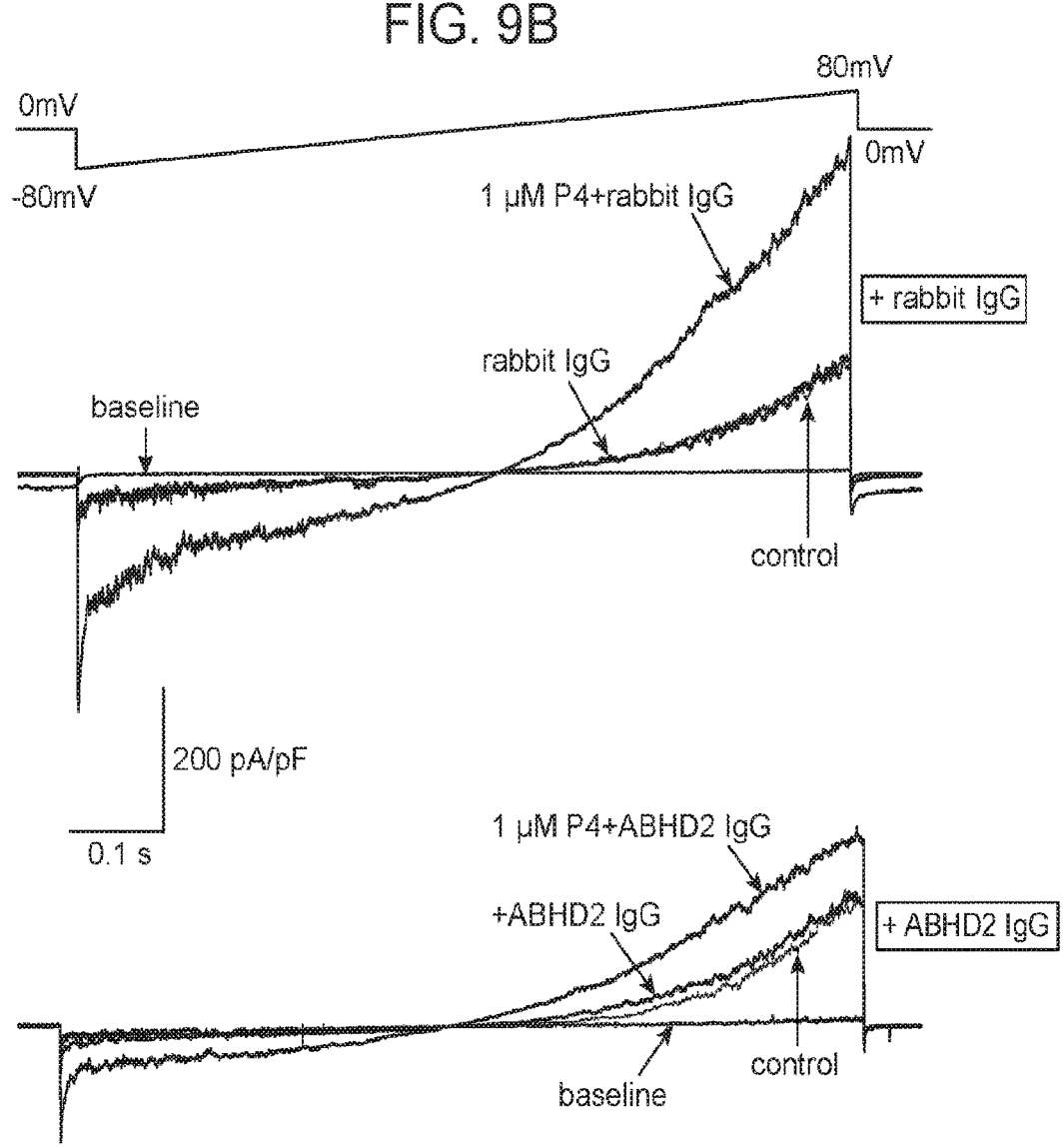

ABHD2 transcripts were present in human sperm (FIG. 8B) and anti-ABHD2 antibodies also detected the protein in human sperm flagellum (FIG. 8D). ABHD2 expression was also detected in sperm lysates of both primate species that have electrophysiologically confirmed P4-dependent activation of CatSper: human and macaques ((Sumigama S., 2015) and FIG. 8C). Additionally, incubation of human spermatozoa in the presence of ABHD2 antibodies resulted in significant decrease of the P4 activation of CatSper (FIGS. 9A and 9B). In contrast, human spermatozoa incubated with non-specific rabbit antibody under the same conditions retained their P4 sensitivity (FIGS. 9A and 9B). This suggests that human ABHD2 is not only expressed in the same cellular compartment as CatSper, but is also actively involved in P4-dependent signaling.

ABHD2 is Present in Rodent Acrosome

Figure 14C:
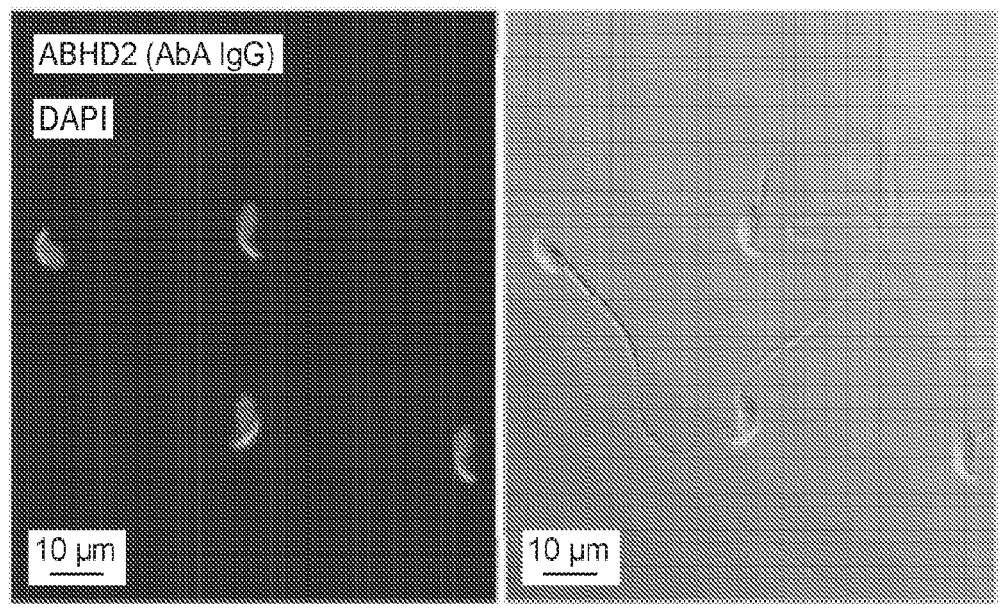
Figure 14D:
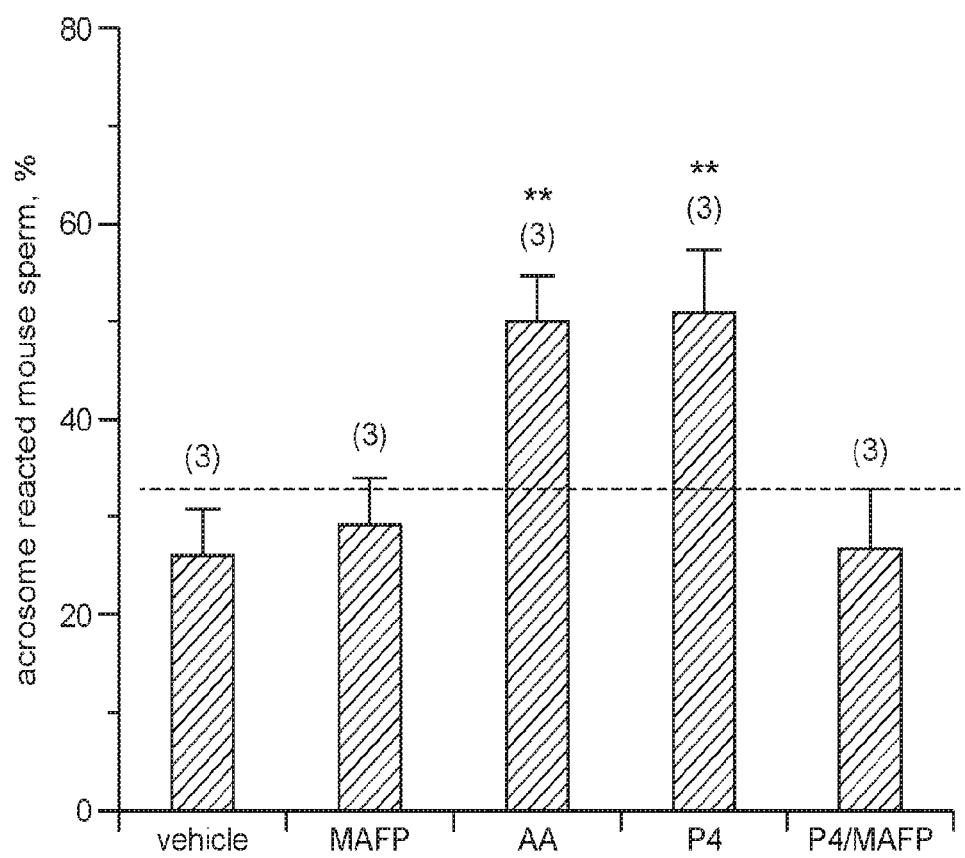

ABHD2 expression was also detected in epididymal sperm cells isolated from two rodent species: mouse and rat (FIGS. 6C and 14C). Based on a previous report (Lishko et al., 2011), murine CatSper is insensitive to P4 activation and therefore may lack ABHD2-dependent regulation. Murine and human ABHD2 proteins share a high degree of sequence similarity; however, their subcellular localizations in sperm are different. Unlike human, murine ABHD2 is restricted to the acrosomal region, and is absent from the flagellum (FIGS. 6D and 14C). This may explain the absence of murine flagellar CatSper sensitivity toward P4. Based on the ABHD2 localization in acrosome, it is possible that P4 activation of ABHD2 and consequent AA release could be required for AR. Both P4 and AA stimulate mouse AR to similar levels, whereas MAFP blocks the P4 effect. FIG. 14D. This suggests that mouse AR is dependent on mSH action and that ABHD2 may play a role in this process. 2-AG also inhibits mouse ICatSper but with less efficacy than it inhibits human ICatSper. Murine sperm gradually lose 2-AG content as they travel through the epididymis, and high activity of monoacylglycerol AG hydrolase, the lipase MAGL, contributes to low resting AG levels. Thus, murine CatSper is no longer inhibited by endogenous AGs and, therefore, does not require P4 stimulation. In contrast, human spermatozoa retain substantial amounts of AGs, which keep CatSper shut and, thus, require ABHD2 to eliminate AGs upon P4 exposure. As ABHD2 degrades AGs and activates CatSper, the human sperm membrane must also have a feedback mechanism for CatSper inactivation. The sperm plasma membrane constantly produces AGs in order to keep CatSper closed. P4 application produced prolonged CatSper activation that slowly returns to basal levels when P4 is removed from the external solution. The rate of this "washout" matches precisely the rate of 2-AG inhibition, which supports the idea that human sperm cells constantly make AGs and that slow "washout" of P4 activation reflects the time-dependent replenishment of 2-AG.

Figure 9C:
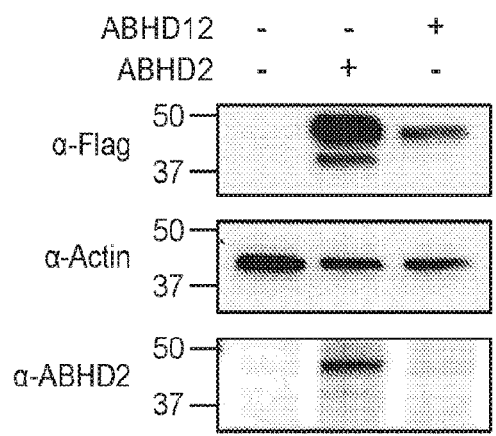
Figure 9D:
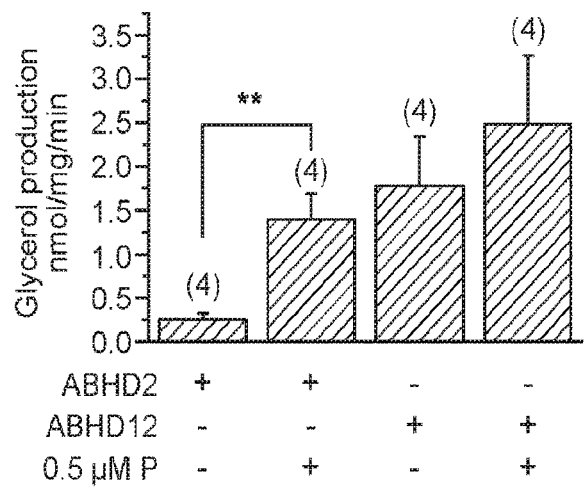

The enzymatic activity of human ABHD2 was explored. Hydrolysis of AGs results in the formation of glycerol and arachidonic acid (AA) (Blankman et al., 2007). In order to monitor ABHD2 hydrolase activity, an assay capable of quantifying free glycerol production (Navia-Paldanius et al., 2012) was carried out. ABHD2 was cloned from a cDNA library generated from purified human spermatozoa and heterologously expressed (FIG. 9C). As controls, mock-transfected cells or heterologously expressed ABHD12, another SH with known activity toward AGs (Blankman et al., 2007) (FIG. 9C), were used. ABHD2 revealed very modest AG hydrolase activity unless supplemented with 1 µM P4 (FIG. 9D). P4 significantly enhanced ABHD2 activity, while having no significant effect on ABHD12 (FIG. 9D). These data support the hypothesis that P4 influences ABHD2 activity.

Figure 10A:
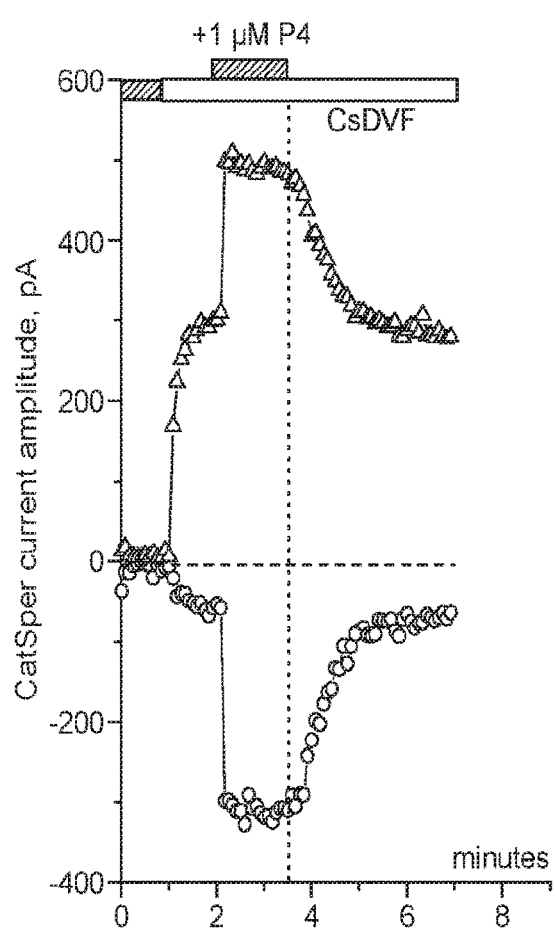
FIG. 10A-10B depict the effect of human sperm membrane on endogenous CatSper inhibitor.
Figure 10B:
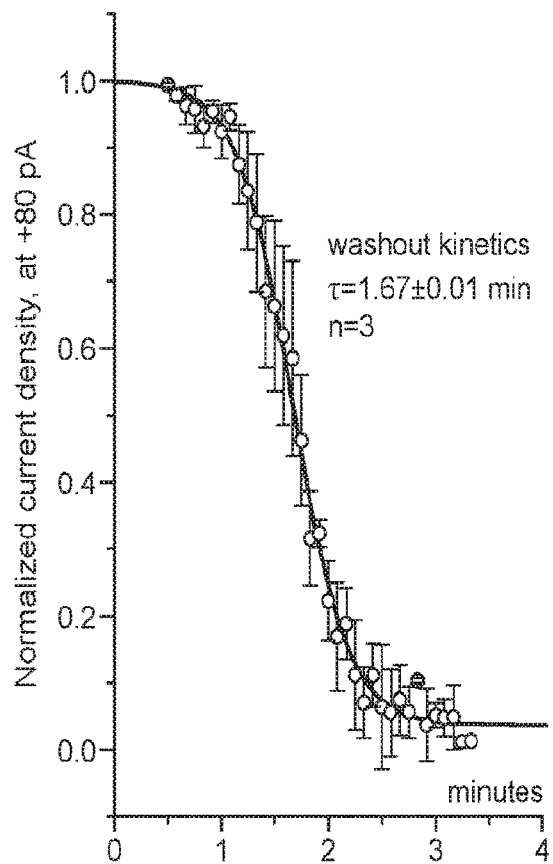
Figure 11:
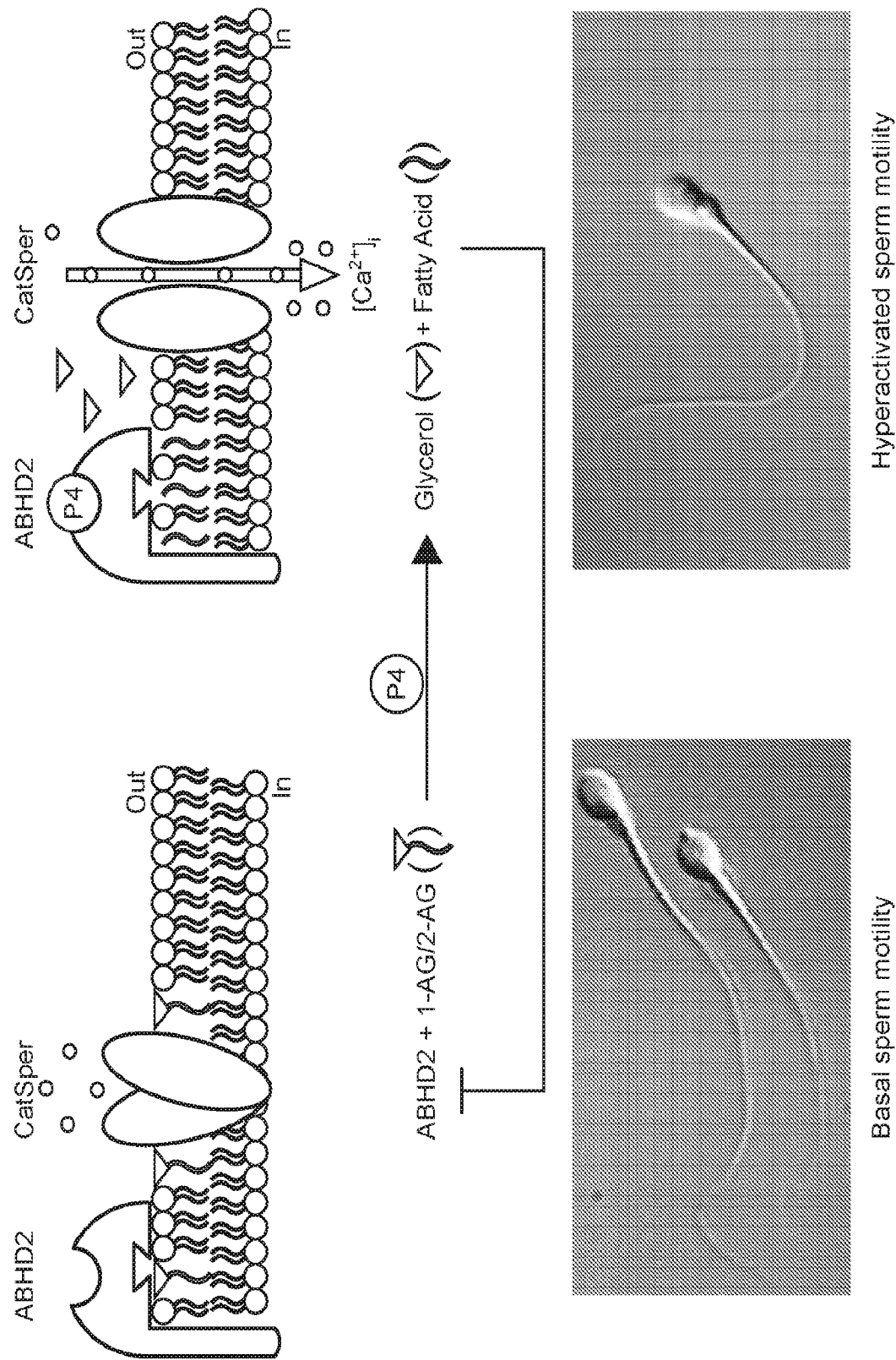
FIG. 11 depicts a model of non-genomic progesterone signalling in human sperm cells.

If ABHD2 indeed degrades AGs in a P4-dependent manner, activating CatSper by degrading its endogenous inhibitor, then the sperm membrane must constantly produce AGs in order to keep CatSper in a closed state. As indicated above, P4 application produced prolonged CatSper activation that slowly washes out (FIG. 10A-10B). The rate of this "washout" exactly matches the rate of 2-AG inhibition (FIG. 5B, FIG. 5D, and FIG. 6E), supporting the idea that human sperm cells constantly produce extracellular AGs and the slow "washout" of the P4 effect is due to the time dependent replenishment of 2-AG. Thus, a recovery of CatSper activity upon removal of P4 occurs exactly at the same rate as 2-AGs inhibition of CatSper (FIG. 6E).

Human ABHD2 is a 425 amino acid molecule with a predicted transmembrane domain that is positioned between amino acids 10 and 30, followed by a large extracellular facing domain This fulfils two of the first four requirements for the sperm non-genomic P4 receptor. ABHD2 participates in bioactive lipid signalling by hydrolysing AGs in a P4-dependent manner and was initially identified as a candidate protein from the pull-down experiments. ABHD2 participates in bioactive lipid signalling by hydrolyzing AGs in a P4-dependent manner, so they act as true mSHs. ABHD2 is functionally expressed in sperm and is confined to the same cellular compartment as the CatSper channel. Taking into account that a) ABHD2 is the only candidate molecule which meets all six search requirements and b) modulation of its function by pharmacological perturbation disrupts the P4 signalling in sperm and impairs sperm activation, it is concluded that the serine hydrolase ABHD2 is the nongenomic progesterone receptor of sperm.

FIG. 1A-1D.

Progesterone (P4) and its synthetic analog P4* activate human CatSper channel. (A) Representative whole-cell CatSper currents (ICatSper) recorded from spermatozoa in the absence (black) and presence of either P4 (red) or P4* (green). (B) ICatSper densities recorded at +80 mV (positive scale) or −80 mV (negative scale) extracted from ramps shown in (a) and FIG. 2A-2B. (C) Representative western blot from P4* binding experiments resolves biotinylated (P4* bound) proteins. Lanes are: [(−); mock-irradiated cells], [(+); UV-treated cells], [(P); 20 mM P4] [(E); 0.5 mM estrogen] and [(R); 0.5 mM Ru486]. All experiments were performed in the presence of 250 nM of P4*. Acetylated tubulin staining was used as loading control. (D) Proteomic analysis of ~50 kDa band; one experiment of six is shown.

FIG. 2A-2D. P4* is instrumental in identifying sperm progesterone binding proteins.

(A) Representative $I_{CatSper}$ recorded from human spermatozoa in the absence (black) and in the presence of 17-OH—P (blue). (B) Representative CatSper currents and their P4 sensitivity recorded from control human spermatozoa (left panel) and spermatozoa treated with 5 U of PI-PLC (right panel). (C) Photoreactive P4 analog (P4*) consists of an active group (progesterone), diazirine-UV-sensitive moiety, and a biotin tag that allows for pull-down of bound proteins. (D) UV-activated chemical reaction involving diazirinyl moiety is shown.

FIG. 3A-3C.

Irreversible inhibition of sperm serine hydrolases results in removal of CatSper P4 sensitivity. (A) Representative ICatSper recorded from control human spermatozoa in the absence (black) and presence of P4 (red; left panel). ICatSper recorded from human spermatozoa treated by irreversible serine hydrolase inhibitor, methyl arachidonyl fluorophosphanate (MAFP, right panel). (B) ICatSper current densities recorded at +80 mV (positive scale) or −80 mV (negative scale) extracted from ramps shown in (a). Statistical significance indicated by (**, p≤0.01) for both inward and outward ICatSper. (C) ICatSper amplitudes recorded at +80 mV (triangles) and −80 mV (circles) plotted against time.

FIG. 4A-4B. Pharmacological profile of human CatSper.

(A) $I_{CatSper}$ current densities recorded at +80 mV (positive scale) or −80 mV (negative scale) extracted from ramps shown in (B). Recordings were performed in the absence or presence of indicated compounds. (B) Representative CatSper sensitivity to indicated compounds and treatments.

FIG. 5A-5E.

Endogenous cannabinoids are potent inhibitors of CatSper current. (A) Representative ICatSper recorded from human spermatozoa in the absence (black) and in the presence of corresponding endocannabinoid: 2-AG (red) or 1-AG (blue). (B) ICatSper amplitudes recorded at +80 mV (triangles) and −80 mV (circles) as shown in (a) and plotted against time. (C) Average ICatSper current densities obtained at +80 mV (positive scale) or −80 mV (negative scale). Statistical significance indicated by (**, p≤0.01 and *, p≤0.05). (D) Representative rates of ICatSper inactivation upon application of endocannabinoids. (E) Endocannabinoid content of sperm plasma membrane outer leaflet as measured by lipid mass spectrometry.

FIG. 7A-7C. Mass Spectrometry analysis of the sperm plasma membrane outer leaflet.

(A) Extracted ion chromatogram (EIC) between 20-50 minutes of full mass spectra acquisition for lipid extracts showing the relative abundance of m/z=423.2754±0.006. Lipids were extracted by beta-cyclodextrin treatment of live sperm cells in the absence (middle) or presence (lower) of P4*. The upper panel indicates the EIC for beta-cyclodextrin alone (blank). The peaks between time 27-43 minutes were integrated to obtain area under the curve (AUC) (B) Shown is the EIC for 50 nmol of synthetic 2-AG showing a retention time of 35.3 minutes. (C) Electrospray Ionization mass spectra reveals the formation of a formate adduct as the major ionization product of 2-AG when acquired in the negative ion mode. This m/z was used to assess 2-AG presence in experiments mentioned above. Note that in these experiments it was not differentiated between the 1-AG and 2-AG stereoisomers based on either m/z or retention time.

FIG. 6A-6E.

Endocannabinoids are inhibitors of mammalian CatSper. (A) Representative ICatSper recorded from mouse spermatozoon in the absence (black) and in the presence of 2-AG (green). (B) Current densities of mouse ICatSper recorded at +80 mV (positive scale) or −80 mV (negative scale) in the absence or presence of 2-AG. (C) ABHD2 protein is detected in murine (Mm) and rat (Rn) sperm lysates. (D) Immunostaining of mouse spermatozoa with anti-ABHD2 antibody shows acrosomal localization of the protein (green fluorescence; left panel). Corresponding overlay with DIC images of the same cells is included on right; scale bars are 10 mm Nuclei were stained by DAPI. Mouse spermatozoa were isolated from cauda epididymis. (E) The rates of ICatSper inactivation upon addition of endocannabinoids or removal of P4 (CatSper washout). The mean rates were obtained from (n) independent experiments.

FIG. 10A-10B. Human sperm membrane is able to replenish endogenous CatSper inhibitor.

(A) $I_{catSper}$ amplitudes when plotted over time show slow $I_{catSper}$ inactivation upon removal of P4. (B) The rate of $I_{catSper}$ inactivation (washout) after removal of P4 was calculated as mean±SEM extracted from $I_{catSper}$ densities obtained at +80 mV. Mean rates were obtained from three independent experiments.

FIG. 8A-8D.

ABHD2 expression is shared among primate spermatozoa. (A) Representative western blot shows ABHD2 presence in pull-down experiments (human sperm treatment and labels are the same as shown in FIG. 1C: [(+); UV-treated cells], [E; estrogen] and [R; Ru486]), and absence from all negative controls [lanes (−) and (P)]. (B) Amplification of abhd2 from human sperm cDNA library reveals a band corresponding to the full-length ORF. (C) Immunostaining of human spermatozoa with anti-ABHD2 antibody (right panel) and corresponding DIC images of the same cells (left); scale bars are 5 mm (D) ABHD2 protein is detected in human (Hs) and monkey (Mmu) sperm lysates.

FIG. 9A-9D.

ABHD2 is progesterone dependent lipid hydrolase. (A) ICatSper current densities recorded at +80 mV (positive scale) or −80 mV (negative scale) extracted from ramps shown in (B). ICatSper were recorded from control human spermatozoa or sperm treated with 1:100 dilutions of either nonspecific rabbit IgG or anti-ABHD2 antibody for at least 30 minutes. Statistical significance indicated by (**, p≤0.01) for both inward and outward ICatSper. (B) Representative ICatSper recorded from human spermatozoa treated with rabbit IgG or anti-ABHD2 antibody. (C) Expression of recombinant ABHD2 and ABHD12 in CHO cells. (D) Monoacylglycerol hydrolysis by recombinant ABHD2 and ABHD12 in the presence or absence of P4.

FIG. 11.

Model of non-genomic progesterone signaling in human sperm cells. Progesterone (P4) binds to its non-genomic receptor (ABHD2) and activates its hydrolysis of endocannabinoid 2-AG. Basal levels of 2-AG inhibit sperm calcium channel CatSper. Once 2-AG is metabolized into glycerol and arachidonic acid (AA), CatSper inhibition is lifted and Ca2+ enters the cytoplasm. Elevation of [Ca2+] in the flagellum leads to sperm motility hyperactivation. The latter helps sperm overcome the egg's protective vestments and leads to fertilization. AA, a product of ABHD2 hydrolysis, may act as negative regulator of ABHD2 enzymatic activity.

Figure 12A:
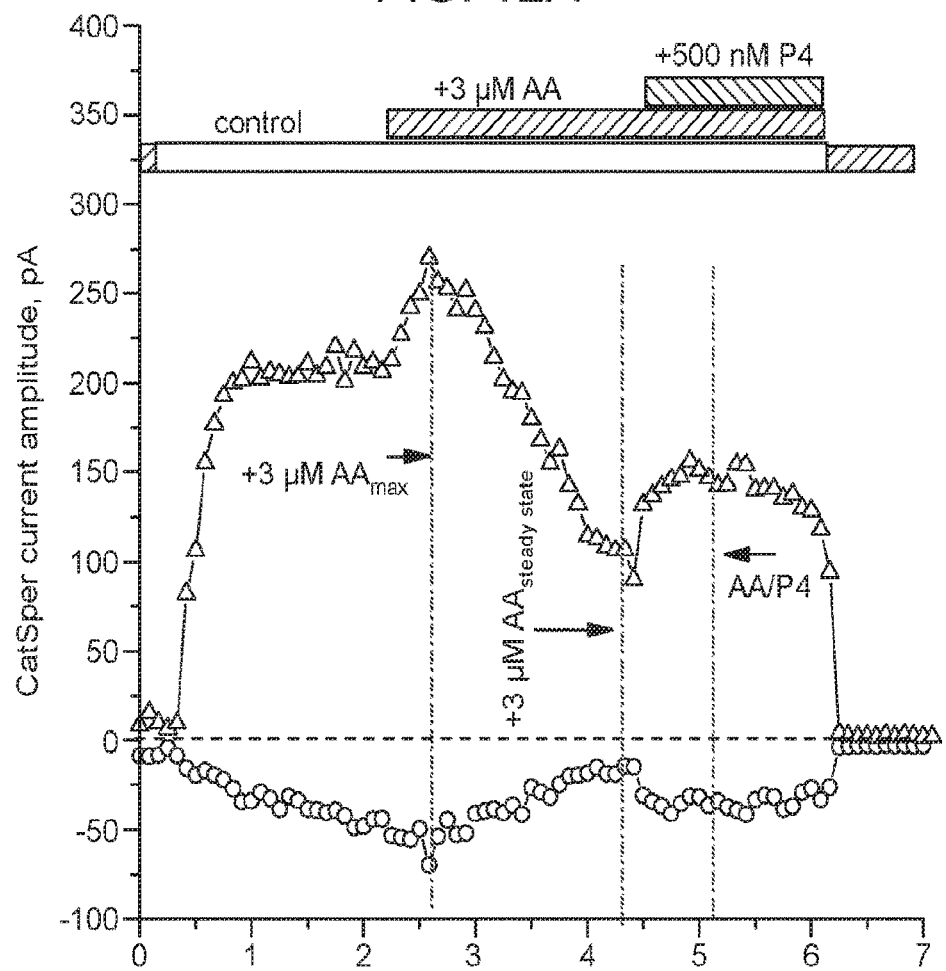
FIG. 12A-12B depict data showing that arachidonic acid acts as a dual regulator of CatSper.
Figure 12B:
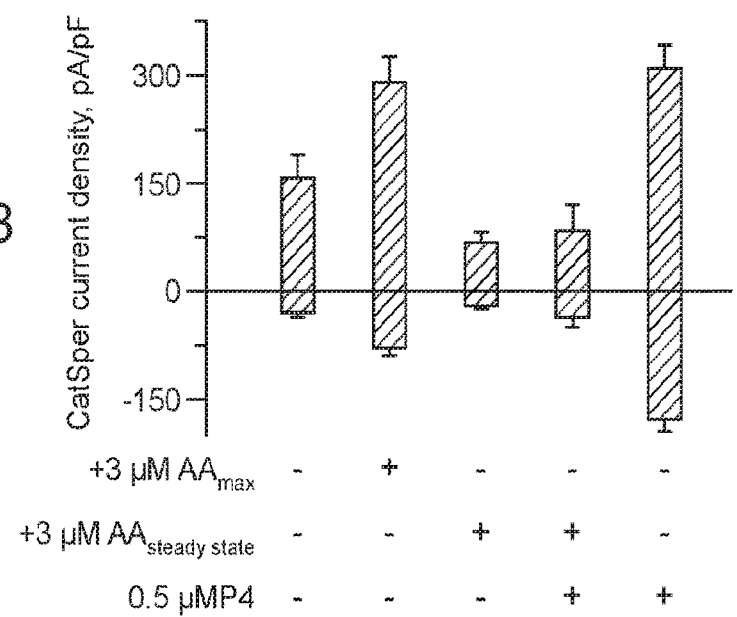

FIG. 12A-12B. Arachidonic Acid Acts as a Dual Regulator of CatSper.

(A) $I_{catSper}$ amplitudes recorded at +80 mV (triangles) and −80 mV (circles) were plotted against time to show time-dependent AA effect towards CatSper and removal of P4 activation. (B) $I_{catSper}$ densities recorded at +80 mV (positive scale) or −80 mV (negative scale) extracted from 3 independent experiments.

FIG. 14A-14D. ABHD2 Regulates $Ca^{2+}$ Influx in Human Flagellum and is Involved in Mouse Acrosome Reaction.

(A) Representative images from calcium imaging experiments before and after P4 treatment with regions of interest (ROIs) indicated. (B) Preincubation with either MAFP or AbA impeded P4-induced calcium influx. ΔF/F, the change in intensity from the original intensity before stimulation. Between 40 and 60 sperm flagella were assessed per condition. (C) Immunostaining of mouse cauda epididymal spermatozoa with AbA shows acrosomal localization. (Right) An overlay with differential interference contrast (DIC) images. Nuclei were stained by 4', 6-diamidino-2-phenylindole (DAPI). (D) Percentage of AR murine spermatozoa in response to indicated treatments. Live, capacitated mouse spermatozoa were incubated with 3 μM P4, 3 μM AA, 2 μM MAFP, or vehicle (ethanol), after which they were imaged for the presence of intact acrosome. Data are represented as means±SEM; numbers in parentheses indicate number of experiments; and **P<0.005.

REFERENCES

Bachovchin, D. A., and Cravatt, B. F. (2012). The pharmacological landscape and therapeutic potential of serine hydrolases. Nature reviews Drug discovery 11, 52-68.

Baldi, E., Casano, R., Falsetti, C., Krausz, C., Maggi, M., and Forti, G. (1991). Intracellular calcium accumulation and responsiveness to progesterone in capacitating human spermatozoa. J Androl 12, 323-330.

Blackmore, P. F., Beebe, S. J., Danforth, D. R., and Alexander, N. (1990). Progesterone and 17 alpha-hydroxyprogesterone. Novel stimulators of calcium influx in human sperm. J Biol Chem 265, 1376-1380.

Blankman, J. L., Long, J. Z., Trauger, S. A., Siuzdak, G., and Cravatt, B. F. (2013). ABHD12 controls brain lysophosphatidylserine pathways that are deregulated in a murine model of the neurodegenerative disease PHARC. Proc Natl Acad Sci USA 110, 1500-1505.

Blankman, J L, Simon, G. M., and Cravatt, B. F. (2007). A comprehensive profile of brain enzymes that hydrolyze the endocannabinoid 2-arachidonoylglycerol. Chemistry & biology 14, 1347-1356.

Carlson, A. E., Westenbroek, R. E., Quill, T., Ren, D., Clapham, D. E., Hille, B., Garbers, D. L., and Babcock, D. F. (2003). CatSper1 required for evoked Ca2+ entry and control of flagellar function in sperm. Proc Natl Acad Sci USA 100, 14864-14868.

Chen, C. C., Akopian, A. N., Sivilotti, L., Colquhoun, D., Burnstock, G., and Wood, J. N. (1995). A P2X purinoceptor expressed by a subset of sensory neurons. Nature 377, 428-431.

Chung, J. J., Navarro, B., Krapivinsky, G., Krapivinsky, L., and Clapham, D. E. (2011). A novel gene required for male fertility and functional CATSPER channel formation in spermatozoa. Nat Commun 2, 153.

Cociorva, D., D, L. T., and Yates, J. R. (2007). Validation of tandem mass spectrometry database search results using DTASelect. Current protocols in bioinformatics/editoral board, Andreas D Baxevanis [et al] Chapter 13, Unit 13 14.

Di Marzo, V., Bifulco, M., and De Petrocellis, L. (2004). The endocannabinoid system and its therapeutic exploitation. Nature reviews Drug discovery 3, 771-784.

Eisenbach, M., and Gioj alas, L. C. (2006). Sperm guidance in mammals—an unpaved road to the egg. Nat Rev Mol Cell Biol 7, 276-285.

Evans, R. M. (1988). The steroid and thyroid hormone receptor superfamily. Science 240, 889-895.

Fahy, E., Sud, M., Cotter, D., and Subramaniam, S (2007). LIPID MAPS online tools for lipid research. Nucleic acids research 35, W606-612.

Fan, J., Lu, Y., Yu, L. H., Zhang, Y., Ni, X., Burnstock, G., and Ma, B. (2011). Progesterone rapidly attenuates ATP-evoked transient currents in cultured rat dorsal root ganglion neurons. Pharmacology 87, 36-44.

Guo, F., Chiang, M. Y., Wang, Y., and Zhang, Y. Z. (2008). An in vitro recombination method to convert restriction- and ligation-independent expression vectors. Biotechnology journal 3, 370-377.

Hara, A., and Radin, N. S. (1978). Lipid extraction of tissues with a low-toxicity solvent. Analytical biochemistry 90, 420-426.

Jin, S., Zhao, G., Li, Z., Nishimoto, Y., Isohama, Y., Shen, J., Ito, T., Takeya, M., Araki, K., He, P., et al. (2009). Age-related pulmonary emphysema in mice lacking alpha/beta hydrolase domain containing 2 gene. Biochem Biophys Res Commun 380, 419-424.

Kirichok, Y., Navarro, B., and Clapham, D. E. (2006). Whole-cell patch-clamp measurements of spermatozoa reveal an alkaline-activated Ca2+ channel. Nature 439, 737-740.

Lenzi, A., Gandini, L., Maresca, V., Rago, R., Sgro, P., Dondero, F., and Picardo, M. (2000). Fatty acid composition of spermatozoa and immature germ cells. Mol Hum Reprod 6, 226-231.

Lishko, P., Clapham, D. E., Navarro, B., and Kirichok, Y. (2013). Sperm patch-clamp. Methods in enzymology 525, 59-83.

Lishko, P. V., Botchkina, I. L., Fedorenko, A., and Kirichok, Y. (2010). Acid extrusion from human spermatozoa is mediated by flagellar voltage-gated proton channel. Cell 140, 327-337.

Lishko, P. V., Botchkina, I. L., and Kirichok, Y. (2011). Progesterone Activates the Principal Ca2+ Channel of Human Sperm. Nature 471, 387-391.

Lishko, P. V., Kirichok, Y., Ren, D., Navarro, B., Chung, J. J., and Clapham, D. E. (2012). The control of male fertility by spermatozoan ion channels. Annu Rev Physiol 74, 453-475.

Liu, J., Xia, J., Cho, K. H., Clapham, D. E., and Ren, D. (2007). CatSperbeta, a novel transmembrane protein in the CatSper channel complex. J Biol Chem 282, 18945-18952.

Liu, L., Li, X., Yuan, R., Zhang, H., Qiang, L., Shen, J., and Jin, S. (2015). Associations of ABHD2 genetic variations with risks for chronic obstructive pulmonary disease in a Chinese Han population. PLoS One 10, e0123929.

Long, J. Z., and Cravatt, B. F. (2011). The metabolic serine hydrolases and their functions in mammalian physiology and disease. Chemical reviews 111, 6022-6063.

Losel, R., Breiter, S., Seyfert, M., Wehling, M., and Falkenstein, E. (2005). Classic and non-classic progesterone receptors are both expressed in human spermatozoa. Hormone and metabolic research=Hormon- and Stoffwechselforschung=Hormones et metabolisme 37, 10-14.

Losel, R., and Wehling, M. (2003). Nongenomic actions of steroid hormones. Nat Rev Mol Cell Biol 4, 46-56.

Losel, R. M., Falkenstein, E., Feuring, M., Schultz, A., Tillmann, H. C., Rossol-Haseroth, K., and Wehling, M. (2003). Nongenomic steroid action: controversies, questions, and answers. Physiol Rev 83, 965-1016.

Luconi, M., Francavilla, F., Porazzi, I., Macerola, B., Forti, G., and Baldi, E. (2004). Human spermatozoa as a model for studying membrane receptors mediating rapid nongenomic effects of progesterone and estrogens. Steroids 69, 553-559.

Manson, J. E. (2010). Pain: sex differences and implications for treatment. Metabolism: clinical and experimental 59 Suppl 1, S16-20.

McDonald, W. H., Tabb, D. L., Sadygov, R. G., MacCoss, M. J., Venable, J., Graumann, J., Johnson, J. R., Cociorva, D., and Yates, J. R., 3rd (2004). MS1, MS2, and SQT-three unified, compact, and easily parsed file formats for the storage of shotgun proteomic spectra and identifications. Rapid communications in mass spectrometry: RCM 18, 2162-2168.

Miyata, K., Oike, Y., Hoshii, T., Maekawa, H., Ogawa, H., Suda, T., Araki, K., and Yamamura, K. (2005). Increase of smooth muscle cell migration and of intimal hyperplasia in mice lacking the alpha/beta hydrolase domain containing 2 gene. Biochem Biophys Res Commun 329, 296-304.

Morrison, D. A., and Goldman, A. L. (1986). Oral progesterone treatment in chronic obstructive lung disease: failure of voluntary hyperventilation to predict response. Thorax 41, 616-619.

Navarro, B., Kirichok, Y., Chung, J. J., and Clapham, D. E. (2008). Ion channels that control fertility in mammalian spermatozoa. Int J Dev Biol 52, 607-613.

Navia-Paldanius, D., Savinainen, J. R., and Laitinen, J. T. (2012). Biochemical and pharmacological characterization of human alpha/beta-hydrolase domain containing 6 (ABHD6) and 12 (ABHD12). Journal of lipid research 53, 2413-2424.

Park, S. K., Venable, J. D., Xu, T., and Yates, J. R., 3rd (2008). A quantitative analysis software tool for mass spectrometry-based proteomics. Nature methods 5, 319-322.

Peng, J., Elias, J. E., Thoreen, C. C., Licklider, L. J., and Gygi, S. P. (2003). Evaluation of multidimensional chromatography coupled with tandem mass spectrometry (LC/LC-MS/MS) for large-scale protein analysis: the yeast proteome. Journal of proteome research 2, 43-50.

Qi, H., Moran, M. M., Navarro, B., Chong, J. A., Krapivinsky, G., Krapivinsky, L., Kirichok, Y., Ramsey, I. S., Quill, T. A., and Clapham, D. E. (2007). All four CatSper ion channel proteins are required for male fertility and sperm cell hyperactivated motility. Proc Natl Acad Sci USA 104, 1219-1223.

Quill, T. A., Ren, D., Clapham, D. E., and Garbers, D. L. (2001). A voltage-gated ion channel expressed specifically in spermatozoa. Proc Natl Acad Sci USA 98, 12527-12531.

Quill, T. A., Sugden, S. A., Rossi, K. L., Doolittle, L. K., Hammer, R. E., and Garbers, D. L. (2003). Hyperactivated sperm motility driven by CatSper2 is required for fertilization. Proc Natl Acad Sci USA 100, 14869-14874.

Ralt, D., Goldenberg, M., Fetterolf, P., Thompson, D., Dor, J., Mashiach, S., Garbers, D. L., and Eisenbach, M. (1991). Sperm attraction to a follicular factor(s) correlates with human egg fertilizability. Proc Natl Acad Sci USA 88, 2840-2844.

Rejraji, H., Sion, B., Prensier, G., Carreras, M., Motta, C., Frenoux, J. M., Vericel, E., Grizard, G., Vernet, P., and Drevet, J. R. (2006). Lipid remodeling of murine epididymosomes and spermatozoa during epididymal maturation. Biol Reprod 74, 1104-1113.

Ren, D., Navarro, B., Perez, G., Jackson, A. C., Hsu, S., Shi, Q., Tilly, J. L., and Clapham, D. E. (2001). A sperm ion channel required for sperm motility and male fertility. Nature 413, 603-609.

Ren, D., and Xia, J. (2010). Calcium signaling through CatSper channels in mammalian fertilization. Physiology (Bethesda) 25, 165-175.

Revelli, A., Massobrio, M., and Tesarik, J. (1998). Nongenomic actions of steroid hormones in reproductive tissues. Endocr Rev 19, 3-17.

Safarinejad, M. R., Hosseini, S. Y., Dadkhah, F., and Asgari, M. A. (2010). Relationship of omega-3 and omega-6 fatty acids with semen characteristics, and anti-oxidant status of seminal plasma: a comparison between fertile and infertile men. Clinical nutrition (Edinburgh, Scotland) 29, 100-105.

Savinainen, J. R., Patel, J. Z., Parkkari, T., Navia-Paldanius, D., Marjamaa, J. J., Laitinen, T., Nevalainen, T., and Laitinen, J. T. (2014). Biochemical and pharmacological characterization of the human lymphocyte antigen B-associated transcript 5 (BATS/ABHD16A). PLoS One 9, e109869.

Schaeffer, V., Meyer, L., Patte-Mensah, C., and Mensah-Nyagan, A. G. (2010). Progress in dorsal root ganglion neurosteroidogenic activity: basic evidence and pathophysiological correlation. Progress in neurobiology 92, 33-41.

Schuel, H., and Burkman, L. J. (2005). A tale of two cells: endocannabinoid-signaling regulates functions of neurons and sperm. Biol Reprod 73, 1078-1086.

Simoncini, T., and Genazzani, A. R. (2003). Non-genomic actions of sex steroid hormones. European journal of endocrinology/European Federation of Endocrine Societies 148, 281-292.

Smith, J. F., Syritsyna, O., Fellous, M., Serres, C., Mannowetz, N., Kirichok, Y., and Lishko, P. V. (2013). Disruption of the principal, progesterone-activated sperm Ca2+ channel in a CatSper2-deficient infertile patient. Proc Natl Acad Sci USA 110, 6823-6828.

Strunker, T., Goodwin, N., Brenker, C., Kashikar, N., Weyand, I., Seifert, R., and Kaupp, U. B. (2011). The CatSper channel mediates progesterone-induced Ca2+ influx in human sperm. Nature 471, 382-386.

Sumigama S., M. S., Miller M., Lishko P., Cherr G, Meyers S. and Tollner T. (2015). Progesterone accelerates the completion of sperm capacitation and activates CatSper channel in spermatozoa from the rhesus macaque. Proc Natl Acad Sci USA.

Tabb, D. L., McDonald, W. H., and Yates, J. R., 3rd (2002). DTASelect and Contrast: tools for assembling and comparing protein identifications from shotgun proteomics. Journal of proteome research 1, 21-26.

Teves, M. E., Barbano, F., Guidobaldi, H. A., Sanchez, R., Miska, W., and Giojalas, L. C. (2006). Progesterone at the picomolar range is a chemoattractant for mammalian spermatozoa. Fertil Steril 86, 745-749.

Wang, H., Liu, J., Cho, K. H., and Ren, D. (2009). A novel, single, transmembrane protein CATSPERG is associated with CATSPER1 channel protein. Biol Reprod 81, 539-544.

Wennemuth, G., Babcock, D. F., and Hille, B. (2003). Calcium clearance mechanisms of mouse sperm. The Journal of general physiology 122, 115-128.

Xia, J., Reigada, D., Mitchell, C. H., and Ren, D. (2007). CATSPER channel-mediated Ca2+ entry into mouse sperm triggers a tail-to-head propagation. Biol Reprod 77, 551-559.

Xia, J., and Ren, D. (2009). The BSA-induced Ca2+ influx during sperm capacitation is CATSPER channel-dependent. Reprod Biol Endocrinol 7, 119.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of modulating the level and/or activity of an abhydrolase domain-containing protein 2 (ABHD2) polypeptide in a cell, the method comprising contacting the cell with an agent that modulates the level and/or activity of the ABHD2 polypeptide, wherein the agent is a serine hydrolase inhibitor that specifically inhibits ABHD2.

2. The method of claim 1, wherein the cell is a sperm cell, and wherein the agent decreases the level and/or activity of the ABHD2 polypeptide in the cell.

3. The method of claim 1, wherein the cell is a dorsal root ganglion, and wherein the agent increases the level and/or activity of the ABHD2 polypeptide in the cell.

4. The method of claim 1, wherein the cell is a lung cell, and wherein the agent increases the level and/or activity of the ABHD2 polypeptide in the cell.

* * * * *

UNITED STATES PATENT AND TRADEMARK OFFICE
CERTIFICATE OF CORRECTION

PATENT NO. : 11,273,167 B2  
APPLICATION NO. : 15/747104  
DATED : March 15, 2022  
INVENTOR(S) : Polina V. Lishko et al.

Page 1 of 1

It is certified that error appears in the above-identified patent and that said Letters Patent is hereby corrected as shown below:

In the Specification

In Column 31, Line 18, please replace "(344,5-dimethylthiazol-2-yl)-2,5-diphenyl-2 H-tetrazolium bromide" with --(3-(4,5-dimethylthiazol-2-yl)-2,5-diphenyl-2 H-tetrazolium bromide--

In Column 34, Line 8, please replace "M" with --MΩ--

Signed and Sealed this  
Twenty-eighth Day of June, 2022

Katherine Kelly Vidal  
*Director of the United States Patent and Trademark Office*